United States Patent
Macias et al.

(10) Patent No.: US 11,926,669 B2
(45) Date of Patent: Mar. 12, 2024

(54) ANTI-FcRn ANTIBODY OR ANTIGEN BINDING FRAGMENT THEREOF WITH IMPROVED STABILITY

(71) Applicants: HANALL BIOPHARMA CO., LTD., Daejeon (KR); Immunovant Sciences GmbH, Basel (CH)

(72) Inventors: William Louis Macias, Indianapolis, IN (US); Su Liang, Briarcliff Manor, NY (US); Hyeakyung Ahn, Gyeonggi-do (KR); Haeyoung Yong, Gyeonggi-do (KR); Mijin Jung, Gyeonggi-do (KR); Minho Yoon, Gyeonggi-do (KR); Eunsun Kim, Seoul (KR); Seungkook Park, Seoul (KR); Hyeeun Shim, Seoul (KR)

(73) Assignees: HANALL BIOPHARMA CO., LTD., Daejeon (KR); IMMUNOVANT SCIENCES GMBH, Basel (CH)

(*) Notice: Subject to any disclaimer, the term of this patent is extended or adjusted under 35 U.S.C. 154(b) by 0 days.

(21) Appl. No.: 18/340,722

(22) Filed: Jun. 23, 2023

(65) Prior Publication Data

US 2023/0391876 A1  Dec. 7, 2023

Related U.S. Application Data

(63) Continuation of application No. PCT/US2023/067539, filed on May 26, 2023.

(60) Provisional application No. 63/499,116, filed on Apr. 28, 2023, provisional application No. 63/377,283, filed on Sep. 27, 2022, provisional application No. 63/370,772, filed on Aug. 8, 2022, provisional application No. 63/352,948, filed on Jun. 16, 2022.

(51) Int. Cl.
| | | |
|---|---|---|
| *C07K 16/00* | (2006.01) | |
| *A61P 37/06* | (2006.01) | |
| *C07K 16/28* | (2006.01) | |
| *A61K 39/00* | (2006.01) | |

(52) U.S. Cl.
CPC ............ *C07K 16/283* (2013.01); *A61P 37/06* (2018.01); *A61K 2039/505* (2013.01); *A61K 2039/545* (2013.01); *C07K 2317/52* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,714,350 | A | 2/1998 | Co et al. |
| 7,662,928 | B2 | 2/2010 | Balthasar |
| 8,273,351 | B2 | 9/2012 | Tenhoor et al. |
| 8,815,246 | B2 | 8/2014 | Tenhoor et al. |
| 9,085,625 | B2 | 7/2015 | Labrijn et al. |
| 9,260,520 | B2 | 2/2016 | Tenhoor et al. |
| 9,359,438 | B2 | 6/2016 | Sexton et al. |
| 10,336,825 | B2 | 7/2019 | Kim et al. |
| 10,544,226 | B2 | 1/2020 | Kim et al. |
| 11,613,578 | B2 | 3/2023 | Kim et al. |
| 2005/0079169 | A1 | 4/2005 | Balthasar et al. |
| 2007/0092507 | A1 | 4/2007 | Balthasar et al. |
| 2009/0098134 | A1 | 4/2009 | Buelow |
| 2010/0166734 | A1 | 7/2010 | Dolk |
| 2010/0212035 | A1 | 8/2010 | Buelow |
| 2010/0266530 | A1 | 10/2010 | Roopenian et al. |
| 2010/0322930 | A1 | 12/2010 | Kolbinger et al. |
| 2013/0045218 | A1 | 2/2013 | Tenhoor et al. |
| 2013/0330323 | A1 | 12/2013 | Dunn et al. |
| 2013/0345406 | A1 | 12/2013 | Van De Winkel |
| 2015/0111249 | A1 | 4/2015 | Bassett et al. |
| 2015/0118240 | A1 | 4/2015 | Finney et al. |
| 2016/0108119 | A1 | 4/2016 | Spitali et al. |
| 2016/0137713 | A1 | 5/2016 | Kim et al. |
| 2016/0194397 | A1 | 7/2016 | Tenhoor et al. |
| 2016/0222108 | A1 | 8/2016 | Tenhoor et al. |
| 2016/0222111 | A1 | 8/2016 | Tenhoor et al. |
| 2016/0257744 | A1 | 9/2016 | Fuh et al. |
| 2016/0264668 | A1 | 9/2016 | Atherfold et al. |
| 2016/0304608 | A1 | 10/2016 | Sexton et al. |
| 2017/0029521 | A1 | 2/2017 | Van De Winkel et al. |

(Continued)

FOREIGN PATENT DOCUMENTS

| | | |
|---|---|---|
| EP | 2850101 A1 | 3/2015 |
| EP | 2373687 B1 | 10/2016 |

(Continued)

OTHER PUBLICATIONS

Obrezanova et al., MAbs. 2015;7(2):352-63. doi: 10.1080/19420862.2015.1007828. PMID: 25760769.*
Lonza Product News for Sentinel APART, Basel, Switzerland, Mar. 30, 2016, 3 pages, no autor listed.*
International Search Report and Written Opinion for International Application No. PCT/US2023/067539 dated Aug. 17, 2023, 15 pages.
Acaster et al., "Qualitative and quantitative validation of the FACIT-fatigue scale in iron deficiency anemia," Health Qual. Life Outcomes, May 2015, 13(60):1-10.

(Continued)

*Primary Examiner* — Michael Szperka
(74) *Attorney, Agent, or Firm* — COOLEY LLP

(57) ABSTRACT

The present disclosure relates to an anti-FcRn antibody or an antigen binding fragment thereof with improved stability and uses thereof. The anti-FcRn antibody or antigen binding fragment thereof binds to FcRn non-competitively with IgG and the like compared to the parent antibody, HL161AN, thereby having improved stability, such as reducing the production rate of aggregates while maintaining the biological activity of significantly reducing the amount of pathogenic autoantibodies in the blood. Therefore, it may be utilized more efficiently for the treatment of an autoimmune disease.

20 Claims, 22 Drawing Sheets

Specification includes a Sequence Listing.

(56) References Cited

U.S. PATENT DOCUMENTS

| | | |
|---|---|---|
| 2017/0045528 A1 | 2/2017 | Blumberg et al. |
| 2017/0072032 A1 | 3/2017 | Mallone et al. |
| 2017/0210801 A1 | 7/2017 | Kim et al. |
| 2017/0210805 A1 | 7/2017 | Kim et al. |
| 2017/0233461 A1 | 8/2017 | Torres et al. |
| 2019/0135917 A1 | 5/2019 | Kim et al. |
| 2022/0002402 A1 | 1/2022 | Fong et al. |
| 2023/0049011 A1 | 2/2023 | Coquery et al. |
| 2023/0235063 A1 | 7/2023 | Kim et al. |

FOREIGN PATENT DOCUMENTS

| | | | |
|---|---|---|---|
| EP | 2310415 | B1 | 10/2017 |
| KR | 20130071961 | A | 7/2013 |
| KR | 101815265 | B1 | 1/2018 |
| KR | 101954906 | B1 | 3/2019 |
| WO | WO-2004102184 | A1 | 11/2004 |
| WO | WO-2005013912 | A2 | 2/2005 |
| WO | WO-2006118772 | A2 | 11/2006 |
| WO | WO-2007087289 | A2 | 8/2007 |
| WO | WO-2009080764 | A2 | 7/2009 |
| WO | WO-2009131702 | A2 | 10/2009 |
| WO | WO-2012167039 | A1 | 12/2012 |
| WO | WO-2014019727 | A1 | 2/2014 |
| WO | WO-2014177460 | A1 | 11/2014 |
| WO | WO-2014204280 | A1 | 12/2014 |
| WO | WO-2015071330 | A1 | 5/2015 |
| WO | WO-2015107026 | A1 | 7/2015 |
| WO | WO-2015167293 | A1 * | 11/2015 ........... A61K 39/395 |
| WO | WO-2016123521 | A2 | 8/2016 |
| WO | WO-2016180765 | A1 | 11/2016 |
| WO | WO-2016183352 | A1 | 11/2016 |
| WO | WO-2017189556 | A1 | 11/2017 |
| WO | WO-2017194646 | A1 | 11/2017 |
| WO | WO-2020097099 | A1 | 5/2020 |
| WO | WO-2021101975 | A1 | 5/2021 |
| WO | WO-2022005113 | A1 | 1/2022 |

OTHER PUBLICATIONS

Bahn et al., "Pathogenesis of Graves' Ophthalmopathy," The New England Journal of Medicine, Nov. 11, 1993, 329(20):1468-1475.
Barcellini, "New Insights in the Pathogenesis of Autoimmune Hemolytic Anemia," Transfus. Med. Hemother., Sep. 2015, 42(5):287-293.
Bartalena et al., "Consensus Statement of the European Group on Graves' Orbitopathy (EUGOGO) on Management of Graves' Orbitopathy" Thyroid, Mar. 2008, 18(3):333-346 (28 pages total).
Berentsen, "Role of Complement in Autoimmune Hemolytic Anemia," Transfus. Med. Hemother., Sep. 2015, 42(5):303-310.
Blumberg, L. et al. "SYNT001: A Humanized IgG4 Monoclonal Antibody That Disrupts the Interaction of FcRn and IgG for the Treatment of IgG-Mediated Autoimmune Diseases," Blood, Dec. 7, 2017, 130(1):3483, 3 pages.
Caron et al., "Engineered Humanized Dimeric Forms of IgG Are More Effective Antibodies" the Journal of Experimental Medicine, Oct. 1992, 176(4):1191-1195.
Christianson, G., et al., "Monoclonal antibodies directed against human FcRn and their applications", "mAbs", Mar.-Apr. 2012, 4(2):208-216.
ClinicalTrials.gov Identifier: NCT03075878, "A Safety Study of SYNT001 in Participants With Warm Autoimmune Hemolytic Anemia (WAIHA)" Last Update Posted May 13, 2020, 7 pages.
ClinicalTrials.gov Identifier: NCT03226678, "Study to Assess the Safety, Tolerability, Efficacy and PK of APL-2 in Patients With Warm Type Autoimmune Hemolytic Anemia (wAIHA) or Cold Agglutinin Disease (CAD)," Last Update Posted Nov. 24, 2020, 7 pages.
ClinicalTrials.gov Identifier: NCT03764618, "A Phase 3, Multi-Center, Randomized, Double-Blind, Placebo-Controlled, Study of Fostamatinib Disodium in the Treatment of wAIHA," Last Update Posted Jan. 12, 2023, 6 pages.
ClinicalTrials.gov identifier: NCT03922321, "Study of RVT-1401 for the Treatment of Patients with Moderate to Severe Active Graves' Ophthalmopathy (Go)" Last Update Posted Jul. 16, 2019, 7 pages.
ClinicalTrials.gov Identifier: NCT03938545, "ASCEND GO-2: Study of RVT-1401 for the Treatment of Patients with Active, Moderate to Severe Graves' Ophthalmopathy (GO)," Last Update Posted Dec. 20, 2019, 9 pages.
ClinicalTrials.gov Identifier: NCT04119050, "Efficacy and Safety of M281 in Adults With Warm Autoimmune Hemolytic Anemia," Last Update Posted Feb. 15, 2023, 9 pages.
De Groot and Scott, "Immunogenicity of protein therapeutics," Trends in Immunology, 2007, 28(11):482-490.
Devlin et al., "Valuing health-related quality of life: An EQ-5D-5L value set for England," Health Economics, Jan. 2018, 27(1):7-22.
Dondelinger et al., "Understanding the Significance and Implications of Antibody Numbering and Antigen-Binding Surface/Residue Definition," Frontiers in Immunology, Oct. 2018, 9:2278, 15 pages.
Engels and Uhlmann, "Gene Synthesis," Adv. Biochem Eng. Biotechnol., 1988, 37:73-127.
European Patent Application No. 15785500.8, by Hanall Biopharma Co., Ltd.: Examination Report, dated Jul. 9, 2020, 5 pages.
European Patent Application No. 15785500.8, by Hanall Biopharma Co., Ltd.: Extended European Search Report, including Supplementary Search Report and Opinion, dated Jan. 30, 2018, 20 pages.
Ferrari et al., "Anemia and hemoglobin serum levels are associated with exercise capacity and quality of life in chronic obstructive pulmonary disease," BMC Pulm. Med., May 2015, vol. 15(58):1-8.
Final Office Action issued in U.S. Appl. No. 15/301,948, dated Apr. 25, 2019, 6 pages.
Hernández-Alava et al., EEPRU Report: "Quality review of proposed EQ-5D-5L value set for England," Oct. 2018, 69 pages.
International Search Report and Written Opinion issued in PCT/KR2015/004424, dated Jul. 8, 2015, 12 pages.
International Search Report and Written Opinion issued in PCT/US2019/059894 dated Feb. 6, 2020, 17 pages.
International Search Report and Written Opinion issued in PCT/US2020/061028, dated Mar. 5, 2021, 11 pages.
Kalfa, "Warm antibody autoimmune hemolytic anemia," Hematology Am. Soc. Hematol. Educ. Program, Dec. 2016, 2016(1):690-697.
Khoo et al., "Graves' Ophthalmopathy in the Absence of Elevated Free Thyroxine and Triiodothyronine Levels: Prevalence, Natural History, and Thyrotropin Receptor Antibody Levels," Thyroid, Dec. 2000, 10(12):1093-1100 (12 pages total).
Krieger et al., "Bidirectional TSH and IGF-1 Receptor Cross Talk Mediates Stimulation of Hyaluronan Secretion by Graves' Disease Immunoglobins," J. Clin. Endocrinol. Metab., Mar. 2015, 100(3):1071-1077.
Li, N., et al., "Complete FcRn dependence for intravenous Ig therapy in autoimmune skin blistering diseases", "The Journal of Clinical Investigation", Dec. 2005, 115(12):3440-3450.
Lobuglio et al., "Red Cells Coated with Immunoglobulin G: Binding and Sphering by Mononuclear Cells in Man," Science, Dec. 22, 1967, 158(3808):1582-1585.
Lonberg, N. "Fully human antibodies from transgenic mouse and phage display platforms" Curr Opin Immunol, Aug. 2008, 20:450-459.
Maheshwari and Weis, "Thyroid associated orbitopathy," Indian J. Ophthalmol., Mar. 2012, 60(2):87-93.
Marcocci, C., et al., "Treatment of mild, moderate-to-severe and very severe Graves' orbitopathy", Bailliere's Best Practice and Research. Clinical Endocrinology and Metabolism, Jun. 1, 2012, 26(3):325-337.
Menconi et al., "Diagnosis and classification of Graves' disease" Autoimmun. Rev. Apr.-May 2014, 13(4-5):398-402.
Ménoret, S., et al., "Characterization of immunoglobulin heavy chain knockout rats", European Journal of Immunology, Oct. 2010, 40:2932-2941.
Michel, "Classification and therapeutic approaches in autoimmune hemolytic anemia: an update," Expert Rev. Hematol., Dec. 2011, 4(6):607-618.

(56) References Cited

OTHER PUBLICATIONS

Miguel et al., "Review of the treatment of Graves' ophthalmopathy: The role of the new radiation techniques," Saudi J. Ophthalmol. Apr.-Jun. 2018, 32(2):139-145.
Morell et al., "Metabolic Properties of IgG Subclasses in Man," J. Clin. Invest., Apr. 1970, 49(4):673-680.
Mourits et al., "Clinical activity score as a guide in the management of patients with Graves' ophthalmopathy" Clin. Endocrinol., Jul. 1997, 47(1):9-14.
Mourits et al., "Clinical criteria for the assessment of disease activity in Graves' ophthalmopathy: a novel approach," Br. J. Ophthalmol., Aug. 1989, 73:639-44.
Non-Final Office Action issued in U.S. Appl. No. 15/301,948, dated Jan. 25, 2019, 10 pages.
Non-Final Office Action issued in U.S. Appl. No. 16/248,083, dated Mar. 16, 2021, 9 pages.
Odom et al., "Tissue-Specific Transcriptional Regulation has Diverged Significantly between Human and Mouse," Nature Genetics, Jun. 2007, 39(6):730-732 (8 pages total).
Osborn, M.J. et al., "High-Affinity IgG Antibodies Develop Naturally in Ig-Knockout Rats Carrying Germline Human IgH/Igκ/Igλ Loci Bearing the Rat $C_H$ region" J Immunol., Feb. 15, 2013, 190(4):1481-1490.
Praetor, A., et al., "β2-microglobulin is important for cell surface expression and pH-dependent IgG binding of human FcRn", Journal of Cell Science, Jun. 1, 2002, 115:2389-2397.
Pritchard et al. "Immunoglobulin Activation of T Cell Chemoattractant Expression in Fibroblasts from Patients with Graves' Disease Is Mediated Through the Insulin-Like Growth Factor I Receptor Pathway," J. Immunol., Jun. 2003, 170:6348-6354.
Rath, T., et al., "The Immunologic Functions of the Neonatal Fc Receptor for IgG", Journal of Clinical Immunology: Author Manuscript, Jan. 2013, 33(Suppl 1):9-17, 15 pages total.
Roopenian et al., "The MHC Class I-Like IgG Receptor Controls Perinatal IgG Transport, IgG Homeostasis, and Fate of IgG-Fc-Coupled Drugs," J. Immunol., Apr. 2003, 170:3528-3533.
Salvi et al., "Efficacy of B-cell Targeted Therapy With Rituximab in Patients With Active Moderate to Severe Graves' Orbitopathy: A Randomized Controlled Study," J. Clin. Endocrinol. Metab., Feb. 2015, 100(2):422-31, Epub Dec. 15, 2014.
Saunders "Conceptual Approaches to Modulating Antibody Effector Functions and Circulation Half-Life," Front. Immunol., Jun. 2019, 10:1296, 20 pages.
Schwab, I., et al., "Intravenous immunoglobulin therapy: how does IgG modulate the immune system?", Nature Reviews: Immunology, Mar. 2013, 13:176-189.
Shopes, B., "A genetically engineered human IgG mutant with enhanced cytolytic activity," The Journal of Immunology, May 1992, 148(9):2918-2922.
Sokol et al., "Autoimmune haemolysis: an 18-year study of 865 cases referred to a regional transfusion centre," Br. Med. J. (Clin. Res. Ed.), Jun. 20, 1981, 282:2023-2027.
Stan et al., "Randomized Controlled Trial of Rituximab in Patients With Graves' Orbitopathy," J. Clin. Endocrinol. Metab, Feb. 2015, 100(2):432-441.
Stan et al. "The Evaluation and Treatment of Graves Ophthalmopathy," Med. Clin. North Am., Mar. 2012, 96(2):311-328.
Stenton, "The MRC breathlessness scale" Occupational Med., May 2008, 58:226-227.
Stevenson et al., "A chimeric antibody with dual Fc regions (bisFabFc) prepared by manipulations at the IgG hinge," Anti-Cancer Drug Design, Mar. 1989, 3(4):219-230.
Terwee et al., "Development of a disease specific quality of life questionnaire for patients with Graves' ophthalmopathy: the GO-QOL," Br. J. Ophthalmol., Jul. 1998, 82:773-779.
Terwee et al., "Interpretation and validity of changes in scores on the Graves' ophthalmopathy quality of life questionnaire (GO-QOL) after different treatments," Clin. Endocrinol., Mar. 2001, 54(3):391-398.
Tsui et al., "Evidence of an association between TSH and IGF-1 receptors," J. Immunol., Sep. 15, 2008, 181(6):4397-4405 (21 pages total).
UniProtKB/Swiss-Prot: P61769.1, "RecName: Full=Beta-2-microglobulin; Contains: RecName: Full=Beta-2-microglobulin form pI 5.3; Flags: Precursor," Jun. 28, 2023, 17 pages.
UniProtKB/Swiss-Prot: P55899.1, "RecName: Full=IgG receptor FcRn large subunit p51; Short=FcRn; AltName: Full=IgG Fc fragment receptor transporter alpha chain; AltName: Full=Neonatal Fc receptor; Flags: Precursor," Jun. 28, 2023, 8 pages.
Vitetta et al., "Immunology. Considering therapeutic antibodies" Science, Jul. 2006, 313:308-309.
Wang, et al., "Antibody structure, instability, and formulation," Journal of Pharmaceutical Sciences, Jan. 2007, 96(1):1-26.
Wang, X. et al. "IgG Fc engineering to modulate antibody effector functions," Protein Cell, 2018, 9(1):63-73.
Webster et al., "The Functional Assessment of Chronic Illness Therapy (FACIT) Measurement System: properties, applications, and interpretation," Health Qual. Life Outcomes, Dec. 16, 2003, 1(79):1-7.
Wiersinga, "Advances in treatment of active, moderate-to-severe Graves' ophthalmopathy" Lancet Diabetes Endocrinol., Feb. 2017, 5(2):134-142.
Yeatts, "Quality of Life in Patients with Graves Ophthalmopathy," Trans. Am. Ophthalmol. Soc., 2005, 103:368-411.
Zanella et al. "Treatment of autoimmune hemolytic anemias," Haematologica, Oct. 2014, 99(10):1547-1554.
Extended European Search Report for European Application No. EP23172456.8 dated Oct. 13, 2023, 11 pages.
Office Action for Brazilian Application No. BR1120160253191 dated Oct. 18, 2023, 9 pages.
Pearson, W.R. "An Introduction to Sequence Similarity ("Homology") Searching," Curr Protoc Bioinformatics, Jun. 2013, 42(1), 9 pages.

* cited by examiner

FIG. 3

```
HL161AN_HC      VQLLESGGGLVQPGGSLRLSCAASEFTFGSCVMTWVRQAPGKGLEWVSVISGGGETYY
                        10        20        30        40        50        60
                                                    VH-CDR-H1      CDR-H2

HL161AN_HC      ADSVKGRFTISRDNSKNTVYLQMNSLRAEDTAVYYCARPWWLRSFFFDYWGQGTLVTVS
                        70        80        90        100       110       120
                 CDR-H2                              CDR-H3
                                                CH1

HL161AN_HC      SASTKGPSVFPLAPSSKSTSGGTAALGCLVKDYFPEPVTVSWNSGALTSGVHTFPAVLQS
                        130       140       150       160       170       180
                                        CH1

HL161AN_HC      SGLYSLSSVVTVPSSSLGTQTYICNVNHKPSNTKVDKRVEPKSCDKTHTCPPCPAPEAAG
                        190       200       210       220       230       240
                                                              HINGE    CH2

HL161AN_HC      GPSVFLFPPKPKDTLMISRTPEVTCVVVDVSHEDPEVKFNWYVDGVEVHNAKTKPREEQY
                        250       260       270       280       290       300
                                                                      CH3

HL161AN_HC      NSTYRVVSVLTVLHQDWLNGKEYKCKVSNKALPAPIEKTISKAKGQPREPQVYTLPPSRE
                        310       320       330       340       350       360
                                CH2                           CH3

HL161AN_HC      EMTKNQVSLTCLVKGFYPSDIAVEWESNGQPENNYKTTPPVLDSDGSFFLYSKLTVDKSR
                        370       380       390       400       410       420

HL161AN_HC      WQQGNVFSCSVMHEALHNHYTQKSLSLSPG
                        430       440       450
                            CH3
```

- Asn N-Linked Glycosylation
- Ser/Thr O-Linked Glycosylation
- Asn Deamidation
- Pyro-Glutamate
- Asp Isomerisation/Fragmentation
- Met/Trp Oxidation
- Free Thiol

| Selected PTM sites: | L:Asn25 | H:Cys32 | H:Gln82 |
|---|---|---|---|
| Human Fab (Top) CDR residues within 5Å of the target antigen | | | |
| Proposed substitutions: | Asn → Ser, Gln<br>L:N25S, L:N25Q | Cys → Ser, Tyr<br>H:C32S, H:C32Y | Gln → Ser, Thr, Glu<br>H:Q82S, H:Q82T, H:Q82E |

```
Light chain
                             *
SYVLTQPPSV SVAPGQTARI TCGGNNIGST SVHWYQQKPG QAPVLVVHDD
SDRPSGIPER FSGSNSGNTA TLTISRVEAG DEADYYCQVR DSSSDHVIFG
GGTKLTVLGQ PKAAPSVTLF PPSSEELQAN KATLVCLISD FYPGAVTVAW
KADSSPVKAG VETTTPSKQS NNKYAASSYL SLTPEQWKSH RSYSCQVTHE
GSTVEKTVAP TECS
Heavy chain
                                      *
EVQLLESGGG LVQPGGSLRL SCAASEFTFG SCVMTWVRQA PGKGLEWVSV
                                    *
ISGSGGSTYY ADSVKGRFTI SRDNSKNTLY LQMNSLRAED TAVYYCAKTP
WWLRSPFDY  WGQGTLVTVS SASTKGPSVF PLAPSSKSTS GGTAALGCLV
KDYFPEPVTV SWNSGALTSG VHTFPAVLQS SGLYSLSSVV TVPSSSLGTQ
TYICNVNHKP SNTKVDKRVE PKSCDKTHTC PPCPAPEAAG GPSVFLFPPK
PKDTLMISRT PEVTCVVVDV SHEDPEVKFN WYVDGVEVHN AKTKPREEQY
NSTYRVVSVL TVLHQDWLNG KEYKCKVSNK ALPAPIEKTI SKAKGQPREP
QVYTLPPSRE EMTKNQVSLT CLVKGFYPSD IAVEWESNGQ PENNYKTTPP
VLDSDGSFFL YSKLTVDKSR WQQGNVFSCS VMHEALHNHY TQKSLSLSPG
```

-Bold: Paratope
-Underline: CDRs, IgBLAST kabat scheme
-*: selected amino acid for substitution

FIG. 5

SEQUENCE LISTING

```
Sequence total quantity: 37
SEQ ID NO: 1            moltype = AA  length = 11
FEATURE                 Location/Qualifiers
REGION                  1..11
                        note = LCDR1 of HL161AN
source                  1..11
                        mol_type = protein
                        organism = synthetic construct
SEQUENCE: 1
GGNNIGSTSV H                                                         11

SEQ ID NO: 2            moltype = AA  length = 7
FEATURE                 Location/Qualifiers
REGION                  1..7
                        note = LCDR2 of HL161AN
source                  1..7
                        mol_type = protein
                        organism = synthetic construct
SEQUENCE: 2
DDSDRPS                                                              7

SEQ ID NO: 3            moltype = AA  length = 11
FEATURE                 Location/Qualifiers
REGION                  1..11
                        note = LCDR3 of HL161AN
source                  1..11
                        mol_type = protein
                        organism = synthetic construct
SEQUENCE: 3
QVRDSSSDHV I                                                         11

SEQ ID NO: 4            moltype = AA  length = 119
FEATURE                 Location/Qualifiers
REGION                  1..119
                        note = VL of HL161AN
source                  1..119
                        mol_type = protein
                        organism = synthetic construct
SEQUENCE: 4
SYVLTQPPSV SVAPGQTARI TCGGNNIGST SVHWYQQKPG QAPVLVVHDD SDRPSGIPER     60
FSGSNSGNTA TLTISRVEAG DEADYYCQVR DSSSDHVIFG GGTKLTVLGQ PKAAPSVTL     119

SEQ ID NO: 5            moltype = AA  length = 5
FEATURE                 Location/Qualifiers
REGION                  1..5
```

```
                        note = HCDR1 of HL161AN
source                  1..5
                        mol_type = protein
                        organism = synthetic construct
SEQUENCE: 5
SCVMT                                                                         5

SEQ ID NO: 6            moltype = AA  length = 17
FEATURE                 Location/Qualifiers
REGION                  1..17
                        note = HCDR2 of HL161AN
source                  1..17
                        mol_type = protein
                        organism = synthetic construct
SEQUENCE: 6
VISGSGGSTY YADSVKG                                                           17

SEQ ID NO: 7            moltype = AA  length = 12
FEATURE                 Location/Qualifiers
REGION                  1..12
                        note = HCDR3 of HL161AN
source                  1..12
                        mol_type = protein
                        organism = synthetic construct
SEQUENCE: 7
TPWWLRSPFF DY                                                                12

SEQ ID NO: 8            moltype = AA  length = 121
FEATURE                 Location/Qualifiers
REGION                  1..121
                        note = VH of HL161AN
source                  1..121
                        mol_type = protein
                        organism = synthetic construct
SEQUENCE: 8
EVQLLESGGG LVQPGGSLRL SCAASEFTFG SCVMTWVRQA PGKGLEWVSV ISGSGGSTYY            60
ADSVKGRFTI SRDNSKNTLY LQMNSLRAED TAVYYCAKTP WWLRSPFFDY WGQGTLVTVS           120
S                                                                          121

SEQ ID NO: 9            moltype = AA  length = 11
FEATURE                 Location/Qualifiers
REGION                  1..11
                        note = LCDR1 of HL161ANS
source                  1..11
                        mol_type = protein
                        organism = synthetic construct
SEQUENCE: 9
GGSNIGSTSV H                                                                 11

SEQ ID NO: 10           moltype = AA  length = 119
FEATURE                 Location/Qualifiers
REGION                  1..119
                        note = VL of HL161ANS
source                  1..119
                        mol_type = protein
                        organism = synthetic construct
SEQUENCE: 10
SYVLTQPPSV SVAPGQTARI TCGGSNIGST SVHWYQQKPG QAPVLVVHDD SDRPSGIPER            60
FSGSNSGNTA TLTISRVEAG DEADYYCQVR DSSSDHVIFG GGTKLTVLGQ PKAAPSVTL            119

SEQ ID NO: 11           moltype = AA  length = 5
FEATURE                 Location/Qualifiers
REGION                  1..5
                        note = HCDR1 of HL161ANS or HL161ANQ
source                  1..5
                        mol_type = protein
                        organism = synthetic construct
SEQUENCE: 11
SSVMT                                                                         5

SEQ ID NO: 12           moltype = AA  length = 121
FEATURE                 Location/Qualifiers
REGION                  1..121
                        note = VH of HL161ANS or HL161ANQ
source                  1..121
                        mol_type = protein
                        organism = synthetic construct
SEQUENCE: 12
EVQLLESGGG LVQPGGSLRL SCAASEFTFG SSVMTWVRQA PGKGLEWVSV ISGSGGSTYY            60
```

```
ADSVKGRFTI SRDNSKNTLY LQMNSLRAED TAVYYCAKTP WWLRSPFFDY WGQGTLVTVS    120
S                                                                   121

SEQ ID NO: 13           moltype = AA  length = 11
FEATURE                 Location/Qualifiers
REGION                  1..11
                        note = LCDR1 of HL161ANQ
source                  1..11
                        mol_type = protein
                        organism = synthetic construct
SEQUENCE: 13
GGQNIGSTSV H                                                        11

SEQ ID NO: 14           moltype = AA  length = 119
FEATURE                 Location/Qualifiers
REGION                  1..119
                        note = VL of HL161ANQ
source                  1..119
                        mol_type = protein
                        organism = synthetic construct
SEQUENCE: 14
SYVLTQPPSV SVAPGQTARI TCGGQNIGST SVHWYQQKPG QAPVLVVHDD SDRPSGIPER    60
FSGSNSGNTA TLTISRVEAG DEADYYCQVR DSSSDHVIFG GGTKLTVLGQ PKAAPSVTL     119

SEQ ID NO: 15           moltype = AA  length = 30
FEATURE                 Location/Qualifiers
REGION                  1..30
                        note = FRH1 of HL161AN
source                  1..30
                        mol_type = protein
                        organism = synthetic construct
SEQUENCE: 15
EVQLLESGGG LVQPGGSLRL SCAASEFTFG                                    30

SEQ ID NO: 16           moltype = AA  length = 14
FEATURE                 Location/Qualifiers
REGION                  1..14
                        note = FRH2 of HL161AN
source                  1..14
                        mol_type = protein
                        organism = synthetic construct
SEQUENCE: 16
WVRQAPGKGL EWVS                                                     14

SEQ ID NO: 17           moltype = AA  length = 32
FEATURE                 Location/Qualifiers
REGION                  1..32
                        note = FRH3 of HL161AN
source                  1..32
                        mol_type = protein
                        organism = synthetic construct
SEQUENCE: 17
RFTISRDNSK NTLYLQMNSL RAEDTAVYYC AK                                 32

SEQ ID NO: 18           moltype = AA  length = 11
FEATURE                 Location/Qualifiers
REGION                  1..11
                        note = FRH4 of HL161AN
source                  1..11
                        mol_type = protein
                        organism = synthetic construct
SEQUENCE: 18
WGQGTLVTVS S                                                        11

SEQ ID NO: 19           moltype = AA  length = 214
FEATURE                 Location/Qualifiers
REGION                  1..214
                        note = LC of HL161AN
source                  1..214
                        mol_type = protein
                        organism = synthetic construct
SEQUENCE: 19
SYVLTQPPSV SVAPGQTARI TCGGNNIGST SVHWYQQKPG QAPVLVVHDD SDRPSGIPER    60
FSGSNSGNTA TLTISRVEAG DEADYYCQVR DSSSDHVIFG GGTKLTVLGQ PKAAPSVTLF    120
PPSSEELQAN KATLVCLISD FYPGAVTVAW KADSSPVKAG VETTTPSKQS NNKYAASSYL    180
SLTPEQWKSH RSYSCQVTHE GSTVEKTVAP TECS                                214

SEQ ID NO: 20           moltype = AA  length = 450
FEATURE                 Location/Qualifiers
```

| | | |
|---|---|---|
| REGION | 1..450 | |
| | note = HC of HL161AN(IgG1 null) | |
| source | 1..450 | |
| | mol_type = protein | |
| | organism = synthetic construct | |

SEQUENCE: 20
```
EVQLLESGGG LVQPGGSLRL SCAASEFTFG SCVMTWVRQA PGKGLEWVSV ISGSGGSTYY    60
ADSVKGRFTI SRDNSKNTLY LQMNSLRAED TAVYYCAKTP WWLRSPFFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG                                    450
```

| | | |
|---|---|---|
| SEQ ID NO: 21 | moltype = AA   length = 214 | |
| FEATURE | Location/Qualifiers | |
| REGION | 1..214 | |
| | note = LC of HL161ANS or HL161ANSY or HL161ANSE or HL161ANSYE | |
| source | 1..214 | |
| | mol_type = protein | |
| | organism = synthetic construct | |

SEQUENCE: 21
```
SYVLTQPPSV SVAPGQTARI TCGGSNIGST SVHWYQQKPG QAPVLVVHDD SDRPSGIPER    60
FSGSNSGNTA TLTISRVEAG DEADYYCQVR DSSSDHVIFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214
```

| | | |
|---|---|---|
| SEQ ID NO: 22 | moltype = AA   length = 450 | |
| FEATURE | Location/Qualifiers | |
| REGION | 1..450 | |
| | note = HC of HL161ANS or HL161ANQ(IgG1 null) | |
| source | 1..450 | |
| | mol_type = protein | |
| | organism = synthetic construct | |

SEQUENCE: 22
```
EVQLLESGGG LVQPGGSLRL SCAASEFTFG SSVMTWVRQA PGKGLEWVSV ISGSGGSTYY    60
ADSVKGRFTI SRDNSKNTLY LQMNSLRAED TAVYYCAKTP WWLRSPFFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG                                    450
```

| | | |
|---|---|---|
| SEQ ID NO: 23 | moltype = AA   length = 447 | |
| FEATURE | Location/Qualifiers | |
| REGION | 1..447 | |
| | note = HC of HL161ANS or HL161ANQ(IgG4) | |
| source | 1..447 | |
| | mol_type = protein | |
| | organism = synthetic construct | |

SEQUENCE: 23
```
EVQLLESGGG LVQPGGSLRL SCAASEFTFG SSVMTWVRQA PGKGLEWVSV ISGSGGSTYY    60
ADSVKGRFTI SRDNSKNTLY LQMNSLRAED TAVYYCAKTP WWLRSPFFDY WGQGTLVTVS   120
SASTKGPSVF PLAPCSRSTS ESTAALGCLV KDYFPEPVTV SWNSGALTSG VHTFPAVLQS   180
SGLYSLSSVV TVPSSSLGTK TYTCNVDHKP SNTKVDKRVE SKYGPPCPPC PAPEFLGGPS   240
VFLFPPKPKD TLMISRTPEV TCVVVDVSQE DPEVQFNWYV DGVEVHNAKT KPREEQFNST   300
YRVVSVLTVL HQDWLNGKEY KCKVSNKGLP SSIEKTISKA KGQPREPQVY TLPPSQEEMT   360
KNQVSLTCLV KGFYPSDIAV EWESNGQPEN NYKTTPPVLD SDGSFFLYSR LTVDKSRWQE   420
GNVFSCSVMH EALHNHYTQK SLSLSLG                                       447
```

| | | |
|---|---|---|
| SEQ ID NO: 24 | moltype = AA   length = 214 | |
| FEATURE | Location/Qualifiers | |
| REGION | 1..214 | |
| | note = LC of HL161ANQ or HL161ANQY or HL161ANQE or HL161ANQYE | |
| source | 1..214 | |
| | mol_type = protein | |
| | organism = synthetic construct | |

SEQUENCE: 24
```
SYVLTQPPSV SVAPGQTARI TCGGQNIGST SVHWYQQKPG QAPVLVVHDD SDRPSGIPER    60
FSGSNSGNTA TLTISRVEAG DEADYYCQVR DSSSDHVIFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214
```

| | | |
|---|---|---|
| SEQ ID NO: 25 | moltype = AA   length = 450 | |
| FEATURE | Location/Qualifiers | |

```
REGION                      1..450
                            note = HC of HL161ANSY or HL161ANQY(IgG1 null)
source                      1..450
                            mol_type = protein
                            organism = synthetic construct
SEQUENCE: 25
EVQLLESGGG LVQPGGSLRL SCAASEFTFG SYVMTWVRQA PGKGLEWVSV ISGSGGSTYY    60
ADSVKGRFTI SRDNSKNTLY LQMNSLRAED TAVYYCAKTP WWLRSPFFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG                                   450

SEQ ID NO: 26               moltype = AA  length = 450
FEATURE                     Location/Qualifiers
REGION                      1..450
                            note = HC of HL161ANSE or HL161ANQE(IgG1 null)
source                      1..450
                            mol_type = protein
                            organism = synthetic construct
SEQUENCE: 26
EVQLLESGGG LVQPGGSLRL SCAASEFTFG SSVMTWVRQA PGKGLEWVSV ISGSGGSTYY    60
ADSVKGRFTI SRDNSKNTLY LEMNSLRAED TAVYYCAKTP WWLRSPFFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG                                   450

SEQ ID NO: 27               moltype = AA  length = 450
FEATURE                     Location/Qualifiers
REGION                      1..450
                            note = HC of HL161ANSYE or HL161ANQYE(IgG1 null)
source                      1..450
                            mol_type = protein
                            organism = synthetic construct
SEQUENCE: 27
EVQLLESGGG LVQPGGSLRL SCAASEFTFG SYVMTWVRQA PGKGLEWVSV ISGSGGSTYY    60
ADSVKGRFTI SRDNSKNTLY LEMNSLRAED TAVYYCAKTP WWLRSPFFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG                                   450

SEQ ID NO: 28               moltype = DNA  length = 642
FEATURE                     Location/Qualifiers
misc_feature                1..642
                            note = Polynucleotide of HL161AN(IgG1 null) LC
source                      1..642
                            mol_type = other DNA
                            organism = synthetic construct
SEQUENCE: 28
tcttacgtgc tgacccagcc cccctccgtg tctgtggctc ctggccagac cgccagaatc    60
acctgtggcg gcaacaacat cggctccacc tccgtgcact ggtatcagca gaagcccggc   120
caggccccc tgctggtggt gcacgacgac tccgaccggc cttctggcat ccctgagcgg   180
ttctccggct ccaactccgg caacaccgcc accctgacca tctccagagt ggaagccggc   240
gacgaggccg actactactg ccaagtgcga gactcctcct ccgaccacgt gatcttcggc   300
ggaggcacca agctgaccgt gctgggccag cctaaggccg ctcccctccgt gacccctgttc   360
ccccatcct ccgaggaact gcaggccaac aaggccaact ggtctgcct gatctgcgac   420
ttctaccctg cgccgtgac cgtggcctgg aaggccgaca gctctcctgt gaaggccggc   480
gtggaaacca ccacccctc caagcagtcc aacaacaaat acgccgcctc ctcctacctg   540
tccctgaccc ccgagcagtg gaagtcccac cggtcctaca gctgccaagt gacacacgag   600
ggctccaccg tggaaaagac cgtggcccct accgagtgct cc                      642

SEQ ID NO: 29               moltype = DNA  length = 1407
FEATURE                     Location/Qualifiers
misc_feature                1..1407
                            note = Polynucleotide of HL161AN(IgG1 null) HC
source                      1..1407
                            mol_type = other DNA
                            organism = synthetic construct
SEQUENCE: 29
gaagtgcagc tgctggaatc cggcggaggc ctggtgcagc ctggcggctc tctgagactg    60
tcctgcgccg cctccgagtt caccttcggc agctgcgtga tgacctgggt ccgacaggct   120
```

```
cccggcaagg gcctggaatg ggtgtccgtg atctccggct ccggcggctc cacctactac  180
gccgactctg tgaagggccg gttcaccatc tcccgggaca actccaagaa cacccctgtac 240
ctgcagatga actccctgcg ggccgaggac accgccgtgt actactgcgc caagacccc   300
tggtggctgc ggtccccctt cttcgattac tggggccagg gcaccctggt gacagtgtcc  360
tccgcctcca ccaagggccc ctccgtgttc cctctggccc cctccagcaa gtccacctct  420
ggcggcaccg ctgccctggg ctgtctggtg aaagactact ccccgagcc cgtgaccgtg   480
tcctggaact ctggcgccct gacctccggc gtgcacacct tccctgccgt gctgcagtcc  540
tccggcctgt actccctgtc cagcgtggtg accgtgccct ccagctctct gggcacccag  600
acctacatct gcaacgtgaa ccacaagccc tccaacacca aggtggacaa gcgggtggaa  660
cccaagtcct gcgacaagac ccacacctgt cccccctgtc ctgcccctga agctgctggc  720
ggccctagcg tgttcctgtt ccccccaaag cccaaggaca ccctgatgat ctcccggacc  780
cccgaagtga cctgcgtggt ggtggacgtg tccacgagg accctgaagt gaagttcaat  840
tggtacgtgg acggcgtgga agtgcacaac gccaagacca gcccagaga ggaacagtac   900
aactccacct accgggtggt gtccgtgctg accgtgctgc accaggactg gctgaacggc  960
aaagagtaca agtgcaaggt ctccaacaag gccctgcctg cccccatcga aaagaccatc  1020
tccaaggcca agggccagcc ccgcgagccc caggtgtaca cactgccccc tagccgggaa  1080
gagatgacca agaaccaggt gtccctgaca tgctgtgta agggcttcta cccctccgac  1140
attgccgtgg aatgggagtc caacggccag cccgagaaca actacaagac caccccccct  1200
gtgctggact ccgacggctc attcttcctg tactccaagc tgaccgtgga caagtcccgg  1260
tggcagcagg gcaacgtgtt ctcctgctcc gtgatgcacg aggccctgca caaccactac  1320
acccagaagt ccctgtccct gagccccggc tgagtatact taattaactg ggcctcatgg  1380
gccttccgct cactgcccgc tttccag                                      1407

SEQ ID NO: 30           moltype = DNA   length = 645
FEATURE                 Location/Qualifiers
misc_feature            1..645
                        note = Polynucleotide of HL161ANS(IgG1 null) LC
source                  1..645
                        mol_type = other DNA
                        organism = synthetic construct
SEQUENCE: 30
tcttacgtgc tgacccagcc ccctccgtg tctgtggctc ctggccagac cgccagaatc   60
acctgtggcg gctcaaacat cggctccacc tccgtgcact ggtatcagca gaagcccggc  120
caggcccccg tgctggtggt gcacgacgac tccgaccggc cttctggcat ccctgagcgg  180
ttctccggct ccaactccgg caacaccgcc accctgacca tctccagagt ggaagccggc  240
gacgaggccg actactactg ccaagtgcga gactcctcct ccgaccacgt gatcttcggc  300
ggaggcacca agctgaccgt gctgggccag cctaaggccg ctccctccgt gaccctgttc  360
cccccatcct ccgaggaact gcaggccaac aaggccaccc tggtctgcct gatctccgac  420
ttctacccctg gcgccgtgac cgtggcctgg aaggccgaca gctctcctgt gaaggccggc  480
gtggaaacca ccacccccctc caagcagtcc aacaacaaat acgccgcctc ctcctacctg  540
tccctgaccc ccgagcagtg gaagtcccac cggtcctaca gctgccaagt gacacacgag  600
ggctccaccg tggaaaagac cgtggcccct accgagtgct cctga                 645

SEQ ID NO: 31           moltype = DNA   length = 1407
FEATURE                 Location/Qualifiers
misc_feature            1..1407
                        note = Polynucleotide of HL161ANS(IgG1 null) HC
source                  1..1407
                        mol_type = other DNA
                        organism = synthetic construct
SEQUENCE: 31
gaagtgcagc tgctggaatc cggcggaggc ctggtgcagc ctggcggctc tctgagactg   60
tcctgcgccg cctccgagtt caccttcggc agcagcgtga tgacctgggt ccgacaggct  120
cccggcaagg gcctggaatg ggtgtccgtg atctccggct ccggcggctc cacctactac  180
gccgactctg tgaagggccg gttcaccatc tcccgggaca actccaagaa cacccctgtac 240
ctgcagatga actccctgcg ggccgaggac accgccgtgt actactgcgc caagaccccc  300
tggtggctgc ggtccccctt cttcgattac tggggccagg gcaccctggt gacagtgtcc  360
tccgcctcca ccaagggccc ctccgtgttc cctctggccc cctccagcaa gtccacctct  420
ggcggcaccg ctgccctggg ctgtctggtg aaagactact ccccgagcc cgtgaccgtg   480
tcctggaact ctggcgccct gacctccggc gtgcacacct tccctgccgt gctgcagtcc  540
tccggcctgt actccctgtc ctccgtggtg accgtgccct ccagctctct gggcacccag  600
acctacatct gcaacgtgaa ccacaagccc tccaacacca aggtggacaa gcgggtggaa  660
cccaagtcct gcgacaagac ccacacctgt cccccctgtc ctgcccctga agctgctggc  720
ggccctagcg tgttcctgtt ccccccaaag cccaaggaca ccctgatgat ctcccggacc  780
cccgaagtga cctgcgtggt ggtggacgtg tccacgagg accctgaagt gaagttcaat  840
tggtacgtgg acggcgtgga agtgcacaac gccaagacca gcccagaga ggaacagtac   900
aactccacct accgggtggt gtctgtgctg accgtgctgc accaggactg gctgaacggc  960
aaagagtaca agtgcaaggt gtccaacaag gccctgcctg cccccatcga aaagaccatc  1020
tccaaggcca agggccagcc ccgcgagccc caggtgtaca cactgccccc tagccgggaa  1080
gagatgacca agaaccaggt gtccctgacc tgtctggtga aaggcttcta cccctccgac  1140
attgccgtgg aatgggagtc caacggccag cccgagaaca actacaagac cacccccct  1200
gtgctggact ccgacggctc attcttcctg tactccaagc tgaccgtgga caagtcccgg  1260
tggcagcagg gcaacgtgtt ctcctgctcc gtgatgcacg aggccctgca caaccactac  1320
acccagaagt ccctgtccct gagccccggc tgagtatact taattaactg ggcctcatgg  1380
gccttccgct cactgcccgc tttccag                                      1407

SEQ ID NO: 32           moltype = DNA   length = 645
FEATURE                 Location/Qualifiers
misc_feature            1..645
```

```
                        note = Polynucleotide of HL161ANS(IgG4) LC
source                  1..645
                        mol_type = other DNA
                        organism = synthetic construct
SEQUENCE: 32
tcttacgtgc tgacccagcc cccctccgtg tctgtggctc ctggccagac cgccagaatc    60
acctgtggcg gctcaaacat cggctccacc tccgtgcact ggtatcagca gaagcccggc   120
caggccccccg tgctggtggt gcacgacgac tccgaccggc cttctggcat ccctgagcgg  180
ttctccggct ccaactccgg caacaccgcc accctgacca tctccagagt ggaagccggc   240
gacgaggccg actactactg ccaagtgcga gactcctcct ccgaccacgt gatcttcggc   300
ggaggcacca agctgaccgt gctgggccag cctaaggccg ctcccctccgt gaccctgttc  360
ccccatcct ccgaggaact gcaggccaac aaggccaccc tggtctgcct gatctccgac    420
ttctaccctg gcgccgtgac cgtggcctgg aaggccgaca gctctcctgt gaaggccggc   480
gtggaaacca ccacccccctc caagcagtcc aacaacaaat acgccgcctc ctcctacctg  540
tccctgaccc ccgagcagtg gaagtcccac cggtcctaca gctgccaagt gacacacgag   600
ggctccaccg tggaaaagac cgtggcccct accgagtgct cctga                   645

SEQ ID NO: 33           moltype = DNA   length = 1347
FEATURE                 Location/Qualifiers
misc_feature            1..1347
                        note = Polynucleotide of HL161ANS(IgG4) HC
source                  1..1347
                        mol_type = other DNA
                        organism = synthetic construct
SEQUENCE: 33
gaagttcagc tgttggagtc tggcggcgga ttggttcaac ctggcggatc tctgagactg    60
tcttgcgccg cctctgagtt caccttcggc tcctctgtga tgacctgggt ccgacaggct   120
cctggcaaag gactggaatg ggtgtccgtg atctctggct ctggcggctc tacctactac   180
gccgattctg tgaagggcag attcaccatc agccgggaca actccaagaa caccctgtac   240
ctgcagatga actccctgag agccgaggac accgccgtgt actattgtgc taagacccct   300
tggtggctgc ggtccccttt cttttgattat tggggccagg gcaccctggt caccgtgtcc   360
tctgcttcta caaagggccc ctctgtgttc cctctggctc cttgctctag atccacctcc   420
gagtctaccc tgctctgggc tgtctggtca aggactact tccctgagcc tgtgaccgtg    480
tcttggaact ctggtgctct gacctccgga gtgcacacat ttccagctgt gctgcagtcc   540
tccggcctgt actctctgtc tctgtcgtg accgtgcctt ctagctctct gggcaccaag   600
acctacacct gtaacgtgga ccacaagcct tccaacacca aggtggacaa gcgcgtggaa   660
tctaagtacg gcccctcttg tcctccatgt cctgctccag aattcctcgg cggaccctcc   720
gtgttcctgt ttcctccaaa gcctaaggac accctgatga tctctcggac ccctgaagtg   780
acctgcgtgg tggtggatgt gtctcaagag gaccccgagg tgcagttcaa ttggtacgtg   840
gacggcgtgg aagtgcacaa cgccaagacc aagcctagag aggaacagtt caactccacc   900
tacagagtgg tgtctgtgct gaccgtgctg caccaggatt ggctgaacgg caaagagtac   960
aagtgcaagg tgtccaacaa gggcctgcct tccagcatcg aaaagaccat ctccaaggct  1020
aagggccagc ctcgggaacc tcaggtttac acctgcctc caagccaaga ggaaatgacc  1080
aagaaccagg tgtccctgac ctgcctcgtg aagggcttct acccttccga cattgccgtg   1140
gaatgggagt ctaacggcca gccagagaac aactacaaga caccccctcc tgtgctggac  1200
tccgacggcc ttttcttcct gtattctcgc ctgaccgtgg acaagtctcg gtggcaagag  1260
ggcaacgtgt tctcctgttc tgtgatgcac gaggccctgc acaaccacta cacccagaag  1320
tccctgtctc tgtccctggg ctaatga                                      1347

SEQ ID NO: 34           moltype = DNA   length = 645
FEATURE                 Location/Qualifiers
misc_feature            1..645
                        note = Polynucleotide of HL161ANQ(IgG1 null) LC
source                  1..645
                        mol_type = other DNA
                        organism = synthetic construct
SEQUENCE: 34
tcttacgtgc tgacccagcc cccctccgtg tctgtggctc ctggccagac cgccagaatc    60
acctgtggcg gccagaacat cggctccacc tccgtgcact ggtatcagca gaagcccggc   120
caggccccccg tgctggtggt gcacgacgac tccgaccggc cttctggcat ccctgagcgg  180
ttctccggct ccaactccgg caacaccgcc accctgacca tctccagagt ggaagccggc   240
gacgaggccg actactactg ccaagtgcga gactcctcct ccgaccacgt gatcttcggc   300
ggaggcacca agctgaccgt gctgggccag cctaaggccg ctcccctccgt gaccctgttc  360
ccccatcct ccgaggaact gcaggccaac aaggccaccc tggtctgcct gatctccgac    420
ttctaccctg gcgccgtgac cgtggcctgg aaggccgaca gctctcctgt gaaggccggc   480
gtggaaacca ccacccccctc caagcagtcc aacaacaaat acgccgcctc ctcctacctg  540
tccctgaccc ccgagcagtg gaagtcccac cggtcctaca gctgccaagt gacacacgag   600
ggctccaccg tggaaaagac cgtggcccct accgagtgct cctga                   645

SEQ ID NO: 35           moltype = DNA   length = 1407
FEATURE                 Location/Qualifiers
misc_feature            1..1407
                        note = Polynucleotide of HL161ANQ(IgG1 null) HC
source                  1..1407
                        mol_type = other DNA
                        organism = synthetic construct
SEQUENCE: 35
gaagtgcagc tgctggaatc cggcggaggc ctggtgcagc tggcggctc tctgagactg     60
tcctgcgccg cctccgagtt caccttcggc agcagcgtga tgacctgggt ccgacaggct  120
```

-continued

```
cccggcaagg gcctggaatg ggtgtccgtg atctccggct ccggcggctc cacctactac    180
gccgactctg tgaagggccg gttcaccatc tcccgggaca actccaagaa cacccctgtac   240
ctgcagatga actccctgcg ggccgaggac accgccgtgt actactgcgc caagacccccc  300
tggtggctgc ggtcccccctt cttcgattac tggggccagg gcaccctggt gacagtgtcc   360
tccgcctcca ccaagggccc ctccgtgttc cctctcgtgcc cctccagcaa gtccacctct   420
ggcggcaccg ctgccctggg ctgcctggtg aaagactact tccccgagcc cgtgaccgtg    480
tcctggaact ctggcgccct gacctccggc gtgcacacct ccctgcctt gctgcagtcc    540
tccggcctgt actccctgtc ctccgtggtg accgtgccct ccagctctct gggcacccag    600
acctacatct gcaacgtgaa ccacaagccc tccaacacca aggtggacaa gcgggtggaa    660
cccaagtcct gcgacaagac ccacacctgt cccccctgtc ctgcccctga agctgctggc    720
ggccctagcg tgttcctgtt cccccccaaag cccaaggaca ccctgatgat ctcccggacc    780
cccgaagtga cctgcgtggt ggtggacgtg tcccacgagg accctgaagt gaagttcaat    840
tggtacgtgg acggcgtgga agtgcacaac gccaagacca agcccagaga ggaacagtac    900
aactccacct accgggtggt gtctgtgctg accgtgctgc accaggactg gctgaacggc    960
aaagagtaca agtgcaaggt gtccaacaag gccctgcctg cccccatcga aagaccatc     1020
tccaaggcca agggccagcc ccgcgagccc caggtgtaca cactgccccc tagccgggaa   1080
gagatgacca gaaccaggt gtccctgacc tgtctggtga aaggcttcta cccctccgac    1140
attgccgtgg aatgggagtc caacggccag ccgagaaca actacaagac cacccccccct  1200
gtgctggact ccgacggctc attcttcctg tactccaagc tgaccgtgga caagtcccgg    1260
tggcagcagg gcaacgtgtt cctgctctcc gtgatgcacg aggccctgca caaccactac    1320
acccagaagt ccctgtccct gagccccggc tgagtatact taattaactg gcctcatgg    1380
gccttccgct cactgcccgc tttccag                                        1407

SEQ ID NO: 36         moltype = DNA  length = 645
FEATURE               Location/Qualifiers
misc_feature          1..645
                      note = Polynucleotide of HL161ANQ(IgG4) LC
source                1..645
                      mol_type = other DNA
                      organism = synthetic construct
SEQUENCE: 36
tcttacgtgc tgacccagcc ccctccgtg tctgtggctc ctggccagac cgccagaatc      60
acctgtggcg ccagaacat cggctccacc tccgtgcact ggtatcagca gaagcccggc    120
caggccccg tgctggtggt gcacgacgac tccgaccggc cttctggcat ccctgagcgg    180
ttctccggct ccaactccgg caacaccgcc accctgacca tctccagagt ggaagccggc    240
gacgaggccg actactactg ccaagtgcga gactcctcc ccgaccacgt gatcttcggc     300
ggaggcacca agctgaccgt gctgggccag cctaaggccg ctccctccgt gacccctgttc   360
cccccatcct ccgaggaact gcaggccaac aaggccaccc tggtctgcct gatctccgac    420
ttctacccctg gcgccgtgac cgtggcctgg aaggccgaca gctctcctgt gaaggccggc    480
gtggaaacca ccaccccctc caagcagtcc aacaacaaat acgccgcctc ctcctactg    540
tccctgaccc ccgagcagtg gaagtccac cggtcctaca gctgccaagt gacacacgag    600
ggctccaccg tggaaaagac cgtggccct accgagtgct cctga                    645

SEQ ID NO: 37         moltype = DNA  length = 1347
FEATURE               Location/Qualifiers
misc_feature          1..1347
                      note = Polynucleotide of HL161ANQ(IgG4) HC
source                1..1347
                      mol_type = other DNA
                      organism = synthetic construct
SEQUENCE: 37
gaagttcagc tgttggagtc tggcggcgga ttggttcaac ctggcggatc tctgagactg     60
tcttgcgccg cctctgagtt caccttcggc tcctctgtga tgacctgggt ccgacaggct    120
cctggcaaag gactggaatg ggtgtccgtg atctctggct ctggcggctc tacctactac    180
gccgattctg tgaagggcag attcaccatc agccgggaca actccaagaa cacccctgtac   240
ctgcagatga actccctgag agccgaggac accgccgtgt actattgtgc taagaccccct   300
tggtggctgc ggtcccccctt ctttgattat tggggccagg gcaccctggt caccgtgtcc   360
tctgcttcta caaagggccc ctctgtgttc cctctggctc cttgtctag atccacctcc    420
gagtctaccg ctgctctggg ctgtctggtc aaggactact tcctgagcc tgtgaccgtg    480
tcttggaact ctggtgctct gacctccggc gtgcacacat tccagtcgtg tgctgcagtcc  540
tccggcctgt actctctgtc ctctgtcgtg accgtgcctt ctagctctct gggcaccaag    600
acctacacct gtaacgtgga ccacaagcct tccaacacca aggtggacaa gcgcgtggaa    660
tctaagtacg gccctccttg tcctccatgt cctgctccag aattcctcgg cggaccctcc    720
gtgttcctgt ttcctccaaa gcctaaggac accctgatga tctctcggac ccctgaagtg    780
acctgcgtgg tggtggatgt gtctcaagag accccgagg tgcagttcaa ttggtacgtg    840
gacggcgtgg aagtgcacaa cgccaagacc aagcctagag gaacagtt caactccacc    900
tacagagtgg tgtctgtgct gaccgtgctg caccaggatt ggctgaacgg caaagagtac    960
aagtgcaagg tgtccaacaa gggcctgcct tccagcatcg aaaagaccat ctccaaggct   1020
aagggccagc ctcgggaacc tcaggtttac accctgcctc caagccaaga ggaaatgacc    1080
aagaaccagg tgtccctgac ctgcctcgtg aagggcttct acccttccga cattgccgtg    1140
gaatgggagt ctaacggcca gccagagaac aactacaaga caccctctcc tgtgctggac    1200
tccgacggct cttttcttcct gtattctcgc ctgaccgtgg acaagtctcg gtggcaagag   1260
ggcaacgtgt tctctgttc tgtgatgcac gaggccctgc acaaccacta cacccagaag   1320
tccctgtctc tgtccctggg ctaatga                                       1347
```

ANTI-FcRn ANTIBODY OR ANTIGEN BINDING FRAGMENT THEREOF WITH IMPROVED STABILITY

CROSS-REFERENCE TO RELATED APPLICATIONS

This application is a continuation of PCT/US2023/067539 filed May 26, 2023 which claims the benefit of Korean Application No. 10-2022-0066176 filed May 30, 2022, U.S. Provisional Patent Applications No. 63/352,948, filed Jun. 16, 2022, No. 63/370,772, filed Aug. 8, 2022, No. 63/377,283, filed Sep. 27, 2022, and No. 63/499,116 filed Apr. 28, 2023, each of which is incorporated herein by reference in its entirety.

INCORPORATION-BY-REFERENCE OF SEQUENCE LISTING

10021 The contents of the electronic sequence listing (MUNO_008_N01US_SeqList_ST26.xml; Size: 61,491 bytes; and Date of Creation: Jun. 23, 2023) are hereby incorporated by reference herein in their entirety.

TECHNICAL FIELD

The present invention relates to an anti-FcRn antibody or an antigen binding fragment thereof with improved stability and uses thereof.

BACKGROUND ART

The causes of autoimmune diseases have been studied for a long time from genetic, environmental and immunological perspectives, but the exact cause of the disease is still unknown. Many recent studies have revealed that a number of autoimmune diseases are caused by IgG-type autoantibodies. In fact, in studies for the diagnosis and treatment of autoimmune diseases, the relationship between the presence, absence, or reduction of disease-specific autoantibodies and the therapeutic effect thereof has been widely investigated.

As a therapeutic agent for such autoimmune diseases, the first-line agent is a systemic high-dose steroid injection, and when symptoms are serious or difficult to control with steroids, high-dose IVIG (intravenous immunoglobulin) administration or plasmapheresis is applied. High-dose steroid may have a weak effect or have serious side effects when repeatedly used. In the case of IVIG and plasmapheresis, the cost of treatment is high and there are various side effects and risks of infection, so the development of a therapeutic agent in this treatment field is urgently needed.

On the other hand, recently, a therapeutic agent for autoimmune diseases using an FcRn antibody is being studied (Korean Patent No. 10-1815265). It is a drug with a new mechanism, in which the antibody blocks FcRn (neonatal Fc receptor), which is involved in the recycling of IgG, and increases the catabolism of IgG in the body, thereby lowering the levels of autoantibodies to treat the diseases. This anti-FcRn antibody is expected as a product that can solve the problems of existing therapeutic agents.

However, in order to apply this antibody to severe autoimmune diseases such as pemphigus or neuromyelitis, which are caused by the generation of an autoantibody against an autoantigen in the body, it is necessary to develop an antibody with stability while maintaining the affinity and biological activity of the existing antibody.

PRIOR ART DOCUMENT

Patent Document (Patent Document 1) KR 10-1815265 B

DISCLOSURE OF INVENTION

Technical Problem

Accordingly, the present inventors produced variants of the anti-FcRn antibody with improved stability by significantly reducing the production rate of aggregates while maintaining the affinity and biological activity of the previously developed anti-FcRn antibody HL161AN, thereby completing the present invention.

SUMMARY

In an aspect of the present invention, there is provided an anti-FcRn antibody or an antigen binding fragment thereof comprising a light chain variable region comprising LCDR1 comprising the amino acid sequence of SEQ ID NO: 1, LCDR2 comprising the amino acid sequence of SEQ ID NO: 2, and LCDR3 comprising the amino acid sequence of SEQ ID NO: 3; and a heavy chain variable region comprising HCDR1 comprising the amino acid sequence of SEQ ID NO: 5, HCDR2 comprising the amino acid sequence of SEQ ID NO: 6, and HCDR3 comprising the amino acid sequence of SEQ ID NO: 7, wherein the amino acid of N3 in the amino acid sequence of SEQ ID NO: 1 is substituted with another amino acid, or the amino acid of C2 in the amino acid sequence of SEQ ID NO: 5 is substituted with another amino acid. In some embodiments, the amino acid of N3 in the amino acid sequence of SEQ ID NO: 1 is substituted with Ser (S) or Gln (Q). In some embodiments, the amino acid of C2 in the amino acid sequence of SEQ ID NO: 5 is substituted with Ser (S) or Tyr (Y).

In another aspect of the present invention, there is provided an anti-FcRn antibody or an antigen binding fragment thereof comprising a light chain variable region comprising the amino acid sequence of SEQ ID NO: 4 and a heavy chain variable region comprising the amino acid sequence of SEQ ID NO: 8, wherein the amino acid of N25 in the amino acid sequence of SEQ ID NO: 4 is substituted with another amino acid, and the amino acid of C32 or Q82 in the amino acid sequence of SEQ ID NO: 8 is substituted with another amino acid. In some embodiments, the amino acid of N25 in the amino acid sequence of SEQ ID NO: 4 is substituted with Ser (S) or Gln (Q). In some embodiments, the amino acid of C32 in the amino acid sequence of SEQ ID NO: 8 is substituted with Ser (S) or Tyr (Y). In some embodiments, the amino acid of Q82 in the amino acid sequence of SEQ ID NO: 8 may be substituted with Glu (E), but is not limited thereto.

In some embodiments, the anti-FcRn antibody or antigen binding fragment provided herein comprises a heavy chain variable region comprising a framework composed of framework region 1 (FR1) of the amino acid sequence of SEQ ID NO: 15, FR2 of the amino acid sequence of SEQ ID NO: 16, FR3 of the amino acid sequence of SEQ ID NO: 17, and FR4 of the amino acid sequence of SEQ ID NO: 18. In some embodiments, the amino acid of Q16 in the amino acid sequence of SEQ ID NO: 17 is substituted with another amino acid. In some embodiments, the amino acid of Q16 in the amino acid sequence of SEQ ID NO: 17 is substituted with Glu (E).

In some embodiments, there is provided an anti-FcRn antibody or an antigen binding fragment thereof comprising: a light chain variable region comprising LCDR1 comprising the amino acid sequence of SEQ ID NO: 9, LCDR2 comprising the amino acid sequence of SEQ ID NO: 2, and LCDR3 comprising the amino acid sequence of SEQ ID NO: 3; and a heavy chain variable region comprising HCDR1 comprising the amino acid sequence of SEQ ID NO: 11, HCDR2 comprising the amino acid sequence of SEQ ID NO: 6, and HCDR3 comprising the amino acid sequence of SEQ ID NO: 7.

In some embodiments, the anti-FcRn antibody comprises an Fc region, wherein the Fc region is an IgG1 Fc region or an IgG4 Fc region. In some embodiments, the Fc region is an IgG1 Fc region comprising Leu234Ala and Leu235Ala amino acid substitutions. In some embodiments, the Fc region is an IgG4 Fc region comprising an S228P mutation.

In another aspect of the present invention, there is provided a polynucleotide encoding the anti-FcRn antibody or antigen binding fragment thereof.

In another aspect of the present invention, there is provided a recombinant expression vector comprising the polynucleotide.

In another aspect of the present invention, there is provided a host cell transformed with the recombinant expression vector.

In another aspect of the present invention, there is provided a method for producing an anti-FcRn antibody or an antigen binding fragment thereof, comprising culturing the host cell to produce an antibody; and isolating and purifying the produced antibody to recover an antibody that specifically binds to FcRn.

In another aspect of the present invention, there is provided a pharmaceutical composition for treating an autoimmune disease, comprising the anti-FcRn antibody or antigen binding fragment thereof. In some embodiments, the autoimmune disease is one selected from the group consisting of: autoimmune neutropenia, Guillain-Barre syndrome, epilepsy, autoimmune encephalitis, Isaacs' syndrome, nevus syndrome, pemphigus vulgaris, deciduous pemphigus, bullous pemphigoid, acquired epidermolysis bullosa, gestational pemphigoid, mucous membrane pemphigoid, antiphospholipid syndrome, autoimmune anemia, autoimmune Graves' disease, thyroid eye disease (TED), Goodpasture syndrome, myasthenia gravis, multiple sclerosis, rheumatoid arthritis, lupus, idiopathic thrombocytopenic purpura (ITP), warm autoimmune hemolytic anemia (WAIHA), chronic inflammatory demyelinating polyneuropathy (CIDP), lupus nephritis, IgA nephropathy (Berger's Disease), dermatomyositis, necrotizing autoimmune myopathy, and membranous nephropathy.

In another aspect of the present invention, there is provided a method of treating an autoimmune disease in a subject in need thereof, comprising administering to the subject the anti-FcRn antibody or antigen binding fragment thereof or the pharmaceutical composition. In some embodiments, the subject is human. In some embodiments, the autoimmune disease is selected from the group consisting of: autoimmune neutropenia, Guillain-Barre syndrome, epilepsy, autoimmune encephalitis, Isaacs' syndrome, nevus syndrome, pemphigus vulgaris, deciduous pemphigus, bullous pemphigoid, acquired epidermolysis bullosa, gestational pemphigoid, mucous membrane pemphigoid, antiphospholipid syndrome, autoimmune anemia, autoimmune Graves' disease, Goodpasture syndrome, myasthenia gravis, multiple sclerosis, rheumatoid arthritis, lupus, idiopathic thrombocytopenic purpura (ITP), lupus nephritis, and membranous nephropathy.

In some embodiments, the administering is parenteral. In some embodiments, the administering is subcutaneous or intravenous. In some embodiments, the administering is at a dose from 300 mg to 2400 mg. In some embodiments, the administering is once weekly, once in two weeks, once in three weeks or once monthly. In some embodiments, the administering is subcutaneous once weekly at a dose from 300 mg to 900 mg. In some embodiments, the administering is subcutaneous once in two weeks at a dose from 300 mg to 1800 mg. In some embodiments, the administering does not result in more than 5% or more than 10% decrease in blood albumin levels in the subject compared to the blood albumin levels prior to the administration of the anti-FcRn antibody or antigen-binding fragment.

In some embodiments, the administering does not result in more than 5% or more than 10% increase in blood total cholesterol or low-density lipoprotein (LDL) levels in the subject compared to the blood total cholesterol or LDL levels prior to the administration of the anti-FcRn antibody or antigen-binding fragment.

Effects of Invention

The FcRn specific antibody according to the present invention has improved stability, such as reducing the production rate of aggregates, while having excellent productivity and biological activity compared to the parent antibody, HL161AN. The antibody of the present invention not only has high affinity for FcRn, but also has or is predicted to have high specificity and no or low immunogenicity, and it binds to FcRn to significantly reduce the amount of pathogenic autoantibodies in the blood. Therefore, it can be utilized for the treatment of an autoimmune disease.

BRIEF DESCRIPTION OF DRAWINGS

FIG. 3 is a drawing showing the predicted post-translational modification (PTM) site of the HL161AN heavy chain (SEQ ID NO: 20).

FIG. 5 is a drawing showing the results of the in silico design of the HL161AN variant (top) and the analysis results of the paratope of HL161AN for human FcRn (bottom, light chain: SEQ ID NO: 19, heavy chain: SEQ ID NO: 20). Specifically, it shows the results of designing the variant by engineering the three amino acid (L:Asn25, H:Cys32, H:Gln82) sites that can affect the stability of the HL161AN antibody. Here, the ellipse indicates the substitution site of the selected PTM site. In addition, the paratope of HL161AN is indicated in bold letters, and the CDR region according to the IgBlast Kabat system is indicated by underlining* indicates the substitution site of the selected amino acid.

DETAILED DESCRIPTION FOR CARRYING OUT THE INVENTION

Figure 1:
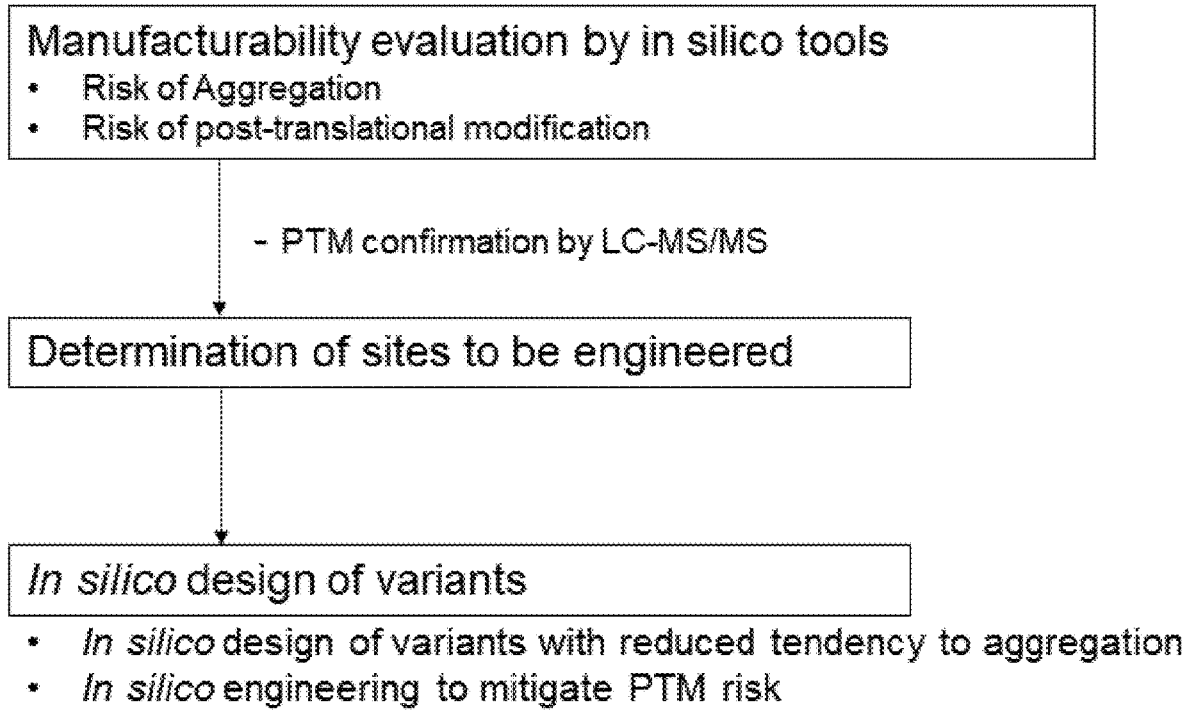

Anti-FcRn Antibody Variant or Antigen Binding Fragment Thereof

In an aspect of the present invention, there is provided an anti-FcRn antibody or an antigen binding fragment thereof with improved stability, comprising a light chain variable region comprising LCDR1 comprising the amino acid sequence of SEQ ID NO: 1, LCDR2 comprising the amino acid sequence of SEQ ID NO: 2, and LCDR3 comprising the amino acid sequence of SEQ ID NO: 3; and a heavy chain variable region comprising HCDR1 comprising the amino acid sequence of SEQ ID NO: 5, HCDR2 comprising the amino acid sequence of SEQ ID NO: 6, and HCDR3 comprising the amino acid sequence of SEQ ID NO: 7.

Then, the amino acid of N3 in the amino acid sequence of SEQ ID NO: 1 may be substituted with another amino acid, or the amino acid of C2 in the amino acid sequence of SEQ ID NO: 5 may be substituted with another amino acid. "The amino acid of N3 in the amino acid sequence of SEQ ID NO: 1" refers to the amino acid (Asparagine) in position 3 of SEQ ID NO: 1; and "the amino acid of C2 in the amino acid sequence of SEQ ID NO: 5" refers to the amino acid (Cysteine) in position 2 of SEQ ID NO:5.

As used herein, the term "FcRn" or "neonatal Fc receptor" is an MHC class I related protein that is expressed in vascular endothelial cells and binds to IgG and albumin. A characteristic feature is that the binding between IgG and FcRn is strong when the pH is weakly acidic, and there is no binding force at neutral pH. Therefore, IgG that enters cells by pinocytosis or endocytosis binds strongly to FcRn, a type of Fc gamma receptor (FcγR), in endosomes under pH 6.0 conditions, and thus may avoid the degradative lysosome pathway. Upon recycling back to the cell membrane, IgG rapidly dissociates from FcRn in the bloodstream at pH 7.4. It is known that by this receptor mediated recycling mechanism, FcRn effectively blocks the degradation of IgG in lysosomes, thereby prolonging the half-life of IgG. That is, FcRn binds to an antibody of the IgG isotype and acts as a receptor to recover the antibody, thereby playing an important role in maintaining the antibody level in serum.

On the other hand, it has been suggested that autoimmune diseases caused by autoantibodies may be treated by reducing the serum half-life of IgG by inhibiting binding of IgG to FcRn (Li et al., *J. Clin. Invest.*, 115:3440, 2005).

As used herein, the term "anti-FcRn antibody" is used interchangeably with "anti-FcRn antibody variant," and is an antibody specific for FcRn. The antibody includes an intact antibody form as well as an antigen binding fragment of an antibody.

In general, antibody molecules obtained from humans relate to any of the classes of immunoglobulin (IgG, IgM, IgA, IgE and IgD), which differ from one another by the nature of the heavy chain present in the molecule. Certain classes have subclasses as well, such as IgG1, IgG2, IgG3, or IgG4, and others. Furthermore, in humans, the light chain may be a kappa chain or a lambda chain. Accordingly, in one embodiment, the antibody disclosed herein is a human IgG antibody. In some embodiments, the antibody is an IgG1 antibody. In some embodiments, the antibody is an IgG4 antibody. In some embodiments, an anti-FcRn antibody described herein is a synthetic antibody based on protein scaffolds, which have the ability to bind to FcRn.

In some embodiments, the anti-FcRn antibody is a monoclonal antibody. The term "monoclonal antibody" (MAb or mAb) or "monoclonal antibody composition", as used herein, refers to a population of antibody molecules that contain only one molecular species of antibody molecule consisting of a unique light chain gene product and a unique heavy chain gene product.

As used herein, the term "antigen binding fragment" refers to one or more fragments of an intact antibody that retain the ability to specifically bind to a given antigen, i.e., FcRn. A fragment of the antibody in the present invention includes single-chain antibodies, bispecific antibodies, trispecific antibodies, multispecific antibodies such as diabodies, triabodies, and tetrabodies, Fab fragments, F(ab')$_2$ fragments, Fd, scFv, domain antibodies, dual-specific antibodies, minibodies, scap (sterol regulatory binding protein cleavage activating protein), chelating recombinant antibodies, tribodies, bibodies, intrabodies, nanobodies, SMIP (small modular immunopharmaceuticals), binding domain immunoglobulin fusion proteins, camelized antibodies, VHH-containing antibodies, antibody constant region derivatives, but is not limited thereto.

An anti-FcRn antibody or antigen-binding fragment provided herein may be a humanized antibody, a human antibody, a chimeric antibody, or a murine antibody.

It will be apparent to one of ordinary skill in the art that as long as the binding function to FcRn is maintained, any type of fragment of the antibody according to the present disclosure will exhibit the same properties as the antibody according to the present disclosure.

Exemplary CDR sequences of anti-FcRn antibodies disclosed herein are set forth in Table 1. The CDRs are defined according to the Kabat system.

TABLE 1

|  |  | CDR1 | CDR2 | CDR3 |
|---|---|---|---|---|
| HL 161 AN | VL | GGNNI GSTSVH (SEQ ID NO: 1) | DDSDRPS (SEQ ID NO: 2) | QVRDSS SDHVI (SEQ ID NO: 3) |
|  | VH | SCVMT (SEQ ID NO: 5) | VISGSGG STYYADS VKG (SEQ ID NO: 6) | TPWWLRS PFFDY (SEQ ID NO: 7) |
| HL 161 ANS | VL | GGSNI GSTSVH (SEQ ID NO: 9) | DDSDRPS (SEQ ID NO: 2) | QVRDS SSDHVI (SEQ ID NO: 3) |
|  | VH | SSVMT (SEQ ID NO: 11) | VISGSG GSTYYA DSVKG (SEQ ID NO: 6) | TPWWLR SPFFDY (SEQ ID NO: 7) |
| HL 161 ANQ | VL | GGQNI GSTSVH (SEQ ID NO: 13) | DDSDRPS (SEQ ID NO: 2) | QVRDSS SDHVI (SEQ ID NO: 3) |
|  | VH | SSVMT (SEQ ID NO: 11) | VISGSG GSTYYA DSVKG (SEQ ID NO: 6) | TPWWLR SPFFDY (SEQ ID NO: 7) |

In one embodiment, the anti-FcRn antibody or antigen binding fragment thereof comprises a light chain variable region comprising LCDR1 comprising the amino acid sequence of SEQ ID NO: 1, LCDR2 comprising the amino acid sequence of SEQ ID NO: 2, and LCDR3 comprising the amino acid sequence of SEQ ID NO: 3; and a heavy chain variable region comprising HCDR1 comprising the amino acid sequence of SEQ ID NO: 5, HCDR2 comprising the amino acid sequence of SEQ ID NO: 6, and HCDR3 comprising the amino acid sequence of SEQ ID NO: 7, wherein the amino acid of N3 in the amino acid sequence of SEQ ID NO: 1 may be substituted with another amino acid, or the amino acid of C2 in the amino acid sequence of SEQ ID NO: 5 may be substituted with another amino acid.

As used herein, the term "heavy chain (HC)" refers to both a full length heavy chain comprising a variable region domain VH comprising an amino acid sequence having a sufficient variable region sequence to confer specificity to an antigen and three constant region domains CH1, CH2 and CH3, and a fragment thereof. In addition, as used herein, the term "light chain (LC)" refers to both a full length light chain comprising a variable region domain VL comprising an amino acid sequence having a sufficient variable region sequence to confer specificity to an antigen and a constant region domain CL, and a fragment thereof.

As used herein, the term "variable" indicates that a specific portion of a variable region is significantly different in sequence between antibodies. The V region mediates antigen binding and defines the specificity of a particular antibody for its particular antigen. Variability is concentrated in three segments called hypervariable regions (HVRs), i.e., CDRs, in both the light and heavy chain variable regions. The more highly conserved portions of the variable regions are called framework (FR) regions. The heavy and light chain variable regions have FR1, CDR1, FR2, CDR2, FR3, CDR3, and FR4 structures from N-terminus to C-terminus.

As used herein, the term "CDR (complementarity determining region)" refers to an amino acid sequence of a hypervariable region of immunoglobulin heavy and light chains. The heavy chain (HCDR1, HCDR2 and HCDR3) and light chain (LCDR1, LCDR2 and LCDR3) each contain three CDRs. CDRs provide key contact residues for binding of an antibody to an antigen or epitope.

As used herein, the term "substitution with another amino acid" refers to a substitution with another amino acid residue having properties similar to the original amino acid sequence. It is not particularly limited as long as the properties of the antibody according to the present disclosure are maintained even if the amino acid substitution occurs. The "amino acid" introduced by the above substitution may be any one selected from the group consisting of lysine (K), alanine (A), arginine (R), asparagine (N), aspartic acid (D), cysteine (C), glutamine (Q), glutamic acid (E), glycine (G), histidine (H), isoleucine (I), leucine (L), methionine (M), phenylalanine (F), proline (P), serine (S), threonine (T), tryptophan (W), tyrosine (Y), and valine (V). Substitutions may be described as, for example, "the amino acid of N3 in the amino acid sequence of SEQ ID NO: 1," which refers to the N in position 3 of SEQ ID NO: 1.

In one embodiment, the amino acid of N3 in the amino acid sequence of SEQ ID NO: 1 may be substituted with Ser (S) or Gln (Q), but is not limited thereto.

In one embodiment, the amino acid of C2 in the amino acid sequence of SEQ ID NO: 5 may be substituted with Ser (S) or Tyr (Y), but is not limited thereto.

In one embodiment, variant No. 1 may comprise a light chain variable region comprising LCDR1 comprising the amino acid sequence of SEQ ID NO: 9, LCDR2 comprising the amino acid sequence of SEQ ID NO: 2, and LCDR3 comprising the amino acid sequence of SEQ ID NO: 3; and a heavy chain variable region comprising HCDR1 comprising the amino acid sequence of SEQ ID NO: 11, HCDR2 comprising the amino acid sequence of SEQ ID NO: 6, and HCDR3 comprising the amino acid sequence of SEQ ID NO: 7. In this regard, the Fc region of the antibody may be IgG1 or a variant thereof, IgG4 or a variant thereof. The variant No. 1 may be denoted as HL161ANS, HL161ANS (IgG1null) or HL161ANS (IgG4).

In one embodiment, variant No. 12 may comprise a light chain variable region comprising LCDR1 comprising the amino acid sequence of SEQ ID NO: 13, LCDR2 comprising the amino acid sequence of SEQ ID NO: 2, and LCDR3 comprising the amino acid sequence of SEQ ID NO: 3; and a heavy chain variable region comprising HCDR1 comprising the amino acid sequence of SEQ ID NO: 11, HCDR2 comprising the amino acid sequence of SEQ ID NO: 6, and HCDR3 comprising the amino acid sequence of SEQ ID NO: 7. In this regard, the Fc region of the antibody may be IgG1 or a variant thereof, IgG4 or a variant thereof. The variant No. 12 may be denoted as HL161ANQ, HL161ANQ (IgG1null) or HL161ANQ (IgG4).

In one embodiment, variant No. 2 may comprise a light chain variable region comprising LCDR1 comprising an amino acid sequence in which the amino acid of N3 in the amino acid sequence of SEQ ID NO: 1 is substituted with Ser (S), LCDR2 comprising the amino acid sequence of SEQ ID NO: 2, and LCDR3 comprising the amino acid sequence of SEQ ID NO: 3; and a heavy chain variable region comprising HCDR1 comprising an amino acid sequence in which the amino acid of C2 in the amino acid sequence of SEQ ID NO: 5 is substituted with Tyr (Y), HCDR2 comprising the amino acid sequence of SEQ ID NO: 6, and HCDR3 comprising the amino acid sequence of SEQ ID NO: 7. In this regard, the Fc region of the antibody may be IgG1 or a variant thereof, IgG4 or a variant thereof. The variant No. 2 may be denoted as HL161ANSY, HL161ANSY (IgG1null) or HL161ANSY (IgG4).

In one embodiment, variant No. 13 may comprise a light chain variable region comprising LCDR1 comprising an amino acid sequence in which the amino acid of N3 in the amino acid sequence of SEQ ID NO: 1 is substituted with Gln (Q), LCDR2 comprising the amino acid sequence of SEQ ID NO: 2, and LCDR3 comprising the amino acid sequence of SEQ ID NO: 3; and a heavy chain variable region comprising HCDR1 comprising an amino acid sequence in which the amino acid of C2 in the amino acid sequence of SEQ ID NO: 5 is substituted with Tyr (Y), HCDR2 comprising the amino acid sequence of SEQ ID NO: 6, and HCDR3 comprising the amino acid sequence of SEQ ID NO: 7. In this regard, the Fc region of the antibody may be IgG1 or a variant thereof, IgG4 or a variant thereof. The variant No. 13 may be denoted as HL161ANQY, HL161ANQY (IgG1null) or HL161ANQY (IgG4).

In one embodiment, variant No. 23 may comprise a light chain variable region comprising LCDR1 comprising an amino acid sequence in which the amino acid of N3 in the amino acid sequence of SEQ ID NO: 1 is substituted with Ser (S), LCDR2 comprising the amino acid sequence of SEQ ID NO: 2, and LCDR3 comprising the amino acid sequence of SEQ ID NO: 3; and a heavy chain variable region comprising HCDR1 comprising an amino acid sequence in which the amino acid of C2 in the amino acid sequence of SEQ ID NO: 5 is substituted with Tyr (Y), HCDR2 comprising the amino acid sequence of SEQ ID NO: 6, and HCDR3 comprising the amino acid sequence of SEQ ID NO: 7. In this regard, the Fc region of the antibody may be IgG1 or a variant thereof, IgG4 or a variant thereof. The variant No. 23 may be denoted as HL161ANSY, HL161ANSY (IgG1null) or HL161ANSY (IgG4).

In some embodiments, an anti-FcRn antibody or antigen-binding fragment thereof comprises a VL CDR1 comprising the sequence GGX$_1$NIGSTSV (SEQ ID NO: 38), wherein X$_1$ is N, S or Q. In some embodiments, an anti-FcRn antibody or antigen-binding fragment thereof comprises a VH CDR1 comprising the sequence SX$_2$VMT (SEQ ID NO: 39), wherein X$_2$ is C, S, or Y.

In one embodiment, the heavy chain variable region of the anti-FcRn antibody or antigen binding fragment thereof may comprise a framework composed of FR1 of the amino acid sequence of SEQ ID NO: 15, FR2 of the amino acid sequence of SEQ ID NO: 16, FR3 of the amino acid sequence of SEQ ID NO: 17, and FR4 of the amino acid sequence of SEQ ID NO: 18.

In FR3 in the framework on the heavy chain variable region, a specific amino acid may be substituted with another amino acid, but is not limited thereto. Specifically, the amino acid of Q16 in the amino acid sequence of SEQ ID NO: 17 may be substituted with another amino acid.

As described above, the above "substitution with another amino acid" is not particularly limited as long as the properties of the antibody according to the present disclosure are maintained even if the amino acid substitution occurs.

In one embodiment, the amino acid of Q16 in the amino acid sequence of SEQ ID NO: 17 may be substituted with Glu (E), but is not limited thereto.

In one embodiment, variant No. 8 comprises a light chain variable region comprising LCDR1 comprising the amino acid sequence of SEQ ID NO: 9, LCDR2 comprising the amino acid sequence of SEQ ID NO: 2, and LCDR3 comprising the amino acid sequence of SEQ ID NO: 3; and a heavy chain variable region comprising HCDR1 comprising the amino acid sequence of SEQ ID NO: 11, HCDR2 comprising the amino acid sequence of SEQ ID NO: 6, and HCDR3 comprising the amino acid sequence of SEQ ID NO: 7, wherein it may comprise FR3 of an amino acid sequence in which the amino acid of Q16 in the amino acid sequence of SEQ ID NO: 17 is substituted with Glu (E). In this regard, the Fc region of the antibody may be IgG1 or a variant thereof, IgG4 or a variant thereof. The variant No. 8 may be denoted as HL161ANSE, HL161ANSE (IgG1null) or HL161ANSE (IgG4).

In one embodiment, variant No. 19 comprises a light chain variable region comprising LCDR1 comprising the amino acid sequence of SEQ ID NO: 13, LCDR2 comprising the amino acid sequence of SEQ ID NO: 2, and LCDR3 comprising the amino acid sequence of SEQ ID NO: 3; and a heavy chain variable region comprising HCDR1 comprising the amino acid sequence of SEQ ID NO: 11, HCDR2 comprising the amino acid sequence of SEQ ID NO: 6, and HCDR3 comprising the amino acid sequence of SEQ ID NO: 7, wherein it may comprise FR3 of an amino acid sequence in which the amino acid of Q16 in the amino acid sequence of SEQ ID NO: 17 is substituted with Glu (E). In this regard, the Fc region of the antibody may be IgG1 or a variant thereof, IgG4 or a variant thereof. The variant No. 19 may be denoted as HL161ANQE, HL161ANQE (IgG1null) or HL161ANQE (IgG4).

In one embodiment, variant No. 11 comprises a light chain variable region comprising LCDR1 comprising an amino acid sequence in which the amino acid of N3 in the amino acid sequence of SEQ ID NO: 1 is substituted with Ser (S), LCDR2 comprising the amino acid sequence of SEQ ID NO: 2, and LCDR3 comprising the amino acid sequence of SEQ ID NO: 3; and a heavy chain variable region comprising HCDR1 comprising an amino acid sequence in which the amino acid of C2 in the amino acid sequence of SEQ ID NO: 5 is substituted with Tyr (Y), HCDR2 comprising the amino acid sequence of SEQ ID NO: 6, and HCDR3 comprising the amino acid sequence of SEQ ID NO: 7, wherein it may comprise FR3 of an amino acid sequence in which the amino acid of Q16 in the amino acid sequence of SEQ ID NO: 17 is substituted with Glu (E). In this regard, the Fc region of the antibody may be IgG1 or a variant thereof, IgG4 or a variant thereof. The variant No. 11 may be denoted as HL161ANSYE, HL161ANSYE (IgG1null) or HL161ANSYE (IgG4).

In one embodiment, variant No. 22 comprises a light chain variable region comprising LCDR1 comprising an amino acid sequence in which the amino acid of N3 in the amino acid sequence of SEQ ID NO: 1 is substituted with Gln (Q), LCDR2 comprising the amino acid sequence of SEQ ID NO: 2, and LCDR3 comprising the amino acid sequence of SEQ ID NO: 3; and a heavy chain variable region comprising HCDR1 comprising an amino acid sequence in which the amino acid of C2 in the amino acid sequence of SEQ ID NO: 5 is substituted with Tyr (Y), HCDR2 comprising the amino acid sequence of SEQ ID NO: 6, and HCDR3 comprising the amino acid sequence of SEQ ID NO: 7, wherein it may comprise FR3 of an amino acid sequence in which the amino acid of Q16 in the amino acid sequence of SEQ ID NO: 17 is substituted with Glu (E). In this regard, the Fc region of the antibody may be IgG1 or a variant thereof, IgG4 or a variant thereof. The variant No. 22 may be denoted as HL161ANQYE, HL161ANQYE (IgG1null) or HL161ANQYE (IgG4).

In another aspect of the present disclosure, there is provided an anti-FcRn antibody or an antigen binding fragment thereof comprising a light chain variable region comprising the amino acid sequence of SEQ ID NO: 4 and a heavy chain variable region comprising the amino acid sequence of SEQ ID NO: 8.

In this regard, in the anti-FcRn antibody or antigen binding fragment thereof, the amino acid of N25 in the amino acid sequence of SEQ ID NO: 4 may be substituted with another amino acid, and the amino acid of C32 or Q82 in the amino acid sequence of SEQ ID NO: 8 may be substituted with another amino acid.

The "anti-FcRn antibody," "antigen binding fragment" and "substitution with another amino acid" are as described above.

In one embodiment, the amino acid of N25 in the amino acid sequence of SEQ ID NO: 4 may be substituted with Ser (S) or Gln (Q), but is not limited thereto.

In one embodiment, the amino acid of C32 in the amino acid sequence of SEQ ID NO: 8 may be substituted with Ser (S) or Tyr (Y), but is not limited thereto.

In one embodiment, the amino acid of Q82 in the amino acid sequence of SEQ ID NO: 8 may be substituted with Glu (E), but is not limited thereto.

In one embodiment, the variant No. 1 may comprise a light chain variable region comprising the amino acid sequence of SEQ ID NO: 10 and a heavy chain variable region comprising the amino acid sequence of SEQ ID NO: 12. In this regard, the Fc region of the antibody may be IgG1 or a variant thereof, IgG4 or a variant thereof.

In one embodiment, the variant No. 12 may comprise a light chain variable region comprising the amino acid sequence of SEQ ID NO: 14 and a heavy chain variable region comprising the amino acid sequence of SEQ ID NO: 12. In this regard, the Fc region of the antibody may be IgG1 or a variant thereof, IgG4 or a variant thereof.

In one embodiment, the variant No. 2 may comprise a light chain variable region comprising the amino acid sequence of SEQ ID NO: 10 and a heavy chain variable region comprising an amino acid sequence in which the amino acid of C32 in the amino acid sequence of SEQ ID NO: 8 is substituted with Tyr (Y). In this regard, the Fc region of the antibody may be IgG1 or a variant thereof, IgG4 or a variant thereof.

In one embodiment, the variant No. 13 may comprise a light chain variable region comprising the amino acid sequence of SEQ ID NO: 14 and a heavy chain variable region comprising an amino acid sequence in which the amino acid of C32 in the amino acid sequence of SEQ ID NO: 8 is substituted with Tyr (Y). In this regard, the Fc region of the antibody may be IgG1 or a variant thereof, IgG4 or a variant thereof.

In one embodiment, the variant No. 8 may comprise a light chain variable region comprising the amino acid sequence of SEQ ID NO: 10 and a heavy chain variable region comprising an amino acid sequence in which the amino acid of C32 in the amino acid sequence of SEQ ID NO: 8 is substituted with Ser (S) and the amino acid of Q82 is substituted with Glu (E). In this regard, the Fc region of the antibody may be IgG1 or a variant thereof, IgG4 or a variant thereof.

In one embodiment, the variant No. 19 may comprise a light chain variable region comprising the amino acid sequence of SEQ ID NO: 14 and a heavy chain variable region comprising an amino acid sequence in which the amino acid of C32 in the amino acid sequence of SEQ ID NO: 8 is substituted with Ser (S) and the amino acid of Q82 is substituted with Glu (E). In this regard, the Fc region of the antibody may be IgG1 or a variant thereof, IgG4 or a variant thereof.

In one embodiment, the variant No. 11 may comprise a light chain variable region comprising the amino acid sequence of SEQ ID NO: 10 and a heavy chain variable region comprising an amino acid sequence in which the amino acid of C32 in the amino acid sequence of SEQ ID NO: 8 is substituted with Tyr (Y) and the amino acid of Q82 is substituted with Glu (E). In this regard, the Fc region of the antibody may be IgG1 or a variant thereof, IgG4 or a variant thereof.

In one embodiment, the variant No. 22 may comprise a light chain variable region comprising the amino acid sequence of SEQ ID NO: 14 and a heavy chain variable region comprising an amino acid sequence in which the amino acid of C32 in the amino acid sequence of SEQ ID NO: 8 is substituted with Tyr (Y) and the amino acid of Q82 is substituted with Glu (E). In this regard, the Fc region of the antibody may be IgG1 or a variant thereof, IgG4 or a variant thereof.

In some embodiments, an anti-FcRn antibody comprises a light chain variable region comprising a sequence that is at least 80%, at least 85%, at least 90%, at least 91%, at least 92%, at least 93%, at least 94%, at least 95%, at least 96%, at least 97%, at least 98%, or at least 99% identical to the sequence set forth in SEQ ID NO: 4. In some of these embodiments, the sequence of the CDRs of the light chain variable region is 100% identical to SEQ ID NO:4. In some embodiments, an anti-FcRn antibody comprises a light chain variable region comprising a sequence that is at least 80%, at least 85%, at least 90%, at least 91%, at least 92%, at least 93%, at least 94%, at least 95%, at least 96%, at least 97%, at least 98%, or at least 99% identical to the sequence set forth in SEQ ID NO: 10. In some of these embodiments, the sequence of the CDRs of the light chain variable region is 100% identical to SEQ ID NO:10. In some embodiments, an anti-FcRn antibody comprises a light chain variable region comprising a sequence that is at least 80%, at least 85%, at least 90%, at least 91%, at least 92%, at least 93%, at least 94%, at least 95%, at least 96%, at least 97%, at least 98%, or at least 99% identical to the sequence set forth in SEQ ID NO: 14. In some of these embodiments, the sequence of the CDRs of the light chain variable region is 100% identical to SEQ ID NO:14.

In some embodiments, an anti-FcRn antibody comprises a heavy chain variable region comprising a sequence that is at least 80%, at least 85%, at least 90%, at least 91%, at least 92%, at least 93%, at least 94%, at least 95%, at least 96%, at least 97%, at least 98%, or at least 99% identical to the sequence set forth in SEQ ID NO: 8. In some of these embodiments, the sequence of the CDRs of the heavy chain variable region is 100% identical to SEQ ID NO:8. In some embodiments, an anti-FcRn antibody comprises a heavy chain variable region comprising a sequence that is at least 80%, at least 85%, at least 90%, at least 91%, at least 92%, at least 93%, at least 94%, at least 95%, at least 96%, at least 97%, at least 98%, or at least 99% identical to the sequence set forth in SEQ ID NO: 12. In some of these embodiments, the sequence of the CDRs of the heavy chain variable region is 100% identical to SEQ ID NO:12.

In some embodiments, the anti-FcRn antibody comprises any of the CDRs, light chain variable regions and/or heavy chain variable regions described herein and further comprises an IgG1 Fc region. In some embodiments, the anti-FcRn antibody comprises any of the CDRs, light chain variable regions and/or heavy chain variable regions described herein and further comprises an IgG1 Fc region comprising Leu234Ala/Leu235Ala ("LALA") amino acid substitutions ("IgG1-LALA").

In some embodiments, the anti-FcRn antibody comprises any of the CDRs, light chain variable regions and/or heavy chain variable regions described herein and further comprises an IgG4 Fc region. In some embodiments, the anti-FcRn antibody comprises any of the CDRs, light chain variable regions and/or heavy chain variable regions described herein and further comprises an IgG4 Fc region comprising S228P amino acid substitution ("IgG4 S228P").

In some embodiments, an anti-FcRn antibody is an IgG1 antibody and comprises a light chain variable region comprising LCDR1 comprising the amino acid sequence of SEQ ID NO: 9, a LCDR2 comprising the amino acid sequence of SEQ ID NO: 2, and a LCDR3 comprising the amino acid sequence of SEQ ID NO: 3; and a heavy chain variable region comprising a HCDR1 comprising the amino acid sequence of SEQ ID NO: 11, a HCDR2 comprising the amino acid sequence of SEQ ID NO: 6, and a HCDR3 comprising the amino acid sequence of SEQ ID NO: 7. In some embodiments, an anti-FcRn antibody is an IgG4 antibody and comprises a light chain variable region comprising LCDR1 comprising the amino acid sequence of SEQ ID NO: 9, a LCDR2 comprising the amino acid sequence of SEQ ID NO: 2, and a LCDR3 comprising the amino acid sequence of SEQ ID NO: 3; and a heavy chain variable region comprising a HCDR1 comprising the amino acid sequence of SEQ ID NO: 11, a HCDR2 comprising the amino acid sequence of SEQ ID NO: 6, and a HCDR3 comprising the amino acid sequence of SEQ ID NO: 7.

In some embodiments, an anti-FcRn antibody is an IgG1-LALA antibody and comprises a light chain variable region comprising LCDR1 comprising the amino acid sequence of SEQ ID NO: 9, a LCDR2 comprising the amino acid sequence of SEQ ID NO: 2, and a LCDR3 comprising the amino acid sequence of SEQ ID NO: 3; and a heavy chain variable region comprising a HCDR1 comprising the amino acid sequence of SEQ ID NO: 11, a HCDR2 comprising the amino acid sequence of SEQ ID NO: 6, and a HCDR3 comprising the amino acid sequence of SEQ ID NO: 7. In some embodiments, an anti-FcRn antibody is an IgG4 S228P antibody and comprises a light chain variable region comprising LCDR1 comprising the amino acid sequence of SEQ ID NO: 9, a LCDR2 comprising the amino acid sequence of SEQ ID NO: 2, and a LCDR3 comprising the amino acid sequence of SEQ ID NO: 3; and a heavy chain variable region comprising a HCDR1 comprising the amino acid sequence of SEQ ID NO: 11, a HCDR2 comprising the amino acid sequence of SEQ ID NO: 6, and a HCDR3 comprising the amino acid sequence of SEQ ID NO: 7.

In one embodiment, the HL161ANS (IgG1null) may comprise a light chain region comprising the amino acid sequence of SEQ ID NO: 21 and a heavy chain region comprising the amino acid sequence of SEQ ID NO: 22.

In one embodiment, the HL161ANS (IgG4) may comprise a light chain region comprising the amino acid sequence of SEQ ID NO: 21 and a heavy chain region comprising the amino acid sequence of SEQ ID NO: 23.

In one embodiment, the HL161ANQ (IgG1null) may comprise a light chain region comprising the amino acid sequence of SEQ ID NO: 24 and a heavy chain region comprising the amino acid sequence of SEQ ID NO: 22.

In one embodiment, the HL161ANQ (IgG4) may comprise a light chain region comprising the amino acid sequence of SEQ ID NO: 24 and a heavy chain region comprising the amino acid sequence of SEQ ID NO: 23.

In one embodiment, the HL161ANSY (IgG1null) may comprise a light chain region comprising the amino acid sequence of SEQ ID NO: 21 and a heavy chain region comprising the amino acid sequence of SEQ ID NO: 25.

In one embodiment, the HL161ANSE (IgG1null) may comprise a light chain region comprising the amino acid sequence of SEQ ID NO: 21 and a heavy chain region comprising the amino acid sequence of SEQ ID NO: 26.

In one embodiment, the HL161ANSYE (IgG1null) may comprise a light chain region comprising the amino acid sequence of SEQ ID NO: 21 and a heavy chain region comprising the amino acid sequence of SEQ ID NO: 27.

In one embodiment, the HL161ANQY (IgG1null) may comprise a light chain region comprising the amino acid sequence of SEQ ID NO: 24 and a heavy chain region comprising the amino acid sequence of SEQ ID NO: 25.

In one embodiment, the HL161ANQE (IgG1null) may comprise a light chain region comprising the amino acid sequence of SEQ ID NO: 24 and a heavy chain region comprising the amino acid sequence of SEQ ID NO: 26.

In one embodiment, the HL161ANQYE (IgG1null) may comprise a light chain region comprising the amino acid sequence of SEQ ID NO: 24 and a heavy chain region comprising the amino acid sequence of SEQ ID NO: 27.

In one embodiment, the anti-FcRn antibody is an anti-FcRn antibody variant prepared by substituting an amino acid residue at a specific site of the parent antibody HL161AN, and it was confirmed that it has the reduced production rate of aggregates while maintaining high affinity and specificity to FcRn like the parent antibody. In one embodiment, the anti-FcRn antibody is an anti-FcRn antibody variant prepared by substituting an amino acid residue at a specific site of the parent antibody HL161AN, and it was confirmed that it has the reduced production rate of aggregates while maintaining high affinity for FcRn like the parent antibody. Specifically, it was confirmed that the anti-FcRn antibody variant according to the present disclosure has improved stability, such as reduction in the production rate of aggregates by up to two-fold or more while having excellent biological activities, like the previously developed parent antibody HL161AN (Korean Patent No. 10-1954906), such as productivity, an action as an inhibitor for the binding of IgG and FcRn, and an IgG catabolism effect, i.e., promotion of IgG clearance.

Therefore, the anti-FcRn antibody variant according to the present disclosure, which has significantly improved stability while having excellent biological activities like the previously developed parent antibody HL161AN, may be usefully used for the treatment of an autoimmune disease.

In some embodiments, administration of an anti-FcRn antibody described herein to a subject decreases blood immunoglobulin levels (e.g., IgG levels) in the subject by at least or more than 30%, 40%, 50%, 60%, 65% or 80% compared to the blood immunoglobulin levels (e.g., IgG levels) in the subject prior to administration of the anti-FcRn antibody.

In some embodiments, an anti-FcRn antibody described herein results in lower immunoglobulin levels (e.g., IgG levels) in the blood of a subject than another anti-FcRn antibody when administered to a subject. In some embodiments, the anti-FcRn antibody described herein results in lower immunoglobulin levels (e.g., IgG levels) in the blood of a subject than batoclimab. In some embodiments, administration of the anti-FcRn antibody described herein to a subject decreases immunoglobulin levels, (e.g., IgG levels) in the blood of the subject to about the same level as administration of a comparable dose of batoclimab. Batoclimab is known in the art, and also described in, e.g., international patent application publication No. WO2015/167293, which is incorporated by reference herein in its entirety; batoclimab is referred to as "HL161BKN" in WO2015/167293.

In some embodiments, administration to a subject (e.g., a human) of an effective amount of the anti-FcRn antibody described herein decreases blood albumin levels by less than 5%, less than 10%, less than 20%, or less than 30% compared to the blood albumin levels prior to administration. In some embodiments, administration to a subject (e.g., a human) of an effective amount of the anti-FcRn antibody described herein increases blood cholesterol levels by less than 5%, less than 10%, less than 20%, or less than 30% compared to the blood cholesterol levels prior to administration.

In some embodiments, administration to a subject (e.g., a human) of an effective amount of the anti-FcRn antibody described herein increases blood total cholesterol levels by less than 5%, less than 10%, less than 20%, or less than 30% compared to the blood total cholesterol levels prior to administration.

In some embodiments, administration to a subject (e.g., a human) of an effective amount of the anti-FcRn antibody described herein increases blood LDL levels by less than 5%, less than 10%, less than 20%, or less than 30% compared to the blood LDL levels prior to administration.

In some embodiments, administration to a subject (e.g., a human) of an effective amount of the anti-FcRn antibody described herein decreases blood immunoglobulin levels by at least about 40%, 50%, 65% or 80%, but (i) has no or minimal effect on blood albumin levels (e.g., decreases blood albumin by less than 20%, 10%, less than 5%, less than 2%, or less than 1%) and/or (ii) has no or minimal effect on blood total cholesterol levels and/or LDL levels (e.g., increases cholesterol by less than 20%, 10%, less than 5%, less than 2%, or less than 1%) compared to the levels prior to administration.

In some embodiments, administration to a subject (e.g., a human) of an effective amount of the anti-FcRn antibody described herein decreases blood immunoglobulin levels by at least about 40%, 50%, 65% or 80%, but has no or minimal effect on blood albumin levels (e.g., decreases blood albumin by less than 10%, less than 5%, less than 2%, or less than 1%) and has no or minimal effect on blood cholesterol (e.g., increases cholesterol by less than 10%, less than 5%, less than 2%, or less than 1%) compared to the levels prior to administration.

In some embodiments, subcutaneous administration to a human subject (e.g., chronic subcutaneous administration to a human) of an effective amount of the anti-FcRn antibody described herein decreases blood immunoglobulin levels by at least about 40%, 50%, 65% or 80%, but has no or minimal effect on blood albumin levels (e.g., decreases blood albumin by less than 10%, less than 5%, less than 2%, or less than 1%) and has no or minimal effect on blood cholesterol (e.g., increases cholesterol by less than 10%, less than 5%, less than 2%, or less than 1%) compared to the levels prior to administration.

In some embodiments, administration to a subject (e.g., a human) of an effective amount of the anti-FcRn antibody described herein decreases blood immunoglobulin levels by at least about 40%, 50%, 65% or 80%, but has no or minimal effect on blood albumin levels (e.g., decreases blood albumin by less than 10%, less than 5%, less than 2%, or less than 1%) and has no or minimal effect on blood LDL levels (e.g., increases LDL by less than 10%, less than 5%, less than 2%, or less than 1%) compared to the levels prior to administration.

In some embodiments, subcutaneous administration to a human subject (e.g., chronic subcutaneous administration to a human) of an effective amount of the anti-FcRn antibody described herein decreases blood immunoglobulin levels by at least about 40%, 50%, 65% or 80%, but has no or minimal effect on blood albumin levels (e.g., decreases blood albumin by less than 10%, less than 5%, less than 2%, or less than 1%) and has no or minimal effect on blood LDL levels (e.g., increases LDL by less than 10%, less than 5%, less than 2%, or less than 1%) compared to the levels prior to administration.

In some embodiments, chronic subcutaneous administration to a human for 12 weeks or more of an effective amount of the anti-FcRn antibody described herein decreases blood immunoglobulin levels by at least about 40%, 50%, 65% or 80%, but has no or minimal effect on blood albumin levels (e.g., decreases blood albumin by less than 10%, less than 5%, less than 2%, or less than 1%) and has no or minimal effect on blood LDL and/or cholesterol levels (e.g., increases LDL and/or cholesterol by less than 10%, less than 5%, less than 2%, or less than 1%) compared to the levels prior to administration.

Functional variants of the antibody or antigen-binding fragments described herein are also encompassed by the present disclosure. The term "functional variant" as used herein includes modifications or chemical equivalents of the amino acid and nucleic acid sequences disclosed herein that perform substantially the same function as the polypeptides or nucleic acid molecules disclosed herein in substantially the same way. For example, functional variants of polypeptides disclosed herein include, without limitation, conservative amino acid substitutions. A "conservative amino acid substitution" as used herein, is one in which one amino acid residue is replaced with another amino acid residue are substitutions that change an amino acid to a different amino acid with similar biochemical properties (e.g. charge, hydrophobicity and size). For example, lysine, arginine and histidine have similar properties in that they have a basic side-chain, and aspartic acid and glutamic acid have similar properties in that they have an acidic side chain. In addition, glycine, asparagine, glutamine, serine, threonine, tyrosine, cysteine and tryptophan have similar properties in that they have an uncharged polar side-chain, and alanine, valine, leucine, threonine, isoleucine, proline, phenylalanine and methionine have similar properties in that they have a non-polar side-chain. Also, tyrosine, phenylalanine, tryptophan and histidine have similar properties in that they have an aromatic side-chain. Thus, it will be obvious to those skilled in the art that, even when substitution of amino acid residues in groups showing similar properties as described above occurs; it will show no particular change in the properties. Variants of polypeptides also include additions and deletions to the polypeptide sequences disclosed herein. In addition, variant nucleotide sequences include analogs and derivatives thereof. A variant of the binding proteins disclosed herein include proteins that bind to the same antigen or epitope as the binding proteins.

As will be apparent to a person of skill in the art, the C-terminal lysine of an immunoglobulin heavy chain may be cleaved during production. Thus, in some embodiments, an antibody described herein comprises two C-terminal lysine residues (i.e., one C-terminal lysine on each heavy chain). In some embodiments, an antibody described herein comprises one C-terminal lysine residue (i.e., a C-terminal lysine on one heavy chain and no C-terminal lysine on the other heavy chain). In some embodiments, an antibody described herein comprises no C-terminal lysine residues on either heavy chain.

It can be desirable to modify an antibody disclosed herein with respect to effector function, so as to enhance, e.g., the effectiveness of the antibody in treating diseases and disorders associated. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J Exp Med., 176:1191-1195 (1992) and Shopes, J. Immunol., 148:2918-2922 (1992)). Alternatively, an antibody can be engineered that has dual Fc regions and can thereby have enhanced complement lysis and ADCC capabilities. (See Stevenson et al., Anti-Cancer Drug Design, 3:219-230 (1989)). Mutations affecting the effector function of antibodies are known in the art, see, e.g., Saunders et al., 2019; Front. Immunol. 10:1296 and Wang et al., 2018, Protein Cell 9(1): 63-73, each of which is incorporated herein by reference in its entirety for examples of Fc modifications that may be introduced in the antibodies described herein. Unless otherwise indicated, the Fc mutations in this section are described with reference to the Kabat numbering scheme for immunoglobulins. Illustrative mutations and combinations of mutations that may be introduced into the Fc of an anti-FcRn antibody provided herein include, without limitation, Lys326Trp/Glu333Ser, Ser267Glu/His268Phe/Ser324Thr, Lys326Trp/Glu333Ser, Lys326Ala/Glu333Ala, Lys326Met/Glu333Ser, Cys221Asp/Asp222Cys, Ser267Glu, His268Phe, Ser324Thr, Glu345Arg, S239D/I332E, S239D/I332E/A330L, Arg435His, Met252Tyr/Ser254Thr/Thr256Glu ("YTE"), Met428Leu/Asn434Ser, Thr252Leu/Thr253Ser/Thr254Phe, Leu235Glu, Leu234Ala/Leu235Ala ("LALA"), Ser228Pro/Leu235Glu, Leu234Ala/Leu235Ala/Pro329Gly, Pro331Ser/Leu234Glu/Leu235Phe, Asp265Ala, and Ala330Leu.

In some embodiments, the anti-FcRn antibody is an IgG1 antibody comprising Leu234Ala/Leu235Ala ("LALA") mutations (i.e., is an "IgG1-LALA" antibody). In some embodiments, the anti-FcRn antibody is an IgG4 antibody comprising S228P mutation (i.e., is an "IgG4 S228P" antibody).

Polynucleotide Encoding Anti-FcRn Antibody Variant

In another aspect of the present disclosure, there is provided a polynucleotide encoding the anti-FcRn antibody or antigen binding fragment thereof.

Specifically, a polynucleotide encoding the heavy chain may comprise the sequence of SEQ ID NO: 31, 33, 35 or 37. In addition, a polynucleotide encoding the light chain may comprise the sequence of SEQ ID NO: 30, 32, 34 or 36.

The polynucleotide may comprise a nucleic acid sequence having at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO: 30, 31, 32, 33, 34, 35, 36 or 37.

In some embodiments, the polynucleotide comprises the sequence of SEQ ID NO: 30. In some embodiments, the polynucleotide comprises the sequence of SEQ ID NO: 31. In some embodiments, the polynucleotide comprises the sequences of SEQ ID NO: 30 and SEQ ID NO: 31. In some embodiments, the polynucleotide comprises the sequence of SEQ ID NO: 32. In some embodiments, the polynucleotide comprises the sequence of SEQ ID NO: 33. In some embodiments, the polynucleotide comprises the sequences of SEQ ID NO: 32 and SEQ ID NO: 33.

The polynucleotide may be mutated by substitution, deletion, insertion of one or more bases, or a combination thereof. When the nucleotide sequence is prepared by chemical synthesis, synthesis methods well known in the art, for example, the method described in the literature (Engels and Uhlmann, Angew Chem IntEd Engl., 37:73-127, 1988) may be used, and may include triester, phosphite, phosphoramidite and H-phosphate methods, PCR and other autoprimer methods, synthesis methods of oligonucleotide on a solid support, and the like.

Vector Loaded with Polynucleotide Encoding Anti-FcRn Antibody Variant

In another aspect of the present disclosure, there is provided a recombinant expression vector comprising the polynucleotide.

In addition, the polynucleotide may have a heavy chain and a light chain loaded into one vector, or loaded into two vectors, respectively.

Specifically, when loaded into one vector, the polynucleotide may comprise the polynucleotide of SEQ ID NO: 30 and the polynucleotide of SEQ ID NO: 31; the polynucleotide of SEQ ID NO: 32 and the polynucleotide of SEQ ID NO: 33; the polynucleotide of SEQ ID NO: 34 and the polynucleotide of SEQ ID NO: 35; or the polynucleotide of SEQ ID NO: 36 and the polynucleotide of SEQ ID NO: 37.

A vector provided herein may comprise a polynucleotide encoding the light chain of an anti-FcRn antibody or antigen-binding fragment thereof and/or the heavy chain an anti-FcRn antibody or antigen-binding fragment thereof.

In some embodiments, the vector comprises a polynucleotide comprising the sequence of SEQ ID NO: 30. In some embodiments, the vector comprises a polynucleotide comprising the sequence of SEQ ID NO: 31. In some embodiments, the vector comprises a polynucleotide comprising the sequence of SEQ ID NO: 30 (encoding the light chain) and the sequence of SEQ ID NO: 31 (encoding the heavy chain).

In some embodiments, the vector comprises a polynucleotide comprising the sequence of SEQ ID NO: 32. In some embodiments, the vector comprises a polynucleotide comprising the sequence of SEQ ID NO: 33. In some embodiments, the vector comprises a polynucleotide comprising the sequence of SEQ ID NO: 32 (encoding the light chain) and the sequence of SEQ ID NO: 33 (encoding the heavy chain).

The vector may be introduced into a host cell and recombined and inserted into a host cell genome. Alternatively, the vector is understood to be a nucleic acid means comprising a polynucleotide sequence capable of spontaneous replication as an episome. The vector includes linear nucleic acids, plasmids, phagemids, cosmids, RNA vectors, viral vectors and analogs thereof. Examples of viral vectors include retrovirus, adenovirus, and adeno-associated virus, but are not limited thereto.

Specifically, the vector may be plasmid DNA, phage DNA, and the like. In addition, it may be commercially developed plasmids (pUC18, pBAD, pIDTSAMRT-AMP, etc.), E. coli derived plasmids (pYG601BR322, pBR325, pUC118, pUC119, etc.), Bacillus subtilis-derived plasmids (pUB110, pTP5, etc.), yeast-derived plasmids (YEp13, YEp24, YCp50, etc.), phage DNA (Charon4A, Charon21A, EMBL3, EMBL4, λgt10, λgt11, λZAP, etc.), animal viral vectors (retrovirus, adenovirus, vaccinia virus, etc.), insect viral vectors (baculovirus, etc.). Since the vector shows different protein expression levels and modifications depending on the host cell, it is preferable to select and use the most suitable host cell for the purpose.

The vector of the present disclosure may be fused with other sequences in order to facilitate purification of the antibody expressed therefrom. The sequence to be fused includes, for example, glutathione S-transferase (Pharmacia, USA), maltose binding protein (NEB, USA), FLAG (IBI, USA), 6×His (hexahistidine; Quiagen, USA), and the like.

In addition, since the protein expressed by the vector of the present disclosure is an antibody, the expressed antibody may be easily purified through a Protein A column or the like without an additional sequence for purification.

Transformed Cell Expressing Anti-FcRn Antibody Variant

In another aspect of the present disclosure, there is provided a host cell transformed with the recombinant expression vector.

A host cell of the transformed cell may include a prokaryotic cell, a eukaryotic cell, a cell of mammal, plant, insect, fungal or cellular origin, but is not limited thereto. E. co/i may be used as an example of the prokaryotic cell. In addition, yeast may be used as an example of the eukaryotic cell. In addition, as the mammal cell, CHO cells, F2N cells, CSO cells, BHK cells, Bowes melanoma cells, HeLa cells, 911 cells, AT1080 cells, A549 cells, HEK 293 cells, HEK293T cells, or the like may be used, but is not limited thereto, and any cell that may be used as a mammalian host cell known to one of ordinary skill in the art is available.

In the present disclosure, "transformation" or "transfection" into a host cell includes any method of introducing a nucleic acid into an organism, cell, tissue or organ, and as is known in the art, suitable standard techniques may be selected and performed depending on the host cell. For example, CaCl$_2$) precipitation method, Hanahan method with increased efficiency by using DMSO (dimethyl sulfoxide) as a reducing agent in CaCl$_2$) precipitation method, electroporation, calcium phosphate precipitation method, protoplast fusion method, stirring method using silicon carbide fiber, agrobacterium-mediated transformation method, transformation method using PEG, dextran sulfate, lipofectamine and drying/inhibition mediated transformation method, and the like may be used.

Method for Producing Anti-FcRn Antibody Variant or Antigen Binding Fragment Thereof In another aspect of the present disclosure, there is provided a method for producing an anti-FcRn antibody or an antigen binding fragment thereof, comprising culturing the host cell to produce an antibody; and isolating and purifying the produced antibody to recover an antibody that specifically binds to FcRn.

The FcRn specific antibody according to the present disclosure may be produced in a large quantity by culturing the transformant expressing the recombinant vector in a nutrient medium, and the medium and culture conditions that are tolerated depending on the host cell may be appropriately selected and used. In culture, conditions such as temperature, pH of the medium, and culture duration may be appropriately regulated to be suitable for cell growth and mass production of proteins. The antibody or antibody fragment that are recombinantly produced as described above may be recovered from the medium or cell lysate, and may be isolated and purified by conventional biochemical separation techniques (Sambrook et al., Molecular Cloning: A laboratory Manual, 2nd Ed., Cold Spring Harbor Laboratory Press (1989); Deuscher, M., Guide to Protein Purification Methods Enzymology, Vol. 182. Academic Press. Inc., San Diego, CA (1990)). As an example, electrophoresis, centrifugation, gel filtration, precipitation, dialysis, chromatography (ion exchange chromatography, affinity chromatography, immunosorbent chromatography, size exclusion chromatography, etc.), isoelectric focusing, and methods with various modifications and combinations thereof, and the like may be used, but are not limited thereto. In particular, isolation and purification using Protein A is preferable.

In particular, the anti-FcRn antibody or antigen binding fragment thereof is preferably prepared by expression and purification using a genetic recombination method. Specifically, it is preferable to prepare the variable region encoding the antibody that specifically binds to FcRn according to the present disclosure by simultaneous expression in one host cell.

Use of Anti-FcRn Antibody Variant or Antigen Binding Fragment Thereof

In another aspect of the present disclosure, there is provided a pharmaceutical composition for treating an autoimmune disease, comprising the anti-FcRn antibody or antigen binding fragment thereof. Also provided herein is a method of treating an autoimmune disorder comprising administering to a subject in need thereof an effective amount of an anti-FcRn antibody or antigen-binding fragment thereof, or a pharmaceutical composition described herein.

The "anti-FcRn antibody" and "antigen binding fragment" are as described above.

As used herein, the term "autoimmune disease" is a generic term for diseases that occur when the immune system attacks its normal tissues, organs, or other body components due to an abnormality of the immune system of unknown cause. It is a systemic disease that may occur in almost any part of the body, including the nervous system, gastrointestinal system, endocrine system, skin, skeletal system, vascular tissue, and the like.

The pharmaceutical composition may be applied to all autoimmune diseases mediated by IgG and FcRn. Representative autoimmune diseases may be one selected from the group consisting of autoimmune neutropenia, Guillain-Barre syndrome, epilepsy, autoimmune encephalitis, Isaacs' syndrome, nevus syndrome, pemphigus vulgaris, deciduous pemphigus, bullous pemphigoid, acquired epidermolysis bullosa, gestational pemphigoid, mucous membrane pemphigoid, antiphospholipid syndrome, autoimmune anemia, autoimmune Graves' disease, Goodpasture syndrome, myasthenia gravis, multiple sclerosis, rheumatoid arthritis, lupus, idiopathic thrombocytopenic purpura (ITP), lupus nephritis, membranous nephropathy, allogenic islet graft rejection, alopecia areata, ankylosing spondylitis, autoimmune Addison's disease, Alzheimer's disease, antineutrophil cytoplasmic autoantibodies (ANCA), autoimmune disorders of the adrenal gland, warm autoimmune hemolytic anemia (WAIHA), autoimmune hepatitis, autoimmune myocarditis, autoimmune oophoritis and orchitis, autoimmune thrombocytopenia, autoimmune urticaria, Behcet's disease, cardiomyopathy, Castleman's syndrome, celiac spruce-dermatitis, chronic fatigue immune dysfunction syndrome, chronic inflammatory demyelinating polyneuropathy (CIDP), Churg-Strauss syndrome, cicatrical pemphigoid, CREST syndrome, cold agglutinin disease, Crohn's disease, dermatomyositis, dilated cardiomyopathy, discoid lupus, essential mixed cryoglobulinemia, factor VIII deficiency, fibromyalgia-fibromyositis, glomerulonephritis, thyroid eye disease (TED, also known as Graves' Ophthalmopathy); graft-versus-host disease (GVHD), Hashimoto's thyroiditis, hemophilia A, idiopathic membranous neuropathy, idiopathic pulmonary fibrosis, IgA neuropathy, IgM polyneuropathies, immune mediated thrombocytopenia, juvenile arthritis, Kawasaki's disease, lichen plantus, lichen sclerosus, lupus erthematosis, Meniere's disease, mixed connective tissue disease, type 1 diabetes mellitus, Multifocal motor neuropathy (MMN), paraneoplastic bullous pemphigoid, pemphigus foliaceus, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, relapsing polychondritis, Reynauld's phenomenon, Reiter's syndrome, sarcoidosis, scleroderma, Sjogren's syndrome, solid organ transplant rejection, stiff-man syndrome, systemic lupus erythematosus, takayasu arteritis, toxic epidermal necrolysis (TEN), Stevens Johnson syndrome (SJS), temporal arteristis, giant cell arteritis, thrombotic thrombocytopenia purpura, ulcerative colitis, uveitis, dermatitis herpetiformis vasculitis, antineutrophil cytoplasmic antibody-associated vasculitides, vitiligo, and Wegner's granulomatosis. In some embodiments, the autoimmune disorder is an autoimmune channelopathy, optionally wherein the channelopathy is selected from the group consisting of autoimmune limbic encephalitis, neuromyelitis optica, Lambert-Eaton myasthenic syndrome, myasthenia gravis, anti-N-Methyl-D-aspartate (NMDA) receptor encephalitis, anti-α-Amino-3-hydroxy-5-methyl-4-isoxazolepropionic acid (AMPA) receptor encephalitis, Morvan syndrome, neuromyotonia, pediatric autoimmune neuropsychiatric disorders associated with streptococcal infection (PANDAS), Glycine receptor antibody-associated disorder, myositis, myelin oligodendrocyte glycoprotein antibody disorders (MOG-antibody disorder), Hemolytic disease of the foetus and new-born, cutaneous lupus erythematosus, refractory rheumatoid arthritis, immune thrombocytopenia, anti-GBM disease, Primary Membranous Nephropathy, Necrotizing Autoimmune Myopathy, Antisynthetase Syndrome, ANCA vasculitis, Hidradenitis Suppurativa, pulmonary alveolar proteinosis (PAP) and systemic lupus erythematosus (SLE), but are not limited thereto.

In some embodiments, the disease treated in accordance with a method described herein is a disease that is characterized by or exhibits increased blood total IgG levels in a subject to be treated. In some embodiments, the disease treated in accordance with a method described herein is any one of the autoimmune diseases referenced herein. In some embodiments, the disease is an autoimmune Graves' Disease. In some embodiments, the disease is thyroid eye disease (TED, also known as Graves' Ophthalmopathy). In some embodiments, the disease is warm autoimmune hemolytic anemia (WAIHA). In some embodiments, the disease is myasthenia gravis. In some embodiments, the disease is chronic inflammatory demyelinating polyneuropathy (CIDP). In some embodiments, the disease is pemphigus vulgaris, pemphigus foliaceus, deciduous pemphigus, bullous pemphigoid, gestational pemphigoid, or mucous membrane pemphigoid.

In some embodiments, the disease treated in accordance with a method described herein is a disease that responds to plasma exchange therapy. The subject treated in accordance with a method described herein may have previously undergone plasma exchange. In some embodiments, the disease treated in accordance with a method described herein is a disease that responds to a therapy that decreases total IgG levels. The subject treated in accordance with a method described herein may have previously undergone a therapy that decreases total IgG levels. In some embodiments, the disease treated in accordance with a method described herein is a disease that responds to rituximab. The subject treated in accordance with a method described herein may have previously undergone treatment with rituximab.

In some embodiments, the anti-FcRn antibody or antigen-specific fragment thereof described herein decreases the level of an antigen-specific immunoglobulin or an autoantibody, such as any of the autoantibodies described herein or known in the art. In some embodiments, the anti-FcRn antibody or antigen-specific fragment thereof described herein decreases the level of an autoimmune disease-specific autoantibody or an autoantibody associated, or known to be associated, with an autoimmune disease, such as any of the autoantibodies described herein or known in the art. In some embodiments, the autoimmune disease is any of the autoimmune diseases disclosed herein.

In some embodiments, administration (e.g., subcutaneous) to a subject (e.g., a human) of an effective amount of the anti-FcRn antibody described herein decreases antigen-specific immunoglobulin levels or an autoantibody level (e.g., the level of any one or more of the autoantibodies described herein) in the blood by at least about 40%, 50%, 65% or 80%. In some embodiments, such administration has no or minimal effect on blood albumin levels (e.g., decreases blood albumin by less than 10%, less than 5%, less than 2%, or less than 1%) and/or has no or minimal effect on blood LDL levels (e.g., increases LDL by less than 10%, less than 5%, less than 2%, or less than 1%) compared to the levels prior to administration. In some embodiments, the antigen-specific immunoglobulin or the autoantibody is associated with a disease, such as an autoimmune disease.

In some embodiments, chronic subcutaneous administration to a human for 12 weeks or more of an effective amount of the anti-FcRn antibody described herein decreases antigen-specific immunoglobulin levels or an autoantibody level (e.g., the level of any one or more of the autoantibodies described herein) in the blood by at least about 40%, 50%, 65% or 80%, but has no or minimal effect on blood albumin levels (e.g., decreases blood albumin by less than 10%, less than 5%, less than 2%, or less than 1%) and has no or minimal effect on blood LDL and/or cholesterol levels (e.g., increases LDL and/or cholesterol by less than 10%, less than 5%, less than 2%, or less than 1%) compared to the levels prior to administration. In some embodiments, the antigen-specific immunoglobulin or the autoantibody is associated with a disease, such as an autoimmune disease.

Illustrative examples of autoantibodies associated with specific autoimmune diseases include:
  anti-Desmoglein 3 (anti-Dsg3) antibody (associated with pemphigus vulgaris),
  anti-Desmoglein 1 (anti-Dsg1) antibody (associated with pemphigus vulgaris and pemphigus foliaceus), anti-Bullous Pemphigoid 180 (anti-BP180 or anti-collagen XVII) antibody and anti-Bullous Pemphigoid 230 (anti-BP230) antibody (both associated with bullous pemphigoid), antibodies against the noncollagenous domain 1 of the 3 chain of type IV collagen (anti-3 NC1 antibody) and against the noncollagenous domain 1 of the 5 chain of type IV collagen (anti-5 NC1 antibody) (both associated with anti-GBM disease), anti-phospholipase A2 receptor (anti-PLA2R) antibody (associated with idiopathic membranous nephropathy), anti-proteinase 3 (anti-PR3) antibody and anti-Myeloperoxidase (anti-MPO) antibody (both associated with ANCA-associated vasculitis), anti-double stranded (ds)-DNA antibody, antibody against anti-Sjögren's-syndrome-related antigen A (anti-SSA/Ro antibody) and anti-Sjögren's-syndrome-related antigen B (anti-SSB/La antibody), anti-Smith antibody, anti-ribonucleoprotein (anti-RNP) antibody, anti-complement C1q antibody, anti-proliferating cell nuclear antigen (PCNA) antibody, anti-cardiolipin antibody, anti-beta2 glycoprotein antibody, anti-granzyme B antibody, and anti-nucleosome antibody (all associated with systemic lupus erythematosus), anti-nuclear antibody (associated with systemic lupus erythematosus, systemic sclerosis and autoimmune hepatitis), rheumatoid factor, anti-citrullinated peptide antibody (ACPA), anti-CarP antibody, and anti-acetylated peptide antibody (AAPA) (all associated with rheumatoid arthritis), anti-centromere antibody (ACA), anti-Scl-70 antibody, anti-endothelial cell antibody (AECA), angiotensin II type-1-receptor (anti-AT1R) antibody, and anti-endothelin-1 type A receptor (anti-ETAR) antibody (all associated with systemic sclerosis), anti-signal recognition particle (anti-SRP) antibody (associated with immune-mediated necrotizing myopathy and polymyositis), anti-HMG-CoA reductase (anti-HMGCR) antibody (associated with immune-mediated necrotizing myopathy), anti-Jo-1 antibody, anti-PL-7 antibody, anti-PL-12 antibody, anti-EJ antibody, anti-OJ antibody, anti-Mi-2-antibody, anti-U3 ribonucleoprotein (anti-U3 RNP or anti-fibrillarin) antibody, anti-U2 ribonucleoprotein and (anti-U2 RNP) antibody (all associated with polymyositis), anti-Ku antibody (associated with systemic lupus erythematosus and polymyositis), anti-nuclear matrix protein 2 (anti-NXP-2) antibody, anti-Mi2 antibody, anti-melanoma differentiation-associated protein 5 (anti-MDA5) antibody, and anti-transcription intermediary factor 1-gamma (anti-TIF17) antibody (all associated with dermatomyositis), anti-acetylcholine receptor (anti-AChR) antibody, anti-muscle-specific kinase (anti-MuSK) antibody, and anti-lipoprotein-related protein 4 (anti-LRP4) antibody (all associated with myasthenia gravis), anti-neurofascin-155 (anti-Nfasc155) antibody, anti-neurofascin-140/186 (anti-Nfasc140/186) antibody, anti-contactin-1 (anti-CNTN1) antibody, and anti contactin-associated protein-like 1 (anti-Caspr1) antibody (all associated with Chronic Inflammatory Demyelinating Polyneuropathy (CIDP)), anti-ganglioside GM1 (anti-GM1) antibody, anti-ganglioside GT1a (anti-GT 1a) antibody, and anti-ganglioside GD1a (anti-GD1a) antibody (all associated with Guillain-Barre syndrome), anti-ganglioside GQ1b (anti-GQ1b) antibody (associated with Guillain-Barre syndrome and Miller Fisher syndrome), anti-aquaporin-4 (anti-AQP4) antibody (associated with neuromyelitis optica spectrum disorders), anti-NMDAR antibodies (associated with systemic lupus erythematosus and autoantibody-positive autoimmune encephalitis), anti-contactin-associated protein-like 2 (anti-Caspr2) antibody, anti-gamma-amino butyric acid receptor type B (anti-GABAbR) antibody, anti-leucine-rich glioma-inactivated 1 (anti-LGI1) antibody, and anti-Kelch-Like Protein 11 (anti-Klh11) antibody (all associated with autoantibody-positive autoimmune encephalitis), anti-β2 glycoprotein I (anti-β2GPI) antibody, and anti-phospholipid antibody (both associated with primary antiphospholipid syndrome), anti-FcγRIIIb antibody and anti-CD177 antibody (both associated with Primary Autoimmune Neutropenia), anti-smooth muscle actin (anti-SMA) antibody and anti-liver-kidney microsomal (anti-LKM) antibody (both associated with autoimmune hepatitis), anti-ADAMTS13 antibody (associated with idiopathic thrombotic thrombocytopenic purpura), anti-platelet GP IIb/IIIa antibody and anti-platelet GP Ib/IX antibody (both associated with idiopathic immune thrombocytopenic purpura), thyroid stimulating hormone (TSH)-binding inhibitor immunoglobulin (TBII), thyroid-stimulating immuno-globulins (TSI), thyrotropin-binding inhibitory (TBI) antibody, and anti-insulin-like growth factor 1 receptor (anti-IFG1R) antibody (all associated with Graves' disease and thyroid eye disease), anti-thyroid peroxidase (anti-TPO) antibody (associated with Autoimmune Thyroiditis/Hashimoto's Thyroiditis), anti-thyroglobulin antibody (associated with Graves' Disease), islet cell cytoplasmic autoantibody (ICA), glutamic acid decarboxylase autoantibody (GADA), insulinoma-associated-2 autoantibody (IA-2A), and insulin autoantibody (IAA) (all associated with Type 1 diabetes), neutralizing anti-adenovirus antibody, neutralizing anti-lentivirus antibody, neutralizing anti-AAV1, AAV2, AAV3 AAV4, AAV5, AAV6, AAV7, AAV8, and/or AAV9 antibody (associated with prior gene therapy), and anti-granulocyte-macrophage colony stimulating factor (anti-GM-CSF) antibody (associated with acquired pulmonary alveolar proteinosis (PAP).

In some embodiments, administration to a human subject (e.g., subcutaneous or chronic subcutaneous administration to a human) of an effective amount of the anti-FcRn antibody described herein decreases proteinuria in a subject having lupus nephritis by at least about 40%, 50%, 65% or 80%, as measured by the levels of protein in the urine of the subject.

The preferred dosage of the pharmaceutical composition may vary depending on the condition and body weight of the patient, the severity of the disease, the form of the drug, the route and duration of administration, but may be appropriately selected by one of ordinary skill in the art. In the pharmaceutical composition for the treatment or prevention of an autoimmune disease of the present disclosure, the active ingredient may be included in any amount (effective amount) depending on the use, formulation, purpose of combining, and the like, as long as it may exhibit therapeutic activity for an autoimmune disease, or in particular, a therapeutic effect on an autoimmune disease. A typical effective amount will be determined within the range of 0.001% by weight to 20.0% by weight based on the total weight of the composition. As used herein, the term "effective amount" refers to an amount of an active ingredient having an effect of treating or improving the state of an autoimmune disease, in particular, an amount of an active ingredient capable of inducing an effect of treating or improving the state of an autoimmune disease. Such an effective amount may be determined empirically within the ordinary ability of one of ordinary skill in the art.

In one embodiment, the term "treatment" includes any form of administration or application for treating a disease in a mammal, including a human. In addition, the above term includes inhibiting or slowing the disease or its progression; restoring or repairing damaged or missing function, thereby partially or completely alleviating the disease; stimulating inefficient processes; or alleviating serious diseases.

In another aspect, provided herein is a method of preventing an autoimmune disorder comprising administering to a subject in need thereof an effective amount of an anti-FcRn antibody or antigen-binding fragment thereof, or a pharmaceutical composition described herein.

Any embodiment herein that refers to methods of treating an autoimmune disorder comprising administering an anti-FcRn antibody, an antigen-binding fragment thereof, or a pharmaceutical composition also encompasses use of the anti-FcRn antibody, an antigen-binding fragment thereof, or the pharmaceutical composition for preparation of a medicament for treating an autoimmune disorder. Likewise, any embodiment herein that refers to methods of preventing an autoimmune disorder comprising administering an anti-FcRn antibody, an antigen-binding fragment thereof, or a pharmaceutical composition also encompasses use of the anti-FcRn antibody, an antigen-binding fragment thereof, or the pharmaceutical composition for preparation of a medicament for preventing an autoimmune disorder.

Pharmacokinetic parameters such as bioavailability and underlying parameters such as clearance rate may also affect efficacy. Therefore, "improved efficacy" (for example, improvement in efficacy) may be attributed to improved pharmacokinetic parameters and improved efficacy, and may be measured by comparing parameters such as clearance rate and treatment or improvement of an autoimmune disease in a laboratory animal or human subject.

As used herein, the term "therapeutically effective amount" or "pharmaceutically effective amount" refers to an amount of a compound or composition effective for preventing or treating a target disease, and means an amount that is sufficient to treat a disease with a reasonable benefit/risk ratio applicable to medical treatment and does not cause side effects. The level of the effective amount may be determined according to the patient's health condition, the type and severity of the disease, the activity of the drug, the sensitivity to the drug, administration method, administration time, the route of administration and excretion rate, treatment duration, factors including the combined or concurrently used drugs, and other factors well known in the medical field. In one embodiment, a therapeutically effective amount refers to an amount of a drug effective to treat an autoimmune disease.

In this regard, the pharmaceutical composition may further comprise a pharmaceutically acceptable carrier. The pharmaceutically acceptable carrier may be any non-toxic material suitable for delivery to a patient. Distilled water, alcohol, fats, waxes and inert solids may be included as a carrier. In addition, a pharmaceutically acceptable adjuvant (buffer, dispersing agent) may be included in the pharmaceutical composition.

Specifically, the pharmaceutical composition may include a pharmaceutically acceptable carrier in addition to an active ingredient and may be prepared as a parenteral formulation according to the route of administration by a conventional method known in the art. Here, "pharmaceutically acceptable" means that it does not inhibit the activity of an active ingredient and does not have toxicity beyond what a subject to be applied (prescribed) may tolerate.

When the pharmaceutical composition is prepared as a parenteral formulation, it may be formulated in the form of injections, transdermal preparations, nasal inhalants and suppositories together with a suitable carrier according to methods known in the art. Formulation of a pharmaceutical composition is known in the art, and specifically, reference may be made to the literature [Remington's Pharmaceutical Sciences (19th ed., 1995)] and the like. The literature is considered a part of the present specification.

The preferred dosage of the pharmaceutical composition may vary depending on the condition, body weight, sex, and age of the patient, the severity of the disease, the route of administration, and the like, and may be appropriately selected by one of ordinary skill in the art.

A subject to which the pharmaceutical composition may be applied (prescribed) is a mammal and a human, particularly preferably a human.

In another aspect of the present disclosure, there is provided a method for treating an autoimmune disease, comprising administering an effective amount of an antibody or an antigen binding fragment thereof that specifically binds to FcRn to a patient in need of treatment for an autoimmune disease.

In another aspect of the present disclosure, there is provided a method for alleviating an autoimmune or alloimmune condition, comprising administering the anti-FcRn antibody or antigen binding fragment thereof to a subject in need thereof. In addition, there is provided a specific anti-FcRn therapy at the same time.

The method or anti-FcRn therapy for alleviating an autoimmune or alloimmune condition according to the present disclosure may be achieved by administering the pharmaceutical composition according to the present disclosure to a subject. The pharmaceutical composition according to the present disclosure may be administered orally or parenterally. For example, it may be administered via a route of administration such as intravenous injection, subcutaneous injection, intramuscular injection, intraperitoneal injection, topical administration, intranasal administration, intrapulmonary administration, and intrarectal administration. In some embodiments, the pharmaceutical composition disclosed herein is administered subcutaneously.

The preferred dosage of the pharmaceutical composition may vary depending on the condition and body weight of the patient, the severity of the disease, the form of the drug, the route and duration of administration, but may be appropriately selected by one of ordinary skill in the art, and may be administered once or repeatedly.

In various embodiments of the therapeutic methods and uses disclosed herein, the antibody or antigen-binding fragment is administered to a patient as a fixed dose. In various embodiments of the therapeutic methods and uses disclosed herein, the antibody or antigen-binding fragment is administered to a patient as a weight-based dose, i.e., a dose dependent on the patient's bodyweight. In various embodiments of the therapeutic methods and uses disclosed herein, the antibody or antigen-binding fragment is administered to a patient as a body surface area-based dose, i.e., a dose dependent on the patient's body surface area (BSA). In various embodiments, the dose administered to the patient comprises a therapeutically effective amount of the antibody or antigen-binding fragment.

In some embodiments, the antibody or antigen-binding fragment is administered to the patient at a dose of about 300 mg to about 500 mg. In some embodiments, the antibody or antigen-binding fragment is administered to the patient subcutaneously at a dose of about 300 mg to about 500 mg, e.g., once weekly, once monthly, or once every 2 weeks, or once every 3 weeks. In some embodiments, the antibody or antigen-binding fragment is administered (e.g., subcutaneously) to the patient at a dose of about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, or about 500 mg (e.g., once weekly, once monthly, once every two weeks, or once every three weeks). In some embodiments, the antibody or antigen-binding fragment is administered (e.g., subcutaneously) to the patient at a dose of at least or more than about 300 mg (e.g., once weekly, once monthly, or once every two weeks). In some embodiments, the antibody or antigen-binding fragment is administered to the patient at a dose of about 340 mg. In some embodiments, the antibody or antigen-binding fragment is administered to the patient at a dose of about 340 mg once weekly, once monthly, or once every 2 weeks. In some embodiments, the antibody or antigen-binding fragment is administered to the patient at a dose of about 340 mg once weekly. In some embodiments, the antibody or antigen-binding fragment is administered to the patient at a dose of about 340 mg once weekly as a single subcutaneous injection. In some embodiments, the antibody or antigen-binding fragment is administered to the patient at a dose of about 340 mg once weekly for at least 2 weeks (e.g., 2 weeks, 3 weeks, 4 weeks, 5 weeks, 6 weeks, 7 weeks, 8 weeks, 10 weeks, 12 weeks, or longer). In some embodiments, the antibody or antigen-binding fragment is administered to the patient at a dose of about 340 mg once weekly for at least 4 weeks. In some embodiments, the antibody or antigen-binding fragment is administered to the patient at a dose of about 340 mg once weekly for at least 7 weeks. In some embodiments, the antibody or antigen-binding fragment is administered to the patient at a dose of about 340 mg once weekly for at least 12 weeks. In some embodiments, the administration is subcutaneous.

In some embodiments, the antibody or antigen-binding fragment is administered to the patient at a dose of about 500 mg to about 700 mg. In some embodiments, the antibody or antigen-binding fragment is administered to the patient subcutaneously at a dose of about 500 mg to about 700 mg, e.g., once weekly, once monthly, once every two weeks, or once every three weeks. In some embodiments, the antibody or antigen-binding fragment is administered (e.g., subcutaneously) to the patient at a dose of about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, or about 700 mg (e.g., once weekly, once monthly, once every two weeks, or once every three weeks). In some embodiments, the antibody or antigen-binding fragment is administered (e.g., subcutaneously) to the patient at a dose of at most or less than about 750 mg or 700 mg (e.g., once weekly, once monthly, or once every two weeks). In some embodiments, the antibody or antigen-binding fragment is administered to the patient at a dose of about 680 mg. In some embodiments, the antibody or antigen-binding fragment is administered to the patient at a dose of about 680 mg once weekly, once monthly, or once every 2 weeks. In some embodiments, the antibody or antigen-binding fragment is administered to the patient at a dose of about 680 mg once weekly. In some embodiments, the antibody or antigen-binding fragment is administered to the patient at a dose of about 680 mg once weekly as two or more (e.g., two) consecutive subcutaneous injections. In some embodiments, the antibody or antigen-binding fragment is administered to the patient at a dose of about 680 mg once weekly for at least 2 weeks (e.g., 2 weeks, 3 weeks, 4 weeks, 5 weeks, 6 weeks, 7 weeks, 8 weeks, 10 weeks, 12 weeks, or longer). In some embodiments, the antibody or antigen-binding fragment is administered to the patient at a dose of about 680 mg once weekly for at least 4 weeks. In some embodiments, the antibody or antigen-binding fragment is administered to the patient at a dose of about 680 mg once weekly for at least 7 weeks. In some embodiments, the antibody or antigen-binding fragment is administered to the patient at a dose of about 680 mg once weekly for at least 12 weeks. In some embodiments, the administration is subcutaneous.

In some embodiments, the antibody or antigen-binding fragment is administered to the patient at a dose of about 100 mg, about 150 mg, about 200 mg, about 300 mg, about 400 mg, about 450 mg, about 500 mg, about 600 mg, about 700 mg, about 800 mg, about 900 mg, about 1000 mg, about 1100 mg, about 1,200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, or about 2500 mg. In some embodiments, the antibody or antigen-binding fragment is administered to the patient at a dose of about 100 mg, about 150 mg, about 200 mg, about 300 mg, about 400 mg, about 450 mg, about 500 mg, about 600 mg, about 700 mg, about 800 mg, about 900 mg, about 1000 mg, about 1100 mg, about 1,200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, or about 2500 mg intravenously. In some embodiments, the antibody or antigen-binding fragment is administered to the patient at a dose of about 100 mg, about 150 mg, about 200 mg, about 300 mg, about 400 mg, about 450 mg, about 500 mg, about 600 mg, about 700 mg, about 800 mg, about 900 mg, about 1000 mg, about 1100 mg, about 1,200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, or about 2500 mg subcutaneously.

In some embodiments, the antibody or antigen-binding fragment is administered to the patient at a dose range between any of the dose values referenced herein. In some embodiments, the antibody or antigen-binding fragment is administered to the patient at a dose which is less than any of the dose values referenced herein.

In some embodiments, the antibody or antigen-binding fragment is administered to the patient at a dose of about 100 mg, about 150 mg, about 200 mg, about 300 mg, about 400 mg, about 450 mg, about 500 mg, about 600 mg, about 700 mg, about 800 mg, about 900 mg, about 1000 mg, about 1100 mg, about 1,200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, or about 2500 mg once weekly (e.g., subcutaneously).

In some embodiments, the antibody or antigen-binding fragment is administered to the patient at a dose of about 100 mg, about 150 mg, about 200 mg, about 300 mg, about 400 mg, about 450 mg, about 500 mg, about 600 mg, about 700 mg, about 800 mg, about 900 mg, about 1000 mg, about 1100 mg, about 1,200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, or about 2500 mg once every two weeks (e.g., subcutaneously).

In some embodiments, the antibody or antigen-binding fragment is administered to the patient at a dose of about 100 mg, about 150 mg, about 200 mg, about 300 mg, about 400 mg, about 450 mg, about 500 mg, about 600 mg, about 700 mg, about 800 mg, about 900 mg, about 1000 mg, about 1100 mg, about 1,200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, or about 2500 mg once every three weeks (e.g., subcutaneously).

In some embodiments, the antibody or antigen-binding fragment is administered to the patient at a dose of about 100 mg, about 150 mg, about 200 mg, about 300 mg, about 400 mg, about 450 mg, about 500 mg, about 600 mg, about 700 mg, about 800 mg, about 900 mg, about 1000 mg, about 1100 mg, about 1,200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, or about 2500 mg once monthly (e.g., subcutaneously).

In some embodiments, the antibody or antigen-binding fragment is administered to the patient at a dose of about 300 mg, about 600 mg, about 900 mg, about 1200 mg, about 1500 mg, about 1800 mg, about 2100 mg or about 2400 mg. In some embodiments, the antibody or antigen-binding fragment is administered to the patient at a dose of about 300 mg, about 600 mg, about 900 mg, about 1200 mg, about 1500 mg, about 1800 mg, about 2100 mg or about 2400 mg intravenously. In some embodiments, the antibody or antigen-binding fragment is administered to the patient at a dose of about 300 mg, about 600 mg, about 900 mg, about 1200 mg, about 1500 mg, about 1800 mg, about 2100 mg or about 2400 mg subcutaneously. In some embodiments, the antibody or antigen-binding fragment is administered to the patient at a dose of about 300 mg, about 600 mg, about 900 mg, about 1200 mg, about 1500 mg, about 1800 mg or about 2100 mg once weekly (e.g., subcutaneously). In some embodiments, the antibody or antigen-binding fragment is administered to the patient at a dose of about 300 mg, about 600 mg, about 900 mg, about 1200 mg, about 1500 mg, about 1800 mg, about 2100 mg or about 2400 mg once every two weeks (e.g., subcutaneously). In some embodiments, the antibody or antigen-binding fragment is administered to the patient at a dose of about 300 mg, about 600 mg, about 900 mg, about 1200 mg, about 1500 mg, about 1800 mg, about 2100 mg or about 2400 mg once every three weeks (e.g., subcutaneously). In some embodiments, the antibody or antigen-binding fragment is administered to the patient at a dose of about 300 mg, about 600 mg, about 900 mg, about 1200 mg, about 1500 mg, about 1800 mg, about 2100 mg or about 2400 mg once monthly (e.g., subcutaneously).

In some embodiments, the antibody is administered (e.g., subcutaneously) to the patient at a dose of about 150 mg, about 300 mg, about 450 mg, about 600 mg, about 900 mg, about 1200 mg, about 1500 mg, about 1800 mg, about 2100 mg, or about 2400 mg, or at any dose in between any two of these doses (e.g., administered at this dose once weekly subcutaneously, once in two weeks subcutaneously, once in three weeks subcutaneously, or once monthly subcutaneously). In some embodiments, the doses provided herein are suitable doses for administration to a human.

In some embodiments, the antibody, antigen-binding fragment, or pharmaceutical composition is administered to the patient once weekly or once monthly. In some embodiments, the antibody, antigen-binding fragment, or pharmaceutical composition is administered to the patient once weekly for at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 12 weeks, at least 20 weeks, at least 24 weeks, at least 30 weeks, at least 40 weeks, at least 50 weeks, at least 60 weeks, at least 70 weeks, at least 76 weeks, at least 80 weeks, or longer.

In some embodiments, the antibody, antigen-binding fragment, or pharmaceutical composition is administered to the patient once in about two or three weeks. In some embodiments, the antibody, antigen-binding fragment, or pharmaceutical composition is administered to the patient once every other week (i.e., once in two weeks) for at least 2 weeks, at least 4 weeks, at least 6 weeks, at least 8 weeks, at least 10 weeks, at least 12 weeks, at least 20 weeks, at least 24 weeks, at least 30 weeks, at least 40 weeks, at least 50 weeks, at least 60 weeks, at least 70 weeks, at least 76 weeks, at least 80 weeks, or longer.

In some embodiments, the antibody, antigen-binding fragment, or pharmaceutical composition is administered to the patient once in 3 weeks for at least 3 weeks, at least 6 weeks, at least 9 weeks, at least 12 weeks, at least 18 weeks, at least 21 weeks, at least 24 weeks, at least 30 weeks, at least 42 weeks, at least 48 weeks, at least 60 weeks, at least 72 weeks, at least 78 weeks, at least 81 weeks, or longer.

In some embodiments, the antibody, antigen-binding fragment, or pharmaceutical composition is administered to the patient once monthly for at least 1 month, at least 2 months, at least 3 months, at least 4 months, at least 5 months, at least 6 months, at least 7 months, at least 8 months, at least 9 months, at least 10 months, at least 12 months, at least 20 months, at least 24 months, at least 30 months, at least 40 months, at least 50 months, at least 60 months, at least 70 months, at least 76 months, at least 80 months, or longer.

In some embodiments, the antibody, antigen-binding fragment, or pharmaceutical composition is administered to the patient once weekly for 6 to 76 weeks, or any time period in between. In some embodiments, the antibody, antigen-binding fragment, or pharmaceutical composition is administered to the patient once weekly for at least 2 weeks, at least 3 weeks, at least 4 weeks, or at least 6 weeks. In some embodiments, the antibody, antigen-binding fragment, or pharmaceutical composition is administered to the patient once weekly for at least 4 weeks. In some embodiments, the antibody, antigen-binding fragment, or pharmaceutical composition is administered to the patient once weekly for at least 7 weeks. In some embodiments, the antibody, antigen-binding fragment, or pharmaceutical composition is administered to the patient once weekly for at least 12 weeks. In some embodiments, the antibody, antigen-binding fragment, or pharmaceutical composition is administered to the patient once weekly for at least 24 weeks. In some embodiments, the antibody, antigen-binding fragment, or pharmaceutical composition is administered to the patient once weekly for at least 52 weeks.

In some embodiments, the antibody or antigen-binding fragment is administered to the patient at one or more doses (e.g., two or more different doses). For example, in some embodiments, the antibody or antigen-binding fragment is administered to the patient at two different doses, e.g., at least one higher dose, followed by at least one lower dose. A higher dose (e.g., a higher dose of two different doses) may be referred to herein as an "induction" dose, i.e., a dose capable of reducing the level of at least one autoantibody and/or pathogenic antibody (e.g., at least one IgG) in a patient and/or a sample from a patient. A lower dose (e.g., a lower dose of two different doses) may be referred to herein as a "maintenance" dose, i.e., a dose capable of maintaining the reduced level of at least one autoantibody and/or pathogenic antibody (e.g., at least one IgG) in the patient and/or a sample from the patient following at least one induction dose of an antibody or antigen-binding fragment (e.g., about 20-80% of pretreatment (pre-induction dose) values). In some embodiments, a maintenance dose maintains the level of at least one autoantibody and/or pathogenic antibody (e.g., at least one IgG) in the patient and/or a sample from the patient at about or less than 20%, about 25%, about 30%, about 35%, about 40%, about 45%, about 50%, about 55%, about 60%, about 65%, about 70%, about 75%, or about 80% of pretreatment (pre-induction dose) values.

In some embodiments, the induction dose and the maintenance dose are alternated, e.g., the patient may receive the induction dose for a first period of time followed by the maintenance dose for a first period of time, followed by the induction dose for a second period of time, optionally followed by the maintenance dose for a second period of time. In some embodiments, the cycle of induction and maintenance dose (administration of the induction dose for a period of time followed by administration of the maintenance dose for a period of time being one cycle) is repeated one twice, three times, four times, five times, six times seven times, or ten times. In some embodiments, the cycle of induction and maintenance dose is repeated for about 3 months, about 6 months, about 12 months, about 15 moths, about 18 months, about 24 months, or longer.

In some embodiments, at least one higher dose and/or induction dose is about 680 mg per dose or more (e.g., about 680 mg, about 700 mg per dose, about 720 mg per dose, about 750 mg per dose, or more). In some embodiments, the at least one higher dose and/or induction dose is about one dose, about 2 doses, about 3 doses, about 4 doses, or about 5 doses at about 680 mg per dose or more (e.g., about 680 mg, about 700 mg, about 720 mg per dose, about 750 mg per dose, or more). In some embodiments, the at least one higher dose and/or induction dose is about 3 doses at about 680 mg per dose or more (e.g., about 680 mg, about 700 mg per dose, about 720 mg per dose, about 750 mg per dose, or more).

In some embodiments, the at least one higher dose and/or induction dose is administered to the patient once, once weekly, once every 2 weeks, or once monthly. In some embodiments, the at least one higher dose and/or induction dose is administered to the patient intravenously. In some embodiments, the at least one higher dose and/or induction dose is administered to the patient subcutaneously. In some embodiments, each higher dose is administered to the patient as one or more subcutaneous injections. In some embodiments, each higher dose is administered to the patient as two consecutive subcutaneous injections.

In some embodiments, at least one lower dose and/or maintenance dose is about 340 mg per dose or more (e.g., about 340 mg, about 360 mg, about 380 mg, about 400 mg per dose or more). In some embodiments, the at least one lower dose and/or maintenance dose is about one dose, about 2 doses, about 3 doses, about 4 doses, or about 5 doses at about 340 mg per dose or more (e.g., about 340 mg, about 360 mg, about 380 mg, about 400 mg per dose or more). In some embodiments, the at least one lower dose and/or maintenance dose is about 3 doses at about 340 mg per dose or more (e.g., about 340 mg, about 360 mg, about 380 mg, about 400 mg per dose or more). In some embodiments, the at least one lower dose and/or maintenance dose is administered to the patient once, once weekly, once every 2 weeks, or once monthly. In some embodiments, the at least one lower dose and/or maintenance dose is administered to the patient subcutaneously. In some embodiments, each lower dose is administered to the patient as one or more subcutaneous injections. In some embodiments, each lower dose is administered to the patient as one subcutaneous injection.

EXAMPLES

Hereinafter, the present disclosure will be described in more detail by way of the following examples. However, the following examples are only for illustrating the present disclosure, and the scope of the present disclosure is not limited thereto.

I. Design of Variants to Improve Physical Properties of HL161AN Antibody

For the purpose of improving stability through molecular engineering of HL161AN, Lonza's in silico tool and LC-MS/MS analysis were used to identify amino acid sites that could affect stability and to design variants. A schematic of the in silico design of the HL161AN variants is shown in FIG. 1.

Therapeutic proteins, including antibodies, are present in a heterogeneous form due to post-translational modification (PTM) and chemical modification. Modification includes glycosylation, deamidation, oxidation, and the like, and is known to occur depending on the host cell system, production process, storage conditions, and the like. This modification is considered to be a major challenge during the production process of therapeutic proteins as it causes side effects such as decreased efficacy, limited shelf life, and immune response due to aggregation (De Groot 2006).

HL161AN is an anti-hFcRn antibody in the form of modified human $IgG_1$ that has a high affinity for human FcRn ($2\times10^{-10}$ M) and has a high PD effect in an in vivo study on cynomolgus monkeys. However, it has disadvantages that it has low thermal stability (about 58.4° C.), aggregation occurs at a concentration of 30 mg/mL or more, and many charge variants are identified in CEX-HPLC and cIEF analysis. Therefore, we found the PTM site and the major site for aggregation using an in silico tool based on the amino acid sequence and X-ray crystal structure analysis results, and we identified the modified site through LC-MS/MS analysis of the HL161AN sample. Thereafter, by combining the two results, we tried to design a variant that may reduce the risk of PTM and aggregation.

Example 1. In Silico Evaluation of Aggregation Risk and PTM Risk

The risk of aggregation and post-translational modification were predicted through in silico analysis.

The aggregation of proteins is affected by environmental factors such as pH, concentration, buffer, excipient, shear-force, and the like, and intrinsic properties. In order to predict the risk of aggregation according to the amino acid sequence, Lonza's Sentinel APART™ database was used. This is a program validated based on the experimental results on the aggregation of more than 500 antibodies. When the sequence of the tested antibody is input, the risk of aggregation is predicted. The Sentinel APART algorithm predicted that HL161AN would have an increased aggregation risk.

Figure 2:
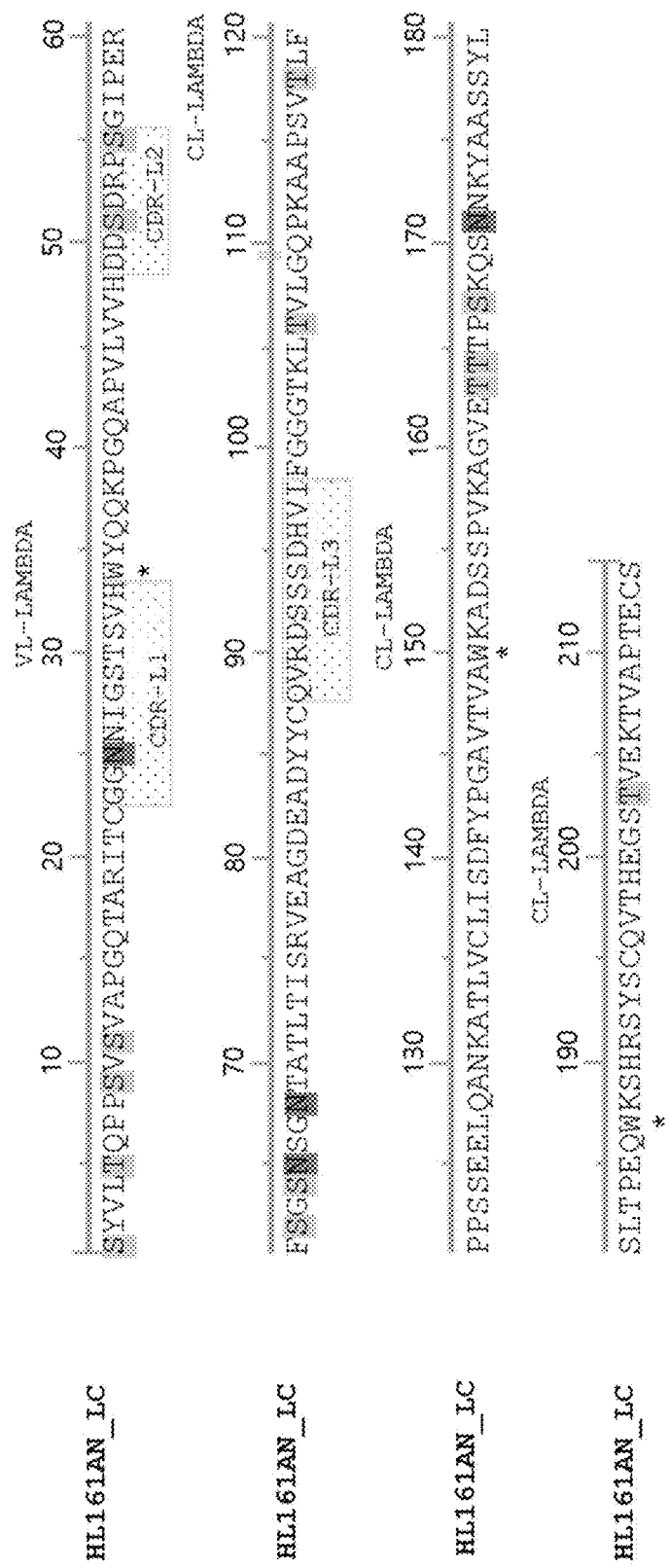
FIG. 2 is a drawing showing the predicted post-translational modification (PTM) site of the HL161AN light chain (SEQ ID NO: 19).

In addition, using the in silico tool developed by Lonza, the post-translational modification (PTM) as described below was predicted (FIGS. 2 and 3). Specifically, the risk of the post-translational modification was performed in consideration of i) asparagine deamidation, ii) aspartic acid isomerization and fragmentation, iii) C-terminal lysine clipping, iv) Fc ADCC/CDC response, half-life and Protein A purification, v) free cysteine thiol group, vi) N-glycosylation, O-glycosylation, vii) oxidation, and viii) pyroglutamate formation, and the like.

As a result of the HL161AN amino acid sequence analysis, the possibility of asparagine deamidation was predicted at 4 sites of the light chain (L) and 12 sites of the heavy chain (H). Most of them were conserved asparagines and were predicted to be low-risk, and 4 sites had the possibility of deamidation, but did not correspond to the CDR regions, so it was confirmed that protein engineering was not required. Accordingly, it was analyzed that only L:Asn25 of the light chain CDR region required protein engineering.

In addition, a free cysteine thiol group results in protein misfolding, aggregation, non-specific tissue binding, immunogenicity, and potentially low productivity. As a result of confirming whether HL161AN has a free cysteine thiol group, a free thiol group was found in H:Cys32, and it was determined that protein engineering of this amino acid was necessary.

Example 2. Analysis of PTM Site Through LC-MS/MS Analysis

Figure 4:
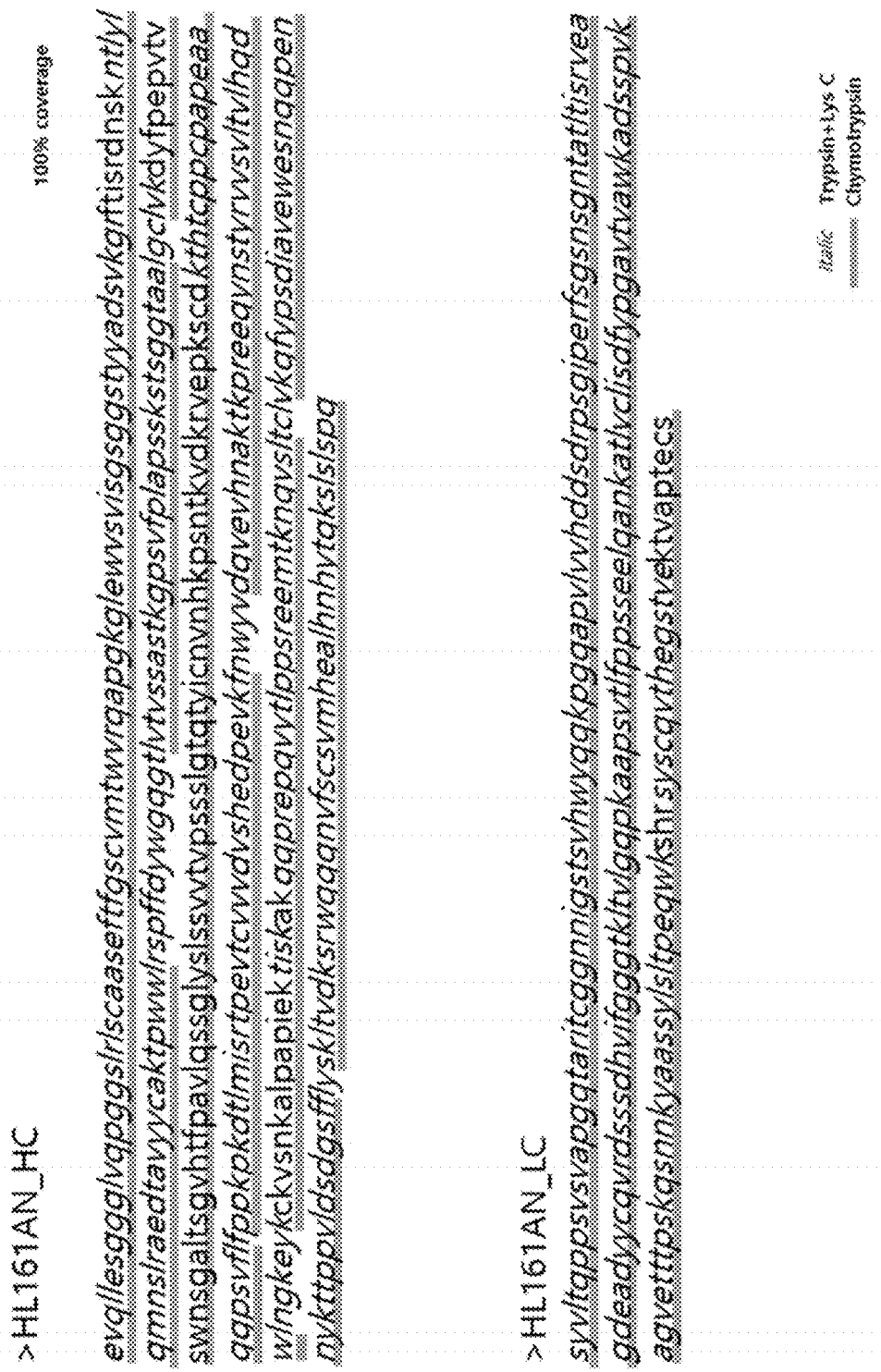
FIG. 4 is a drawing showing 100% sequence coverage confirmed by treating a HL161AN in-house standard sample obtained from the HL161AN-producing cell line (#8G7) with two enzymes, trypsin+Lys C mix and chymotrypsin, respectively. HL161AN HC comprises the sequence of SEQ ID NO: 20 and LH161AN LC comprises the sequence of SEQ ID NO: 19.

The modification of deamidation and oxidation for 2 lots of HL161AN were analyzed by LC-MS/MS. As a result of peptide mapping using two enzymes, i.e., trypsin+Lys C mix and chymotrypsin, 100% sequence coverage was confirmed (FIG. 4).

As a result of modification analysis, deamidation and oxidation were confirmed at 7 and 6 sites in the HL161AN in-house standard sample, respectively, and at 10 and 8 sites in the HL161AN B012 sample, respectively.

The deamidation and oxidation sites of the HL161AN sample by LC-MS/MS are summarized and shown in Tables 2 and 3, respectively, below.

TABLE 2

| Site | In-house standard sample | HL161AN B012 |
|---|---|---|
| L: Asn25 | ✓ | |
| L: Gln36 | | ✓ |
| L: Gln37 | | ✓ |
| L: Asn130 | | ✓ |
| H: Asn74 | ✓ | |
| H: Gln82 | ✓ | |
| H: Asn84 | | ✓ |
| H: Gln113 | ✓ | ✓ |
| H: Asn280 | | ✓ |
| H: Asn319 | ✓ | ✓ |
| H: Gln351 | | ✓ |
| H: Asn388 | ✓ | ✓ |
| H: Gln390 | | ✓ |
| H: Gln422 | ✓ | |
| Total | 7 | 10 |

TABLE 3

| Site | In-house standard sample | HL161AN B012 |
|---|---|---|
| L: Trp34 | ✓ | ✓ |
| L: Trp197 | | ✓ |
| H: Met34 | ✓ | ✓ |
| H: Met83 | ✓ | ✓ |
| H: Trp102 | | ✓ |
| H: Met256 | ✓ | ✓ |
| H: Asn319 | ✓ | ✓ |
| H: Asn388 | ✓ | ✓ |
| Total | 6 | 8 |

Example 3. Selection of Sites to be Engineered

Based on the in silico analysis results and LC-MS/MS results, the substitution amino acids for the three amino acid sites (L:Asn25, H:Cys32, H:Gln82) that are determined to require engineering were selected. From the X-ray crystallography structure analysis data, these three amino acid sites are far from the CDR region binding to the target antigen, so it was determined that the substitution would not affect the affinity (FIG. 5). In the selection of substitution of amino acids, it was determined that substitution with serine (Ser) or glutamine (Gln) for L:Asn25; serine (Ser) or tyrosine (Tyr) for H:Cys32; and serine (Ser), threonine (Thr), or glutamic acid (Glu) for H:Gln82 could reduce the risk of PTM™. For each amino acid selection method, a chemically similar side chain substitution method was used, such as replacing asparagine with glutamine (Table 4). Based on these results, 2 light chains and 11 heavy chains were designed (Table 5).

The suggested substitutions of the selected PTM sites are summarized and shown in Table 4 below, and the designed variants of HL161AN are summarized and shown in Table 5 below.

TABLE 4

| Selected PTM site | Suggested substitution | Description |
|---|---|---|
| L: Asn25 | glutamine | Conservative substitution |
| | | However, glutamine does not occur naturally at this site. |
| | serine | An alternative to glutamine is a neutral substitution for the small and preferably polar side chain. |

TABLE 4-continued

| Selected PTM site | Suggested substitution | Description |
| --- | --- | --- |
| H: Cys32 | serine | The side chain of serine is most similar to the side chain of cysteine. |
| | tyrosine | Tyrosine is primarily based on commonly identified sequence alignments. |
| H: Gln82 | glutamic acid | Similar side chain<br>However, the introduction of a negative charge affects the isoelectric point and thus may affect the potency. |
| | serine | The rotamer of serine shows better side chain hydrogen bonding possibility. |
| | threonine | Beta branched side chain of threonine has better beta-strand possibility, which may show better stability. |

TABLE 5

| Chain name | Description |
| --- | --- |
| Light chain | |
| HL161AN_LC_1 | L: N25S |
| HL161AN_LC_2 | L: N25Q |
| Heavy chain | |
| HL161AN_HC_1 | H: C32S |
| HL161AN_HC_2 | H: C32Y |
| HL161AN_HC_3 | H: Q82S |
| HL161AN_HC_4 | H: Q82T |
| HL161AN_HC_5 | H: Q82E |
| HL161AN_HC_6 | H: C32S, H: Q82S |
| HL161AN_HC_7 | H: C32S, H: Q82T |
| HL161AN_HC_8 | H: C32S, H: Q82E |
| HL161AN_HC_9 | H: C32Y, H: Q82S |
| HL161AN_HC_10 | H: C32Y, H: Q82T |
| HL161AN_HC_11 | H: C32Y, H: Q82E |

Combining the above series of results, it is as described below.

For the purpose of improving stability through molecular engineering of HL161AN, Lonza's in silico tool and LC-MS/MS analysis were used to identify amino acid sites that could affect stability and to design variants through mutations.

As a result, it was determined that the three amino acid sites (L:Asn25, H:Cys32, H:Gln82) of the HL161AN antibody required engineering. It was determined that substitution with serine or glutamine for L:Asn25; serine or tyrosine for H:Cys32; and serine, threonine, or glutamic acid for H:Gln82 could reduce the risk of PTM. A total of 22 HL161AN variants (2 light chains and 11 heavy chains of HL161AN variants) were designed by amino acid substitution.

Hereinafter, 22 variants were prepared by a site-directed mutagenesis method, and then antibodies with improved stability were screened through in vitro and in vivo evaluations.

II. In Vitro Screening of HL161AN Antibody Variants

HL161AN has excellent in vitro/in vivo pharmacological efficacy, but has disadvantages that it has poor physicochemical properties, so storage stability is poor, and high concentration SC (subcutaneous) formulation is difficult. In order to improve this, sites that could affect the stability of the antibody were determined as described above through the amino acid sequence and molecular structure analysis of HL161AN, and a total of 22 HL161AN variants were prepared by engineering the derived amino acid sites (Table 6). Hereinafter, in vitro evaluation was performed by producing 22 obtained HL161AN variants.

Preparation Example 1. Preparation of Test Materials

Preparation Example 1.1. HL161AN Reference Standard Sample (Reference Standard, RS): Control 1

Lot No: HL161AN/16E11/STO1

Concentration: 13 mg/mL

Formulation buffer: 100 mM histidine, 100 mM arginine-HCl, pH 6.0

Storage condition: ≤−60° C.

Preparation Example 1.2. HL161AN Variant Plasmid 2 light chain mutations and 11 heavy chain mutations Storage condition: ≤−60° C.

In the amino acid sequence of HL161AN, two or more amino acids were substituted as shown in Table 6 below.

TABLE 6

| Variant No. | Light chain | Heavy chain |
| --- | --- | --- |
| 1 | N25S | C32S |
| 2 | | C32Y |
| 3 | | Q82S |
| 4 | | Q82T |
| 5 | | Q82E |
| 6 | | C32SQ82S |
| 7 | | C32SQ82T |
| 8 | | C32SQ82E |
| 9 | | C32YQ82S |
| 10 | | C32YQ82T |
| 11 | | C32YQ82E |
| 12 | N25Q | C32S |
| 13 | | C32Y |
| 14 | | Q82S |
| 15 | | Q82T |
| 16 | | Q82E |
| 17 | | C32SQ82S |
| 18 | | C32SQ82T |
| 19 | | C32SQ82E |
| 20 | | C32YQ82S |
| 21 | | C32YQ82T |
| 22 | | C32YQ82E |

Example 4. First In Vitro Evaluation of 22 HL161AN Variants

22 HL161AN variants were evaluated in comparison with the control antibody HL161AN.

Example 4.1. Production of Samples

One day before transfection, Expi293F cells were seeded in a 500 mL Erlenmeyer flask at 1×10⁶ cells/mL (100 mL volume) and then incubated in an incubator of 8% $CO_2$, 125 rpm, 37° C. conditions for 24 hours while shaking. On the day of transfection, the cell concentration was adjusted to 2×10⁶ cells/mL, and then the cells were transfected with the plasmid DNA of each variant. The antibody plasmid was diluted to 1 μg/L in LAL water (Lonza Bioscience). 0.12 mL of the heavy chain plasmid and 0.12 mL of the light chain plasmid were added to 5 mL of Opti-MEM SFM, respectively, and suspended. 0.24 mL of FectoPro was added to 5 mL of Opti-MEM SFM and suspended.

The plasmid DNA and FectoPro were mixed 1:1 and incubated at room temperature for 10 minutes, and then added to the flask containing the cells. It was incubated in an incubator of 8% $CO_2$, 37° C. conditions at 125 rpm for 3 hours while shaking, and then 100 μL of Booster was added to continue the culture. On the 6th day of culture, the culture solution was placed in a 250 mL centrifuge bottle and centrifuged at 3,000 rpm, for 15 minutes, and then only the supernatant was collected and filtered through a 0.2 μm bottle top filter. The expression level of the antibody in the recovered culture medium was quantified using a Cedex bioanalyzer.

As a result, a total of 22 HL161AN antibody variants were transiently expressed using Expi293F cells. Transfection was carried out on a 100 mL culture scale to obtain an expression medium in an amount of 0.5 mg or more for each antibody, and the culture medium was harvested on the 6th day. The expression level in the obtained medium was 65-181 mg/L (Table 7). The production results for 22 HL161AN variants are summarized and shown in Table 7 below.

TABLE 7

| Variant No. | Expression level (mg/L) | Purification IgG (mg) | Purity (SEC-HPLC, %) |
|---|---|---|---|
| 1 | 81 | 3.6 | 99.2 |
| 2 | 94 | 6.0 | 98.0 |
| 3 | 88 | 1.8 | 97.4 |
| 4 | 105 | 5.7 | 97.3 |
| 5 | 91 | 4.7 | 96.8 |
| 6 | 142 | 8.3 | 99.0 |
| 7 | 116 | 7.2 | 98.8 |
| 8 | 119 | 5.0 | 97.6 |
| 9 | 116 | 7.0 | 99.2 |
| 10 | 88 | 9.0 | 99.3 |
| 11 | 117 | 7.2 | 99.4 |
| 12 | 181 | 10.0 | 99.0 |
| 13 | 97 | 10.0 | 99.7 |
| 14 | 99 | 5.3 | 97.4 |
| 15 | 114 | 6.2 | 97.4 |
| 16 | 138 | 7.3 | 97.5 |
| 17 | 65 | 4.0 | 98.8 |
| 18 | 93 | 4.0 | 99.0 |
| 19 | 89 | 6.0 | 99.0 |
| 20 | 105 | 4.5 | 99.3 |
| 21 | 114 | 7.5 | 99.7 |
| 22 | 81 | 10.7 | 98.3 |

Example 4.2. Purification of Antibodies

The purification of the sample was carried out by packing 1.5 mL of MabSelect SuRe™ LX resin into a Poly-prep® chromatography column. 1×PBS (pH 7.4) was used as the binding buffer and the washing buffer, and the elution was carried out by fractionation by 1.5 mL using a 0.1 M glycine (pH 3.0) buffer. All fraction tubes were neutralized to pH 7.0 by adding 1 M Tris-HCl (pH 9.0) and then pooled. The pooled eluent was purified by buffer exchange with a citrate phosphate buffer (pH 8.0) and concentration to 1.0 mg/mL using a Millipore centricon (cutoff of 30 kDa). HL161AN RS was also used for in vitro evaluation by buffer exchange with a citrate phosphate buffer (pH 8.0) in the same manner as the HL161AN variant. For each sample, the A280 value was measured using a Nanodrop, and the concentration was calculated. Based on the quantitative value, for each antibody, the status of the sample was confirmed by SDS-PAGE analysis.

Figure 6:
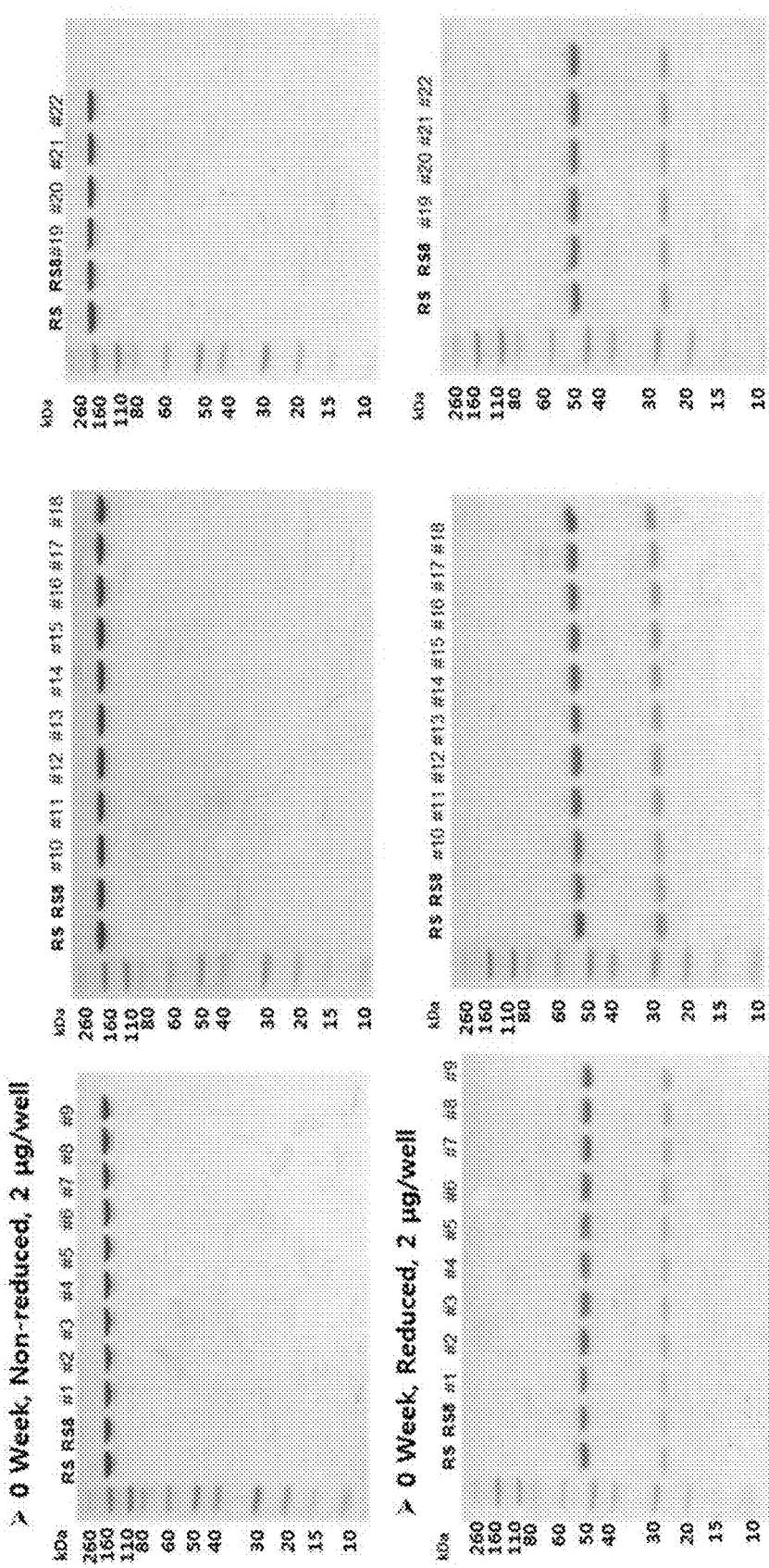
FIG. 6 is a drawing showing the SDS-PAGE results of the HL161AN variants.

As a result, the culture solution obtained by transiently expressing a total of 22 HL161AN antibody variants using Expi293F cells was purified by a Protein A column and concentrated to a concentration of 1.0 mg/mL. It was confirmed that the produced sample had a purity of 97% or more by SDS-PAGE and SEC-HPLC analysis (FIG. 6 and Table 7).

Example 4.3. SPR Analysis

SPR (Surface plasmon resonance) analysis was performed under two conditions of pH 6.0 and pH 7.4 using Proteon XPR36 equipment. shFcRn (soluble human FcRn) was immobilized on a GLC chip, and the antibody samples were reacted at 5 concentrations, and then the sensogram results were obtained. Kinetic analysis was performed using a 1:1 Langmuir binding model, and the average KD value was obtained by repeating the analysis 6 times in each condition of pH 6.0 and pH 7.4.

Chip activation was performed under EDAC/NHS 0.5×, 30 μL/min, and 300 sec conditions. Thereafter, shFcRn was prepared at 2 μg/mL, 250 μL using an acetate buffer (pH 5.5), and immobilization was performed while flowing at 30 μL/min. The reaction was stopped when the immobilization level corresponded to 200 RU to 300 RU. Thereafter, deactivation was performed using ethanolamine at 30 μL/min, 300 sec. The antibody samples were prepared by serial dilution by ½ to 5 nM, 2.5 nM, 1.25 nM, 0.625 nM, and 0.312 nM based on a concentration of 10 nM. Sample dilution was performed using 1×PBST (pH 7.4) or 1×PBST (pH 6.0) buffer depending on the analysis pH. In the sample analysis conditions, association was carried out by reaction at 50 μL/min, 200 sec, and dissociation was carried out by reaction at 50 μL/min, 600 sec. Thereafter, reaction was carried out using a glycine buffer (pH 2.0) at 100 μL/min, 18 sec to perform regeneration. For kinetic analysis, samples were prepared and reacted once in three cells to which shFcRn was immobilized. Then three kinetic values were obtained, and then an average KD value was measured.

When analyzing reaction signals, interspot-referencing and signals in which only buffer was analyzed were used for a double-referencing.

Figure 7:
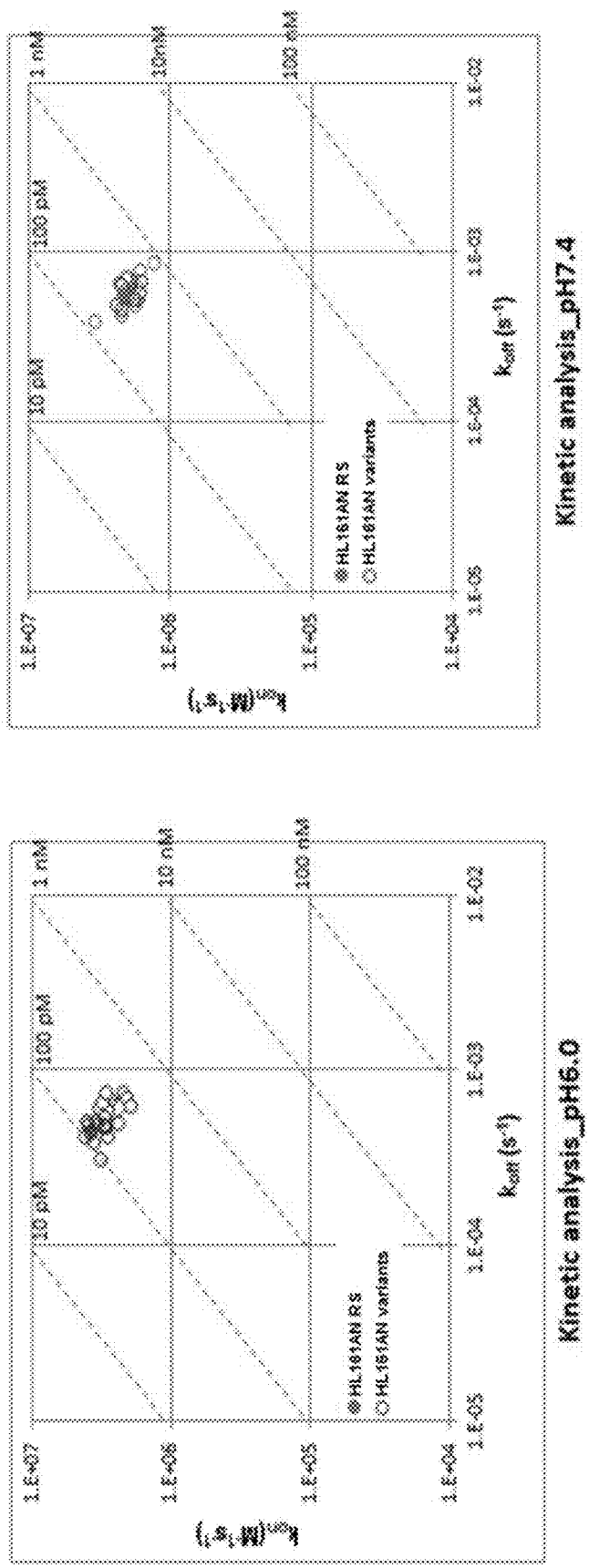
FIG. 7 is a drawing showing the SPR results of the HL161AN variants.

As described above, SPR analysis was performed on 22 HL161AN antibody variants at pH 6.0 and pH 7.4. As a result, the HL161AN variants exhibited a similar binding affinity compared to a binding affinity of HL161AN to shFcRn (1.16E-10 M (at pH 6.0) and 2.94E-10 M (at pH 7.4)) (FIG. 7 and Table 8).

The kinetic results of the HL161AN variants are summarized and shown in Table 8 below.

TABLE 8

| Variant No. | LC | HC | pH 6.0 | | | | pH 7.4 | | | |
| | | | Ka (1/Ms) | Kd (1/s) | KD (M) | % CV | Ka (1/Ms) | Kd (1/s) | KD (M) | % CV |
|---|---|---|---|---|---|---|---|---|---|---|
| HL161AN | — | — | 3.32E+06 | 3.84E-04 | 1.16E-10 | 9% | 1.84E+06 | 5.42E-04 | 2.94E-10 | 36% |
| 1 | N25S | C32S | 3.58E+06 | 4.63E-04 | 1.29E-10 | 17% | 3.22E+06 | 3.92E-04 | 1.22E-10 | 16% |
| 2 | N25S | C32Y | 2.91E+06 | 4.33E-04 | 1.49E-10 | 37% | 2.10E+06 | 4.35E-04 | 2.07E-10 | 12% |
| 3 | N25S | Q82S | 3.40E+06 | 4.91E-04 | 1.45E-10 | 47% | 2.22E+06 | 4.42E-04 | 1.99E-10 | 18% |
| 4 | N25S | Q82T | 3.01E+06 | 4.69E-04 | 1.56E-10 | 34% | 2.04E+06 | 4.91E-04 | 2.40E-10 | 16% |
| 5 | N25S | Q82E | 2.46E+06 | 5.63E-04 | 2.29E-10 | 45% | 1.17E+06 | 7.43E-04 | 6.37E-10 | 21% |
| 6 | N25S | C32SQ82S | 3.39E+06 | 5.52E-04 | 1.63E-10 | 33% | 1.50E+06 | 6.87E-04 | 4.59E-10 | 11% |
| 7 | N25S | C32SQ82T | 3.28E+06 | 4.98E-04 | 1.52E-10 | 33% | 2.32E+06 | 4.32E-04 | 1.87E-10 | 15% |
| 8 | N25S | C32SQ82E | 3.02E+06 | 4.77E-04 | 1.58E-10 | 24% | 2.27E+06 | 4.96E-04 | 2.18E-10 | 27% |
| 9 | N25S | C32YQ82S | 2.85E+06 | 5.05E-04 | 1.77E-10 | 42% | 2.04E+06 | 4.99E-04 | 2.45E-10 | 16% |
| 10 | N25S | C32YQ82T | 2.80E+06 | 5.73E-04 | 2.05E-10 | 48% | 1.93E+06 | 4.94E-04 | 2.56E-10 | 34% |
| 11 | N25S | C32TQ82E | 2.56E+06 | 4.86E-04 | 1.90E-10 | 35% | 1.86E+06 | 4.87E-04 | 2.62E-10 | 6% |
| 12 | N25Q | C32S | 3.02E+06 | 5.49E-04 | 1.81E-10 | 35% | 2.38E+06 | 4.99E-04 | 2.09E-10 | 1% |
| 13 | N25Q | C32Y | 2.77E+06 | 5.56E-04 | 2.00E-10 | 26% | 1.88E+06 | 4.44E-04 | 2.36E-10 | 28% |
| 14 | N25Q | Q82S | 2.68E+06 | 5.58E-04 | 2.08E-10 | 43% | 1.95E+06 | 5.51E-04 | 2.83E-10 | 20% |
| 15 | N25Q | Q82T | 2.27E+06 | 6.01E-04 | 2.65E-10 | 35% | 1.84E+06 | 5.13E-04 | 2.79E-10 | 24% |
| 16 | N25Q | Q82E | 2.05E+06 | 5.56E-04 | 2.71E-10 | 38% | 1.86E+06 | 5.04E-04 | 2.72E-10 | 46% |
| 17 | N25Q | C32SQ82S | 3.19E+06 | 5.38E-04 | 1.69E-10 | 30% | 2.27E+06 | 5.66E-04 | 2.49E-10 | 35% |
| 18 | N25Q | C32SQ82T | 2.84E+06 | 5.62E-04 | 1.98E-10 | 32% | 2.39E+06 | 5.42E-04 | 2.26E-10 | 37% |
| 19 | N25Q | C32SQ82E | 2.09E+06 | 5.75E-04 | 2.75E-10 | 33% | 2.12E+06 | 4.89E-04 | 2.30E-10 | 47% |
| 20 | N25Q | C32YQ82S | 2.54E+06 | 5.09E-04 | 2.00E-10 | 47% | 1.98E+06 | 5.60E-04 | 2.83E-10 | 40% |
| 21 | N25Q | C32YQ82T | 2.67E+06 | 5.52E-04 | 2.06E-10 | 29% | 2.39E+06 | 4.99E-04 | 2.09E-10 | 38% |
| 22 | N25Q | C32TQ82E | 1.98E+06 | 5.22E-04 | 2.64E-10 | 42% | 1.70E+06 | 6.47E-04 | 3.81E-10 | 21% |

Example 4.4. Analysis of hFcRn Binding of Antibody Variants Using FACS

The analysis of hFcRn binding using FACS was carried out under two conditions of pH 6.0 and pH 7.4. hFcRn-expressing 1TEK293 (hFcRn HEK293) cells were diluted with the reaction buffer (0.0500 BSA in PBS, pH 6.0 or pH 7.4) and prepared in duplicate in a 96 well plate at $1\times10^5$ cells for each sample. In addition, each antibody sample was diluted with the reaction buffer to 10 nM, and then put into a 96 well plate, and incubated at 4° C. for 90 minutes. Thereafter, the plate was centrifuged to remove the supernatant, and then Alexa488-goat anti-hIgG Ab (1:200) was added thereto, and again incubated at 4° C. for 90 minutes. After the reaction was completed, it was centrifuged to remove the supernatant, and 200 μL of the reaction buffer was added to resuspend the cell pellet, and then the MFI value was measured in a FACS instrument.

Figure 8:
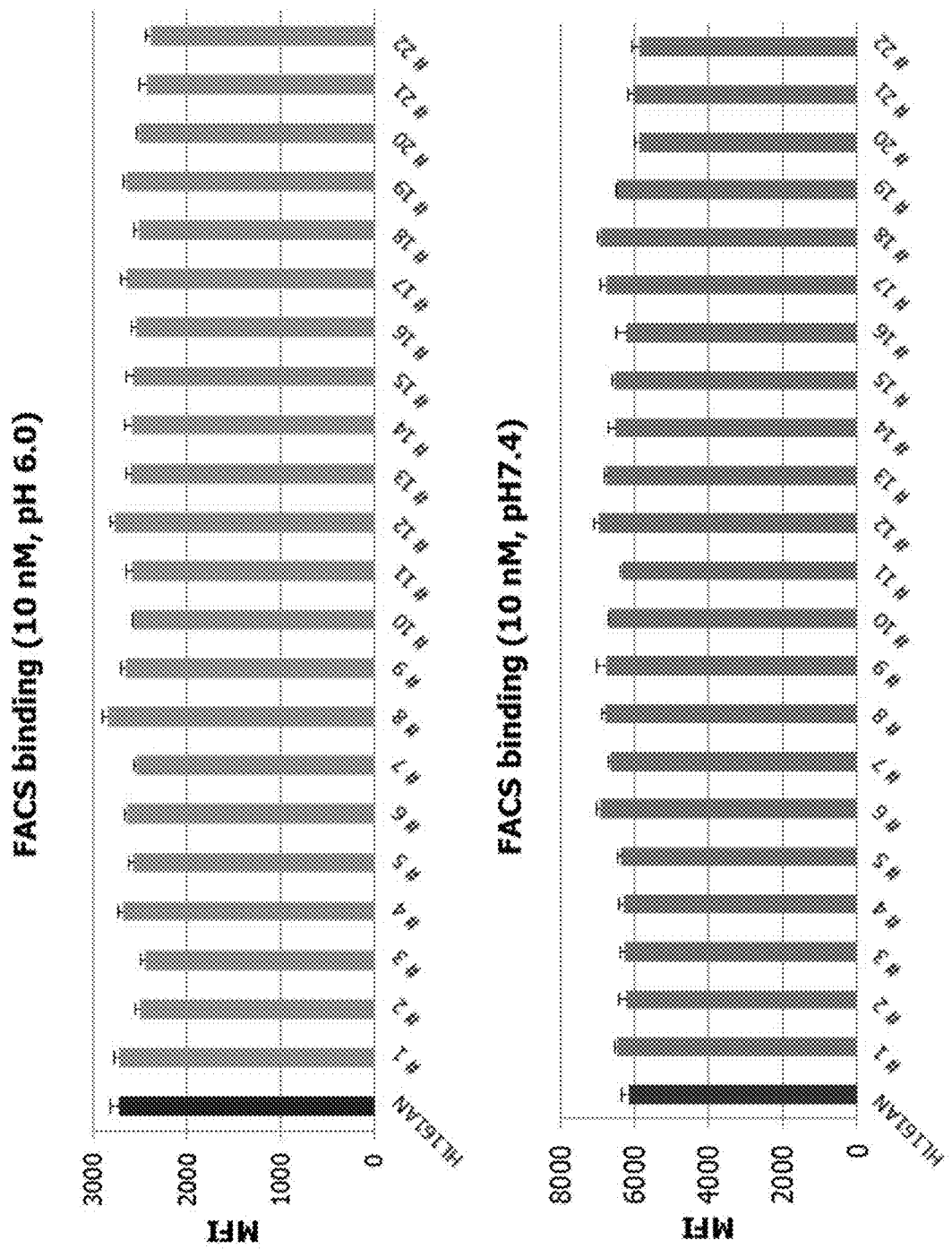
FIG. 8 is a drawing showing the results obtained by confirming the binding of the HL161AN variants and hFcRn using FACS.

As described above, binding evaluation using FACS was carried out for 22 HL161AN antibody variants at pH 6.0 and pH 7.4. As a result, 22 HL161AN variants exhibited MFI values similar to those of HL161AN (FIG. 8).

Example 4.5. Analysis of hFcRn Blocking Ability of Antibodies Using FACS $1\times10^7$ hFcRn HEK293 cells were seeded into a T75 flask and cultured for 24 hours. After culturing, the cells were removed and placed in a 96 well plate at $1\times10^5$ cells for each sample in duplicate. Thereafter, each antibody sample (0.2, 2, 20, and 200 nM) and 100 nM Alexa488-hIgG1 were added in a 1:1 ratio and incubated at 4° C. for 90 minutes. After the reaction was completed, it was centrifuged to remove the supernatant. 200 μL of the reaction buffer was added to resuspend the cell pellet, and then the MFI value was measured in a FACS instrument. Each MFI value was converted into % blocking, and the $EC_{50}$ value was obtained by fitting with 4-PL.

Figure 9:
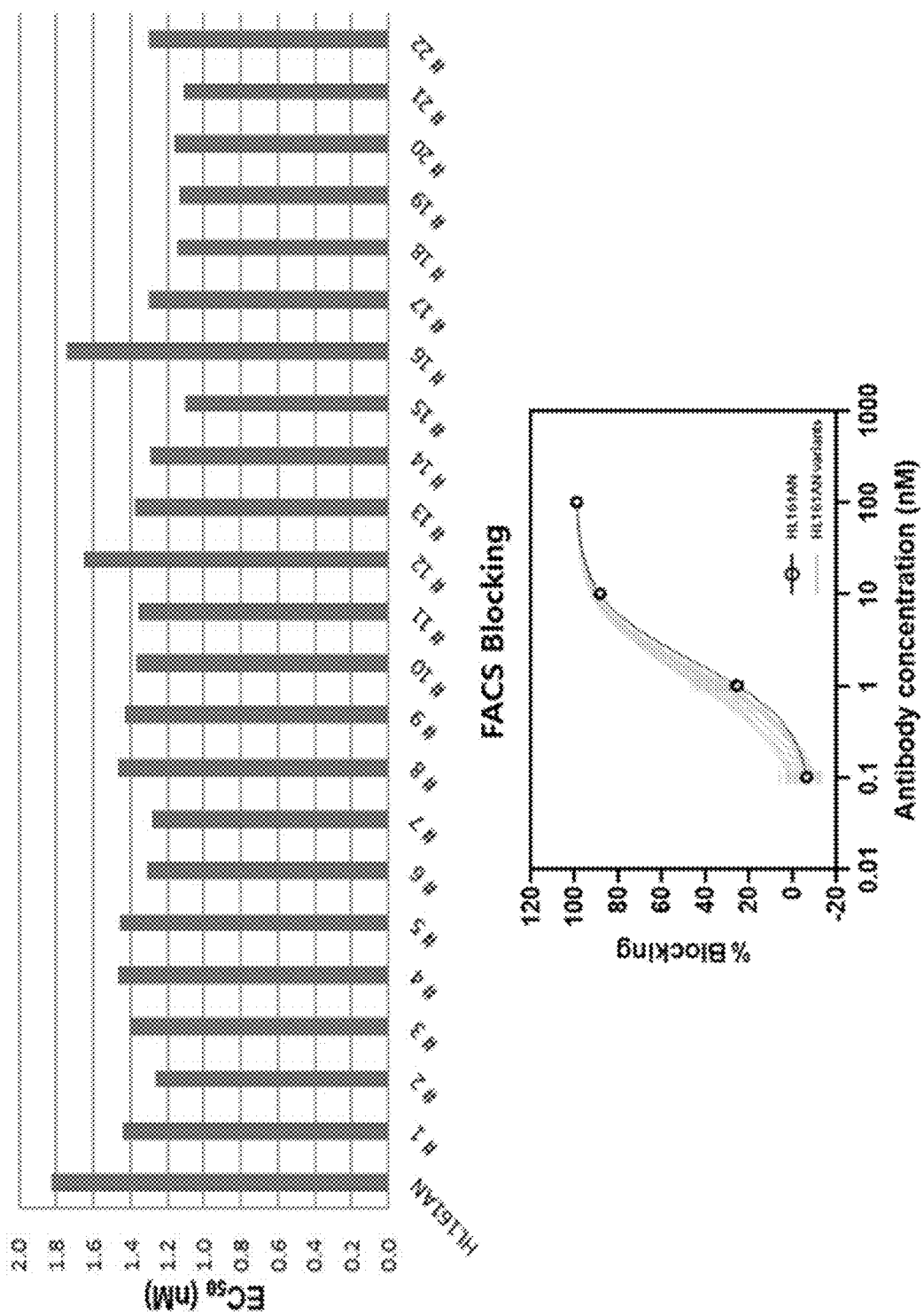
FIG. 9 is a drawing showing the results obtained by confirming the effect of the HL161AN variants to block hFcRn using FACS.

As a result, blocking evaluation using FACS was carried out at 0.1 nM, 1 nM, 10 nM, and 100 nM. Each antibody blocked in a concentration-dependent manner, and it was confirmed that the $EC_{50}$ values were similar. Similar to the results of hFcRn binding analysis using FACS, it was confirmed that the $EC_{50}$ values of 22 HL161AN variants were similar to those of the control antibody HL161AN. Accordingly, it was determined that the amino acid substitution did not affect the function of the HL161AN variants (FIG. 9).

Example 4.6. Evaluation of Stability

200 μL of the purified sample was each aliquoted into a 1.5 mL tube, and then the samples were stored under accelerated conditions at 40° C. for up to 4 weeks, and the samples at weeks 0, 1, 2, and 4 were analyzed by SEC-HPLC. Analysis of each sample was performed under the SEC-HPLC analysis conditions shown in Table 9 below, and the degree of stability under accelerated conditions was analyzed.

TABLE 9

| | |
|---|---|
| Column | TSK G3000SWXL |
| Mobile phase | 0.2M potassium phosphate, 0.25M potassium chloride, pH 6.2 |
| Temperature | column 25° C., sample 4° C. |
| UV detection | 214 nm |
| Injection volume | 100 Ml |
| Flow rate | 0.5 mL/min |
| Run time | 30 minutes |

Figure 10:
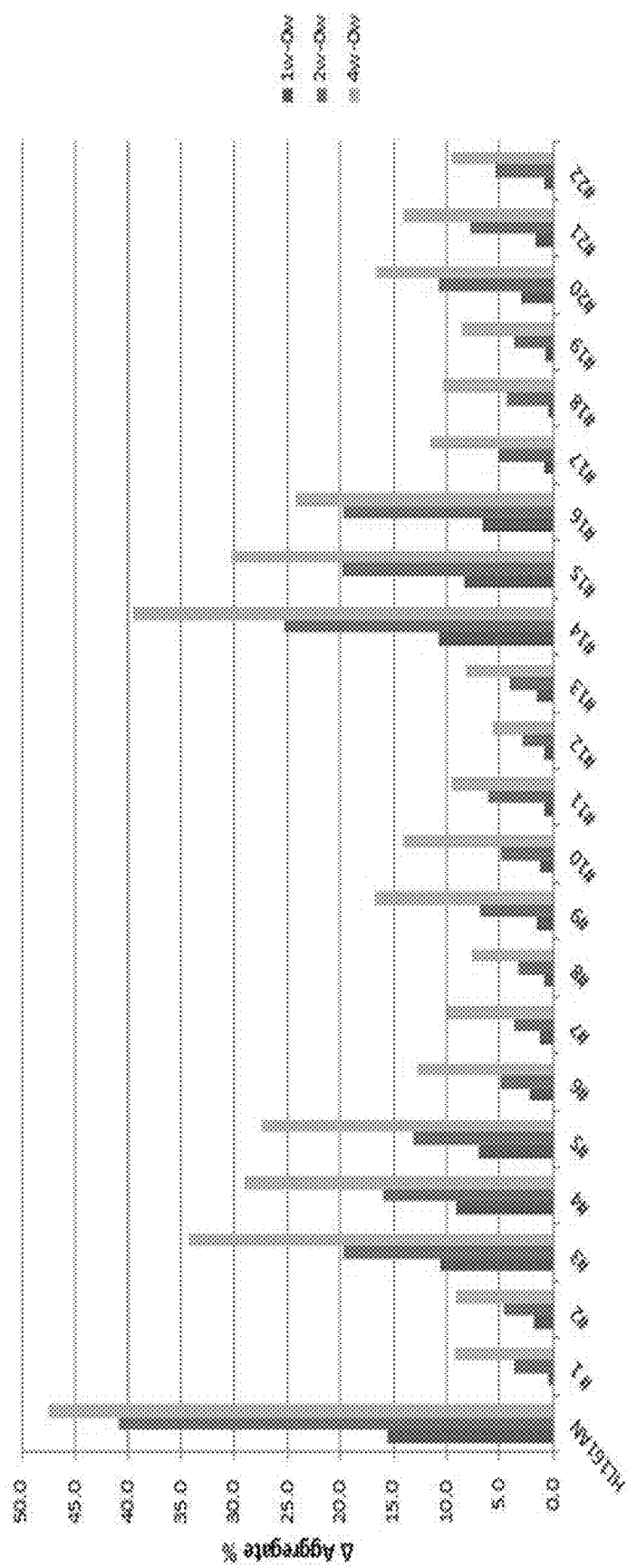
FIG. 10 is a drawing showing the degree of increase in aggregates of the HL161AN variant (1 mg/mL) in a stability test performed under accelerated conditions at 40° C.
Figure 11:
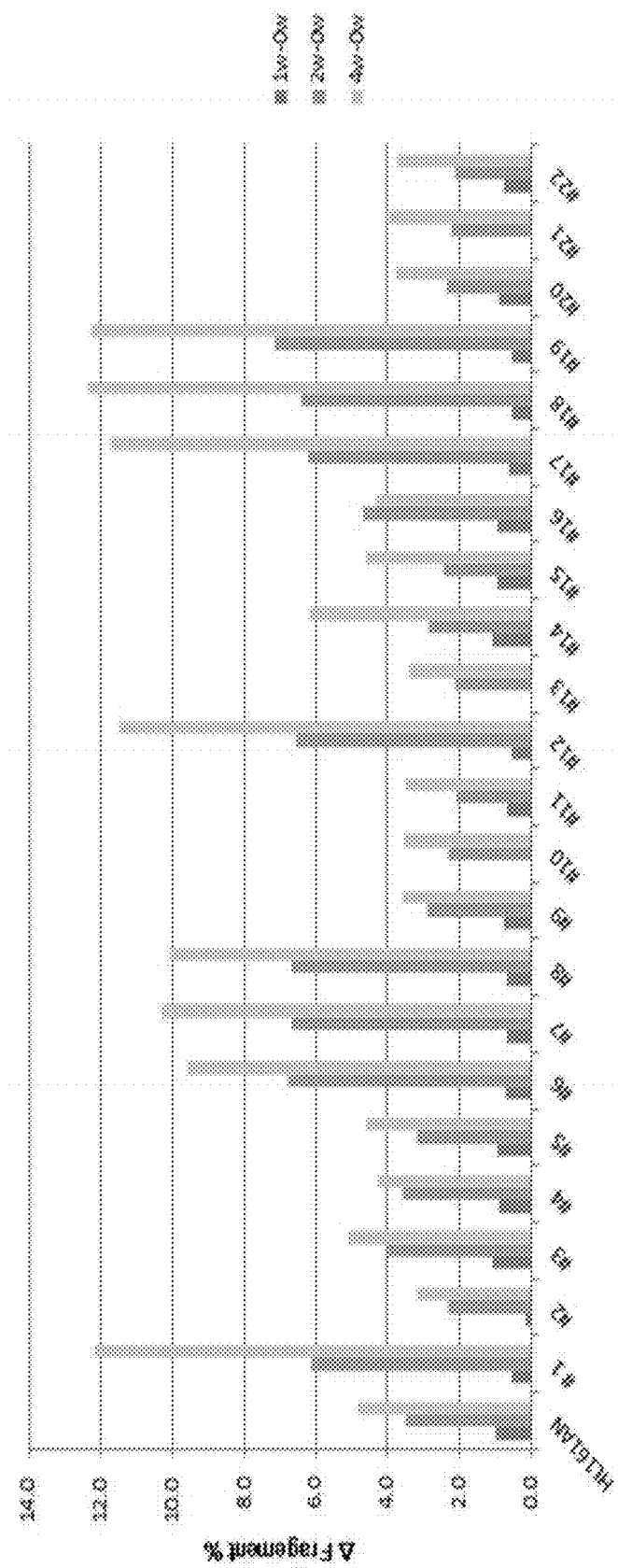
FIG. 11 is a drawing showing the degree of increase in fragments of the HL161AN variant (1 mg/mL) in a stability test performed under accelerated conditions at 40° C.

The samples were stored under accelerated conditions at 40° C. for up to 4 weeks and the stability of the samples was analyzed by SEC-HPLC. As a result, in the case of HL161AN, aggregates were increased by 47.5% and fragments were increased by 4.80% in the sample at week 4 compared to the sample at week 0. On the other hand, the production rate of aggregates of 22 variants was 5.6% to 39.6%, which was reduced compared to HL161AN, and the production rate of fragments was 3.2% to 12.3% which was increased or similar to that of HL161AN (FIG. 10, FIG. 11, and Table 10).

TABLE 10

| Variant No. | Δaggregates (% area) | | | Δmain peak (% area) | | | Δfragments (% area) | | |
|---|---|---|---|---|---|---|---|---|---|
| | 1 w | 2 w | 4 w | 1 w | 2 w | 4 w | 1 w | 2 w | 4 w |
| HL161AN | 15.6 | 40.9 | 47.5 | −16.6 | −44.5 | −52.3 | 1.0 | 3.5 | 4.8 |
| 1 | 0.5 | 3.7 | 9.3 | −1.1 | −9.8 | −21.5 | 0.5 | 6.1 | 12.2 |
| 2 | 1.8 | 4.6 | 9.2 | −2.0 | −6.8 | −12.4 | 0.2 | 2.3 | 3.2 |
| 3 | 10.6 | 19.7 | 34.2 | −11.7 | −23.7 | −39.3 | 1.1 | 4.0 | 5.1 |
| 4 | 9.1 | 15.9 | 29.0 | −10.0 | −19.5 | −33.2 | 0.9 | 3.6 | 4.3 |
| 5 | 7.0 | 13.2 | 27.4 | −8.0 | −16.3 | −32.0 | 0.9 | 3.2 | 4.6 |
| 6 | 2.2 | 4.8 | 12.8 | −2.5 | −11.5 | −22.4 | 0.7 | 6.8 | 9.6 |
| 7 | 1.3 | 3.6 | 10.0 | −1.9 | −10.2 | −20.3 | 0.7 | 6.7 | 10.3 |
| 8 | 0.9 | 3.3 | 7.7 | −1.6 | −10.0 | −17.8 | 0.7 | 6.7 | 10.1 |
| 9 | 1.5 | 6.9 | 16.7 | −2.2 | −9.8 | −20.3 | 0.7 | 2.9 | 3.6 |
| 10 | 1.3 | 4.9 | 14.1 | −1.3 | −7.9 | −17.6 | 0.0 | 2.3 | 3.5 |
| 11 | 0.8 | 6.1 | 9.6 | −1.5 | −8.2 | −13.1 | 0.7 | 2.1 | 3.5 |
| 12 | 0.8 | 2.8 | 5.6 | −1.3 | −9.4 | −17.1 | 0.5 | 6.6 | 11.5 |
| 13 | 1.5 | 4.1 | 8.2 | −1.5 | −6.2 | −11.6 | 0.0 | 2.1 | 3.4 |
| 14 | 10.8 | 25.3 | 39.6 | −11.9 | −28.1 | −45.8 | 1.1 | 2.9 | 6.2 |
| 15 | 8.4 | 19.8 | 30.3 | −9.3 | −22.3 | −34.9 | 0.9 | 2.5 | 4.6 |
| 16 | 6.6 | 19.7 | 24.3 | −7.5 | −24.4 | −28.7 | 0.9 | 4.7 | 4.3 |
| 17 | 0.9 | 5.1 | 11.6 | −1.6 | −11.3 | −23.3 | 0.6 | 6.2 | 11.7 |
| 18 | 0.4 | 4.3 | 10.3 | −0.9 | −10.7 | −22.6 | 0.5 | 6.4 | 12.3 |
| 19 | 0.7 | 3.6 | 8.6 | −1.2 | −10.7 | −20.9 | 0.5 | 7.2 | 12.3 |
| 20 | 3.0 | 10.7 | 16.6 | −3.9 | −13.0 | −20.4 | 0.9 | 2.3 | 3.8 |
| 21 | 1.7 | 7.8 | 14.1 | −1.7 | −10.0 | −18.1 | 0.0 | 2.2 | 4.0 |
| 22 | 0.8 | 5.4 | 9.6 | −1.5 | −7.5 | −13.4 | 0.8 | 2.1 | 3.7 |

Example 4.7. DSC Analysis

Differential scanning calorimetry (DSC) analysis was carried out using NANO DSC instrument (TA Instrument, PN: 602000, SN: K10126), and the Tm values were analyzed with a two-state scaled model using NanoAnalyze software. DSC analysis was carried out by K Bio Health (Osong Medical Innovation Foundation, New Drug Development Support Center).

The thermal stability of the HL161AN variants was analyzed. As a result, as shown in Table 11 below, the Tm value of HL161AN was 58.4° C. and the Tm values of the HL161AN variants were 60° C. to 61.5° C. Therefore, it was confirmed that the Tm values of the HL161AN variants were increased by up to 2° C. compared to HL161AN.

The thermal stability of the HL161AN variants is summarized and shown in Table 11 below.

TABLE 11

| Variant No. | Fab Tm (° C.) |
|---|---|
| HL161AN | 58.4 |
| 1 | 60.8 |
| 2 | 59.9 |
| 8 | 61.2 |
| 11 | 60.1 |
| 12 | 61.4 |
| 13 | 60.4 |
| 19 | 61.5 |
| 22 | 60.4 |

The results of the first in vitro evaluation of 22 HL161AN variants described above are summarized and shown in Table 12 below.

Evaluation of FcRn binding affinity/blocking and stability was carried out for a total of 22 HL161AN variants. As a result, it was confirmed that the binding affinity and blocking effect were similar to those of HL161AN, and all HL161AN variants had improved stability in terms of the production of aggregates compared to HL161AN. Accordingly, the top eight variants that had the reduced production rate of aggregates of less than 10% when stored under 40° C. conditions for 4 weeks were selected, and it was decided to select the final lead molecule after preparing a high concentration sample and performing the second in vitro screening.

TABLE 12

| Variant no. | LC | HC | Exp.[1] | SPR[2] (KD, nM) | | FACS binding (10 nM, MFI) | | FACS binding (EC50, nM) | Stability accelerated conditions[3] | | | Selection of lead mol. |
|---|---|---|---|---|---|---|---|---|---|---|---|---|
| | | | | pH 6.0 | pH 7.4 | pH 6.0 | pH 7.4 | pH 6.0 | 1 w-0 w | 2 w-0 w | 4 w-0 w | |
| HL161AN | N25 | C32 | ++ | 0.10 | 0.27 | 2718 | 6147 | 1.83 | 15.6 | 40.9 | 47.5 | ○ |
| 12 | N25Q | C32S | +++ | 0.18 | 0.21 | 2767 | 6944 | 1.65 | 0.8 | 2.8 | 5.6 | ○ |
| 8 | N25S | C32SQ82E | ++ | 0.14 | 0.28 | 2832 | 6763 | 1.47 | 0.9 | 3.3 | 7.7 | ○ |
| 13 | N25Q | C32Y | + | 0.21 | 0.32 | 2596 | 6732 | 1.38 | 1.5 | 4.1 | 8.2 | ○ |
| 19 | N25Q | C32SQ82E | + | 0.32 | 0.36 | 2639 | 6474 | 1.14 | 0.7 | 3.6 | 8.6 | ○ |
| 2 | N25S | C32Y | + | 0.10 | 0.20 | 2497 | 6200 | 1.27 | 1.8 | 4.6 | 9.2 | ○ |
| 1 | N25S | C32S | + | 0.12 | 0.12 | 2722 | 6464 | 1.44 | 0.5 | 3.7 | 9.3 | ○ |
| 11 | N25S | C32YQ82E | ++ | 0.14 | 0.28 | 2584 | 6319 | 1.36 | 0.8 | 6.1 | 9.6 | ○ |
| 22 | N25Q | C32YQ82E | + | 0.21 | 0.30 | 2394 | 5861 | 1.30 | 0.8 | 5.4 | 9.6 | ○ |
| 7 | N25S | C32SQ82T | ++ | 0.11 | 0.21 | 2547 | 6621 | 1.28 | 1.3 | 3.6 | 10.0 | |
| 18 | N25Q | C32SQ82T | + | 0.25 | 0.33 | 2521 | 6911 | 1.15 | 0.4 | 4.3 | 10.3 | |
| 17 | N25Q | C32SQ82S | + | 0.22 | 0.30 | 2638 | 6750 | 1.30 | 0.9 | 5.1 | 11.6 | |
| 6 | N25S | C32SQ82S | ++ | 0.13 | 0.47 | 2646 | 6925 | 1.31 | 2.2 | 4.8 | 12.8 | |
| 10 | N25S | C32YQ82T | + | 0.15 | 0.36 | 2575 | 6659 | 1.37 | 1.3 | 4.9 | 14.1 | |
| 21 | N25Q | C32YQ82T | ++ | 0.18 | 0.30 | 2431 | 6026 | 1.11 | 1.7 | 7.8 | 14.1 | |
| 20 | N25Q | C32YQ82S | + | 0.17 | 0.35 | 2516 | 5844 | 1.16 | 3.0 | 10.7 | 16.6 | |
| 9 | N25S | C32YQ82S | ++ | 0.16 | 0.29 | 2658 | 6752 | 1.43 | 1.5 | 6.9 | 16.7 | |
| 16 | N25Q | Q82E | ++ | 0.33 | 0.43 | 2537 | 6209 | 1.74 | 6.6 | 19.7 | 24.3 | |

TABLE 12-continued

| Variant no. | LC | HC | Exp.[1] | SPR[2] (KD, nM) pH 6.0 | SPR[2] (KD, nM) pH 7.4 | FACS binding (10 nM, MFI) pH 6.0 | FACS binding (10 nM, MFI) pH 7.4 | FACS binding (EC$_{50}$, nM) pH 6.0 | Stability accelerated conditions[3] 1 w-0 w | Stability accelerated conditions[3] 2 w-0 w | Stability accelerated conditions[3] 4 w-0 w | Selection of lead mol. |
|---|---|---|---|---|---|---|---|---|---|---|---|---|
| 5 | N25S | Q82E | + | 0.16 | 0.67 | 2566 | 6350 | 1.46 | 7.0 | 13.2 | 27.4 | |
| 4 | N25S | Q82T | ++ | 0.11 | 0.27 | 2689 | 6299 | 1.47 | 9.1 | 15.9 | 29.0 | |
| 15 | N25Q | Q82T | ++ | 0.33 | 0.36 | 2569 | 6538 | 1.10 | 8.4 | 19.8 | 30.3 | |
| 3 | N25S | Q82S | + | 0.10 | 0.21 | 2445 | 6238 | 1.40 | 10.6 | 19.7 | 34.2 | |
| 14 | N25Q | Q82S | + | 0.20 | 0.35 | 2587 | 6487 | 1.29 | 10.8 | 25.3 | 39.6 | |

[1]Transient expression level of Expi293F, >150 mg/L (+++), 100-150 mg/L (++), <100 mg/L (+)
[2]hFcRn was immobilized on a chip and reacted with an antibody.
[3]Increase rate (%) of aggregates at pH 8.0 and 40° C. by SEC-HPLC

Example 5. Second In Vitro Evaluation of High Concentration Samples of Eight HL161AN Variants The eight high concentration HL161AN variants and the control antibody HL161AN were evaluated.

Example 5.1. Production of Samples

The culture method for producing a high concentration sample is the same as the method of Example 4.1, and in order to obtain 120 mg or more of the antibody, 1 L or more for each antibody variant was cultured.

Example 5.2. Purification of Antibodies

The purification method of the sample is the same as in Example 4.2, and the eluent was buffer exchanged with a 50 mM histidine buffer (pH 5.0) and concentrated to a concentration of about 150 mg/mL to complete purification. In the case of HL161AN RS, in the same manner as in the HL161AN variants the eluent was buffer exchanged with a 50 mM histidine (pH 5.0) and concentrated to a concentration of about 150 mg/mL to obtain the sample. For each antibody sample, the concentration was calculated using a Nanodrop, and SDS-PAGE analysis was performed based on this to confirm the sample status.

Example 5.3. Production of High Concentration Samples of HL161AN Variants

The eight HL161AN variants selected in the first in vitro evaluation were transiently expressed in Expi293F cells in the same manner as in Example 5.1 and Example 5.2 above and purified to prepare to a concentration of 150 mg/mL or more. HL161AN was used by concentrating the standard product to a high concentration. All samples were analyzed by A280 and SEC-HPLC after production (Table 13), and it was confirmed that all samples except for variant No. 2 and variant No. 13 had high purity of 98% or more. In the case of variant No. 2 and variant No. 13, precipitate was observed during the concentration process, and the SEC-HPLC purity was confirmed to be as low as about 93% (Table 13).

TABLE 13

| Variant No. | A280 (mg/mL) | SEC-HPLC (%) |
|---|---|---|
| HL161AN | 152.6 | 98.7 |
| 1 | 149.6 | 98.8 |
| 2 | 153.5 | 92.9 |
| 8 | 161.7 | 98.7 |

TABLE 13-continued

| Variant No. | A280 (mg/mL) | SEC-HPLC (%) |
|---|---|---|
| 11 | 161.3 | 98.9 |
| 12 | 157.9 | 98.6 |
| 13 | 158.1 | 93.1 |
| 19 | 163.2 | 98.9 |
| 22 | 161.3 | 98.9 |

Example 5.4. Analysis of hFcRn Binding of Antibodies Using FACS

Figure 12:
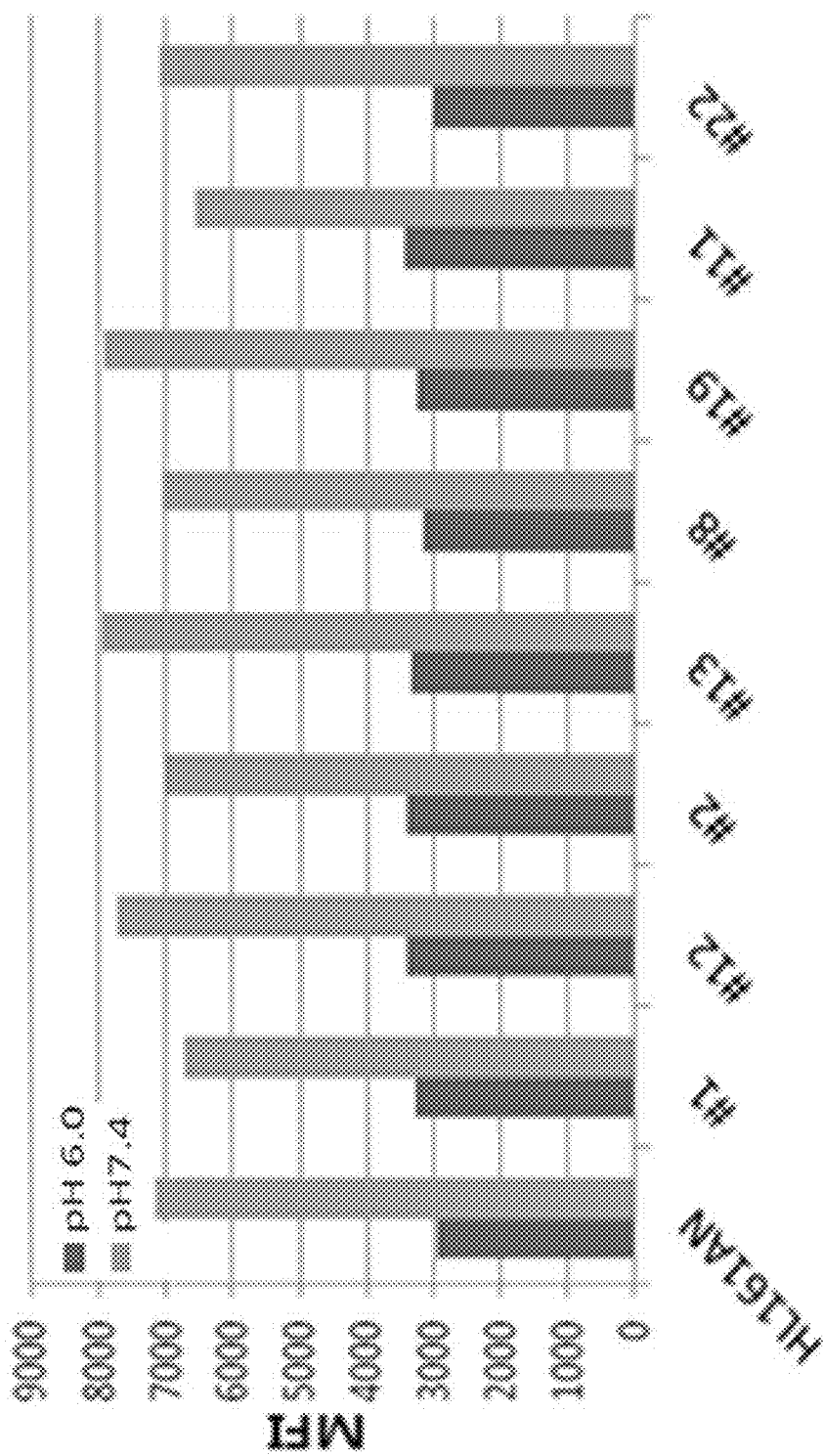
FIG. 12 is a drawing showing the results obtained by confirming the binding of hFcRn and the eight high concentration HL161AN variants selected after the first in vitro screening using FACS.

It was performed in the same manner as in Example 4.4. For the eight high concentration HL161AN variants and HL161AN, the evaluation of hFcRn binding was performed at pH 6.0 and pH 7.4 using FACS. As a result, the eight HL161AN variants showed the MFI values similar to those of HL161AN (pH 6.0: 2952, pH 7.4: 7155) (FIG. 12).

Example 5.5. Analysis of hFcRn Blocking of Antibodies Using FACS

Figure 13:
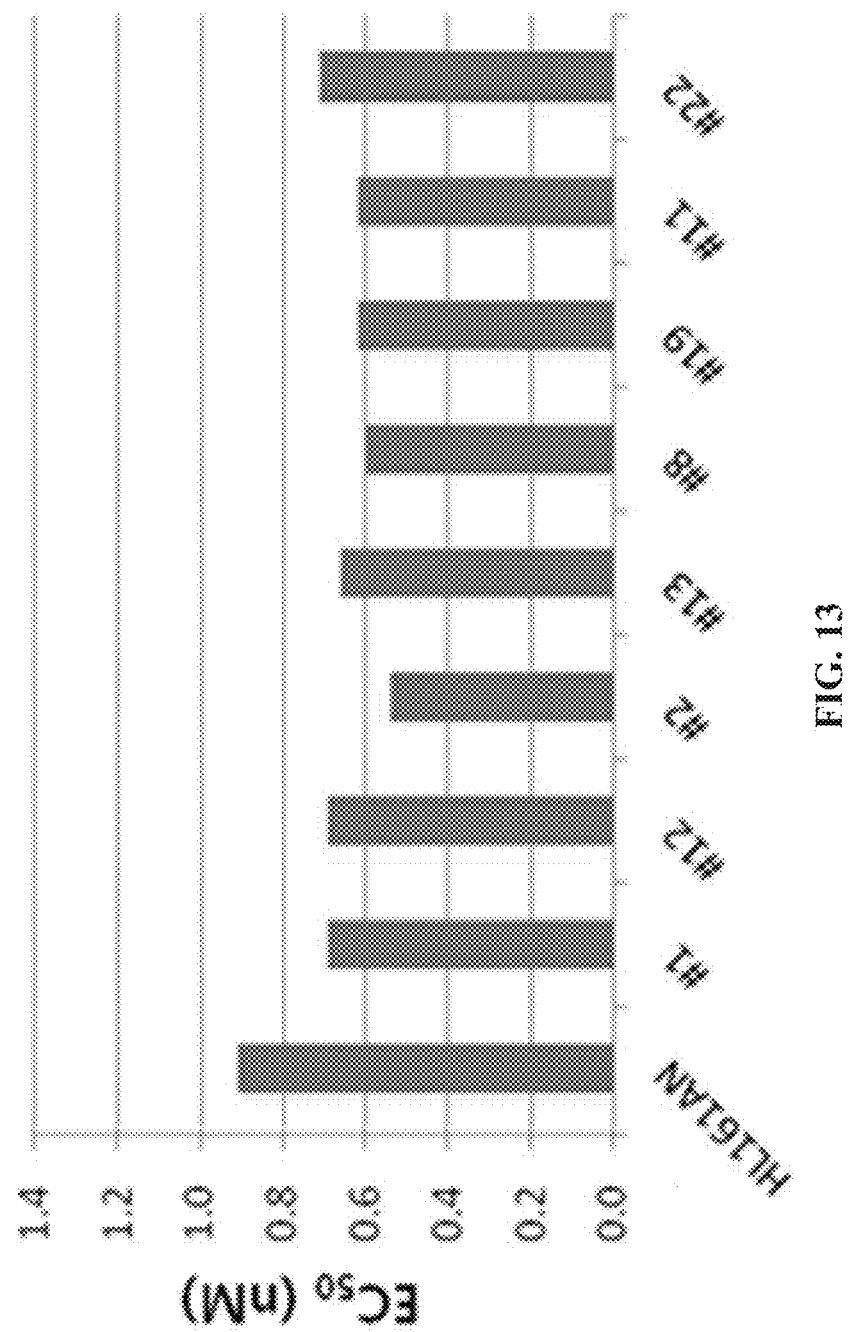
FIG. 13 is a drawing showing the results obtained by confirming the effect of the eight high concentration HL161AN variants selected after the first in vitro screening to block hFcRn using FACS.

It was performed in the same manner as in Example 4.5. The evaluation of hFcRn blocking was performed at 0.1 nM, 1 nM, 10 nM, and 100 nM using FACS. Each antibody blocked in a concentration-dependent manner, and the EC$_{50}$ value was similar to that of the control antibody HL161AN (FIG. 13).

Example 5.6. Evaluation of Stability

Figure 14:
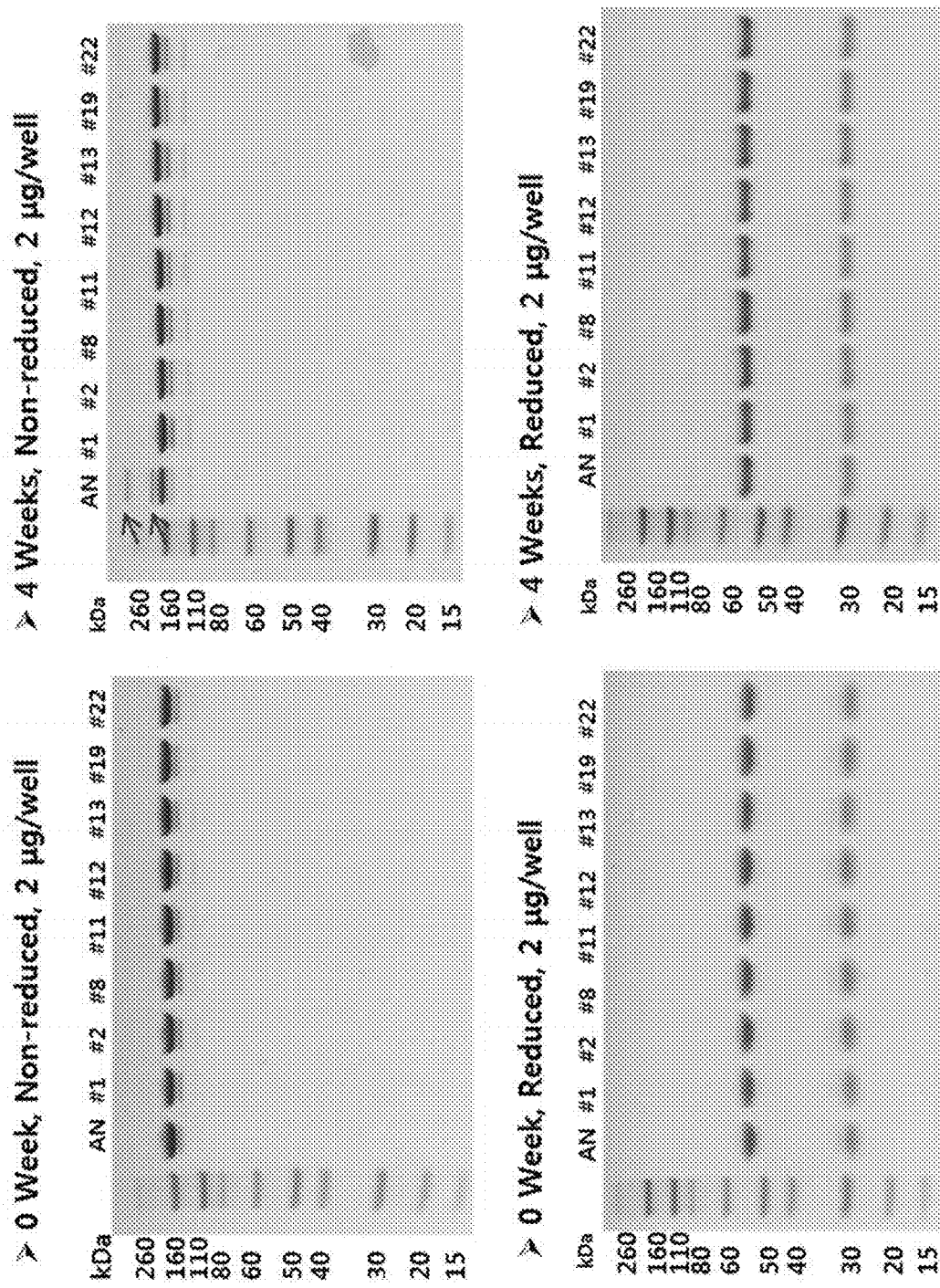
FIG. 14 is a drawing showing the SDS-PAGE results of the eight high concentration HL161AN variant samples.
Figure 15:
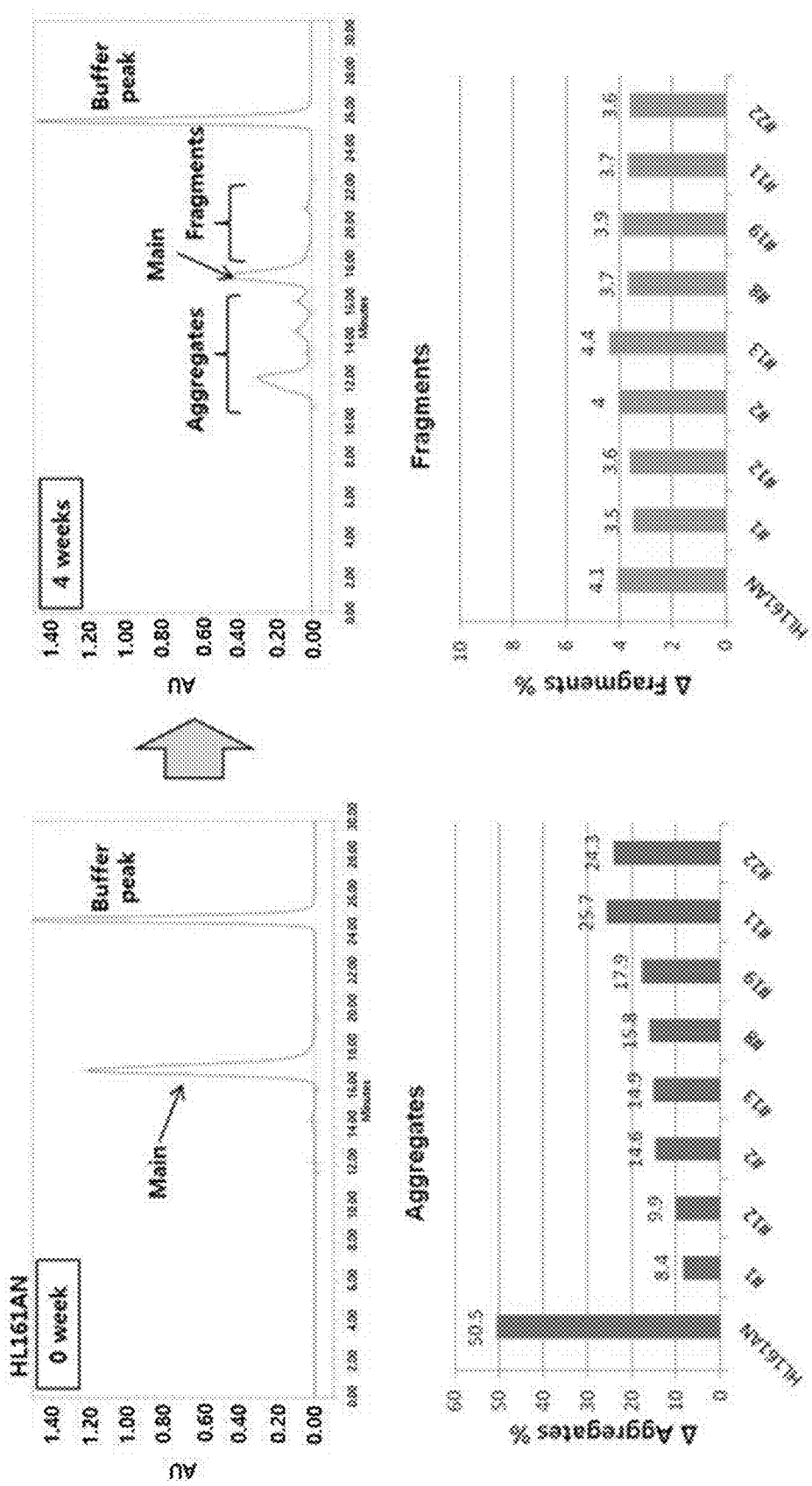
FIG. 15 is a drawing showing the SEC-HPLC results of the eight high concentration HL161AN variant samples.

It was performed in the same manner as in Example 4.6. In order to evaluate the stability of the eight high concentration HL161AN variants, the change in purity of the samples stored at 40° C. for 4 weeks was confirmed by SDS-PAGE and SEC-HPLC. In the case of HL161AN, the production rate of aggregates was 50% or more when stored for 4 weeks, which was also confirmed by SDS-PAGE (FIG. 14). In the case of the eight HL161AN variants, it was confirmed that the production rate of aggregates was 8.4% to 25.7%, which was improved compared to HL161AN, and the production rate of fragments was 3.5% to 4.4%, which was similar to that of HL161AN (4.1%) (FIG. 15).

Example 5.7. Analysis of Viscosity

The VROC chip was mounted on the main body of the viscometer (m-VROC system), and then about 300 μL of each of the high concentration HL161AN RS control sample and the HL161AN variant samples was loaded into a syringe. The VROC chip was connected to a syringe, and when it was stabilized at the set temperature of 25° C., the viscosity was measured by repeating three times.

The viscosity of HL161AN, a control substance, and the four high concentration HL161AN variants, which had sufficient sample volume, was analyzed. The viscosity of the buffer (50 mM histidine) was measured to be 0.93 cP. The average viscosity of the four HL161AN variants was measured to be 5.57 cP to 7.65 cP, which was less than a viscosity capable of subcutaneous (sc) administration (<20 cP) (Table 14). The viscosities of the four high concentration HL161AN variants are summarized and shown in Table 14 below.

TABLE 14

| Variant No. | Concentration (mg/mL) | Viscosity (cP) | Average viscosity (cP) |
|---|---|---|---|
| 8 | 161.7 | 5.712 | 5.84 |
|   |   | 5.884 |   |
|   |   | 5.921 |   |
| 12 | 157.9 | 5.539 | 5.57 |
|   |   | 5.610 |   |
|   |   | 5.554 |   |
| 13 | 158.1 | 7.626 | 7.65 |
|   |   | 7.655 |   |
|   |   | 7.672 |   |
| 19 | 163.2 | 7.294 | 7.27 |
|   |   | 7.233 |   |
|   |   | 7.274 |   |
| HL161AN | 152.6 | 5.370 | 5.42 |
|   |   | 5.474 |   |
|   |   | 5.421 |   |
| 50 mM histidine buffer (pH 5.0) | — | 0.923 | 0.93 |
|   |   | 0.940 |   |

The results of the second in vitro evaluation of the high concentration (150 to 170 mg/mL) samples of the eight HL161AN variants described above are summarized and shown in Table 15 below.

For the eight HL161AN variants selected in the first in vitro evaluation, 150 mg/mL to 163 mg/mL high concentration samples were prepared, and FcRn binding/blocking and stability were measured to select lead molecules. As a result, HL161AN variant No. 1 and variant No. 12, which had FcRn binding/blocking similar to that of HL161AN and improved stability, were selected as lead molecules (Table 15).

TABLE 15

| Variant No. | Light Chain | Heavy Chain | Protein Conc. (mg/mL) | Exp. | Viscosity (cP) | FACS binding (10 nM, MFI) pH 6.0 | pH 7.4 | FACS binding ($EC_{50}$, nM) pH 6.0 | Stability (40° C., 4 weeks) Δ Aggregates | Δ Fagments |
|---|---|---|---|---|---|---|---|---|---|---|
| HL161AN | N25 | C32 | 152.6 | — | 5.42 | 2952 | 7155 | 0.91 | 50.5 | 4.1 |
| #1 (HL161ANS) | N25S | C32S | 149.6 | +++ | — | 3272 | 6734 | 0.69 | 8.4 | 3.5 |
| #12 (HL161ANQ) | N25Q | C32S | 157.9 | +++ | 5.57 | 3394 | 7704 | 0.69 | 9.9 | 3.6 |
| #2 | N25S | C32Y | 153.5 | ++ | — | 3407 | 7004 | 0.54 | 14.6 | 4.0 |
| #13 | N25Q | C32Y | 158.1 | +++ | 7.65 | 3333 | 7941 | 0.66 | 14.9 | 4.4 |
| #8 | N25S | C32SQ82E | 161.7 | ++ | 5.84 | 3133 | 7055 | 0.60 | 15.8 | 3.7 |
| #19 | N25Q | C32SQ82E | 163.2 | ++ | 7.27 | 3243 | 7912 | 0.62 | 17.9 | 3.9 |
| #11 | N25S | C32YQ82E | 160.5 | ++ | — | 3447 | 6567 | 0.62 | 25.7 | 3.7 |
| #22 | N25Q | C32YQ82E | 161.3 | ++ | — | 3025 | 7079 | 0.71 | 24.3 | 3.6 |

[1])Transient expression, >200 mg/L: +++, <200 mg/L: ++

[2])SEC-HPLC analysis after storage at 40° C. for 4 weeks.

[3])—: Not tested.

Example 6. Conclusion of In Vitro Screening of HL161AN Antibody Variants

For in vitro evaluation of 22 HL161AN variants designed to improve the physical properties of HL161AN, a total of 22 HL161AN variants were produced and FcRn binding affinity/blocking and stability were measured. As a result, all 22 variants showed bioactivity similar to that of HL161AN, and the top eight variants with improved stability were first selected. The high concentration samples (150 mg/mL to 163 mg/mL) of the selected eight variants were prepared and the evaluation of stability was performed. As a result, all eight HL161AN variants showed bioactivity similar to that of HL161AN and had improved stability compared to HL161AN.

Figure 16:
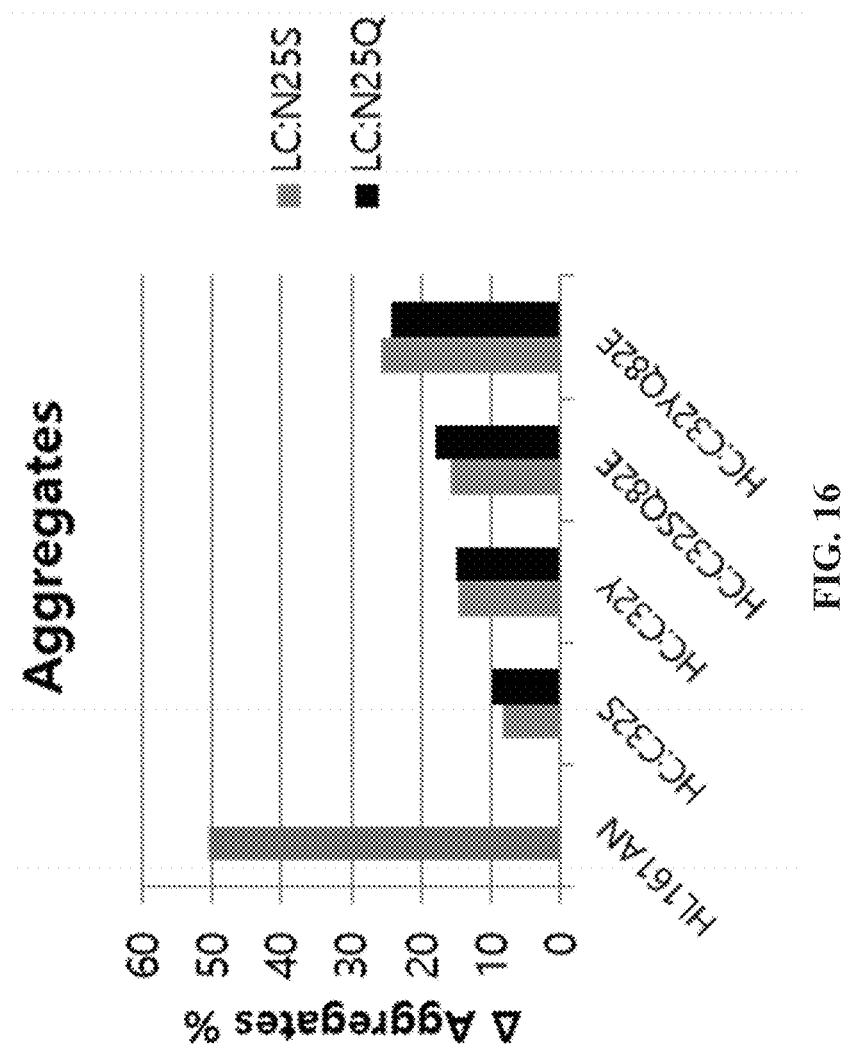
FIG. 16 is a graph showing the results obtained by comparing the aggregation production between HL161AN variant samples.

The light chain N25S mutation was added in the HL161AN variants No. 1, 2, 8, and 11, and the N25Q mutation was added in the variants No. 12, 13, 19, and 22. However, there was no difference in stability between the two groups. In the case of the heavy chain, C32 was further mutated to S or Y, and Q82 was further mutated to S, T, or E. However, in all variants, the production rate of aggregates was reduced by at least 2-fold compared to the control group HL161AN. In particular, when C32 was mutated to S, the production rate of aggregates (10% or less) was reduced by more than 5 times compared to HL161AN, and the stability was the most improved compared to other variants (FIG. 16). Accordingly, HL161AN variant No. 1 (LC:N25S, HC:C32S; HL161ANS) and variant No. 12 (LC:N25Q, HC:C32S; HL161ANQ), which had the production rate of aggregates of 10% or less, were finally selected as lead molecules.

III. Evaluation of hIgG Catabolism of HL161AN Antibody Variants Using hFcRn Transgenic Mice The in vivo hIgG catabolism efficacy of three HL161AN variants engineered to improve stability was evaluated using hFcRn transgenic (Tg) 32 mice.

The test material for the hIgG catabolism test of anti-FcRn antibody (HL161AN) variants using hFcRn transgenic mice was prepared as follows. The test substance information is shown in Table 16. The three HL161AN variants, HL161ANS-IgG1LALA, HL161ANQ-IgG1LALA and HL161ANQ-IgG4S228P, were diluted with the buffer shown in Table 16 below to prepare 2 mg/mL. 10 mL to be administered to 5 animals was prepared, divided into 4 doses of 2.5 mL/day, and stored at ≤−60° C. until administration.

TABLE 16

| HL161AN variant | Amino acid substitution | | | Buffer | |
| --- | --- | --- | --- | --- | --- |
| | Light chain | Heavy chain | Fc region | Concentration | Storage |
| HL161ANS-IgG1LALA | N25S | C32S | IgG1 (L234A/L235A) | 2 mg/mL, 50 mM histidine (pH 5.9) | ≤−60° C. |
| HL161ANQ-IgG1LALA | N25Q | C32S | IgG1 (L234A/L235A) | 2 mg/mL, 50 mM histidine (pH 5.9) | ≤−60° C. |
| HL161ANQ-IgG4S228P | N25Q | C32S | IgG4 (S228P) | 2 mg/mL, 50 mM histidine (pH 5.9) | ≤−60° C. |

In addition, HL161AN, a comparative substance, was prepared as shown in Table 17. HL161AN was diluted with a 50 mM histidine (pH 5.9) dilution buffer to prepare 2 mg/mL. 10 mL to be administered to 5 animals was prepared, divided into 4 doses of 2.5 mL/day, and stored at ≤−60° C. until administration.

TABLE 17

| | |
|---|---|
| Lot No. | HL161AN/16E11/ST01 |
| Storage condition | frozen storage (≤−60° C.) |
| Preparation concentration | 22.6 mg/mL |
| Formulation buffer | 50 mM histidine, 100 mM arginine-HCl, 10 mM methionine, 50 mM sucrose, 0.005% polysorbate 20, pH 5.0 |

As a control substance, IV-Globulin SN Inj. (IVIG), a product commercially available from GC Biopharma, was used. Product information is shown in Table 18. Specifically, 0.4 mL of 50 mg/mL of IV-Globulin Inj. was diluted to a concentration of 2 mg/mL by adding 9.6 mL of PBS (pH 7.4), and divided into 4 doses of 2.5 mL/day, and stored at 4° C. for up to 4 days until administration.

TABLE 18

| | |
|---|---|
| Dose | 2,500 mg/50 mL (50 mg/mL) |
| Storage condition | Refrigerated storage (4° C.) |
| Manufacturer | GC Biopharma |

In addition, the tracer was prepared by mixing 495 mg/kg of total hIgG and 5 mg/kg of biotin-hIgG. Specifically, total hIgG was prepared at a concentration of 49.5 mg/mL in order to administer 495 mg/kg of IV-Globulin Inj. by adding 0.2 mL of PBS (pH 7.4) to 19.8 mL of 50 mg/mL of IV-Globulin Inj. In addition, biotin-hIgG was prepared by adding 267 μL of 10 mM biotin to 20 mg of IV-Globulin Inj., followed by incubation at room temperature for 30 minutes. Thereafter, in order to remove free biotin, the sample was transferred to a dialysis bag, and dialysis was performed with 1×PBS (pH 7.4). The biotin-labeled hIgG was quantified by measuring absorbance at $UV_{280\ nm}$ (IgG E1%=14.0 at 280 nm).

Example 7. Animal Experimental Method

The stocked mFcRn$^{-/-}$hFcRn transgenic (Tg) 32 mice (Jackson Laboratory, USA) (male, 5-10 weeks old) were identified by marking the number on the tail and putting 5 mice in each cage. After enrollment, they were acclimatized for 1 to 2 weeks. In addition, the sample substances were administered by dividing the groups as shown in Table 19 below.

TABLE 19

| Group | Concentration (mg/kg) | Route of administration | Number of animals* |
|---|---|---|---|
| Vehicle[1] | — | i.p.[2] | 4 |
| HL161ANS (IgG1- LALA) | 20 | i.p. | 4 |
| HL161ANQ (IgG1- LALA) | 20 | i.p. | 4 |
| HL161ANQ (IgG4 S228P) | 20 | i.p. | 4 |
| HL161AN | 20 | i.p. | 4 |
| IVIG | 20 | i.p. | 4 |

*Five animals per group were administered, including one animal in each group as a spare.
[1]Vehicle: 50 mM histidine, pH 5.9
[2]i.p.: intraperitoneal injection Specifically, as a tracer, 495 mg/kg of total hIgG and 5 mg/kg of biotin-hIgG were intraperitoneally administered (i.p.) at a dose of 10 mL/kg, and the administration time was set to 0 hours. In addition, the test substances HL161ANS (IgG1-LALA), HL161ANQ (IgG1-LALA), and HL161ANQ (IgG4 S228P), the comparative substance HL161AN, and the control substance vehicle and IVIG were intraperitoneally administered 4 times at a dose of 20 mg/kg on 24, 48, 72, and 96 hours after tracer administration.

Thereafter, the administration time of the tracer was set to 0 hours, and then blood was collected after 24, 48, 72, 96, 120, and 168 hours. The test substance, comparative substance, and control substance were administered at 24, 48, 72, and 96 hours. In this case, blood was first collected, and then administration was performed. The mice were anesthetized using an respiratory anesthesia device, and then blood was collected from the orbital venous plexus using a microhematocrit capillary tube.

About 0.2 mL of whole blood was centrifuged at 3000 rpm for 15 minutes. Thereafter, the obtained serum was transferred to a 1.5 mL microcentrifuge tube and stored at ≤−60° C. until analysis.

Example 8. Confirmation of Degree of Catabolism of Biotin-hIgG Tracer Through ELISA Analysis The degree of catabolism of the biotin-hIgG tracer in the body was confirmed using the serum obtained by the above method.

Specifically, dilution solution/blocking buffer (assay diluent (AD), 1% BSA in 1×PBS, pH 7.4): 10 g of Probumin® was dissolved in 900 mL of 1×PBS (pH 7.4), adjusted to a final volume of 1 L, filtered through a 0.2 μm filter, and then stored at 4° C. In addition, the standard stock (500 ng/mL biotin-hIgG) was prepared by mixing 10 μL of biotin-hIgG (4 mg/mL) with 990 μL of PBS to obtain 40 μg/mL. Thereafter, 750 μL of the dilution solution was mixed with 250 μL of 40 μg/mL of biotin-hIgG to prepare 10 μg/mL. 500 ng/mL of the standard stock was prepared by mixing 50 μL of 10 μg/mL of biotin-hIgG with 950 μL of the dilution solution, and then aliquoted by 50 μL. The aliquoted standard stock was stored at −80° C. In addition, the neutral avidin was used by diluting 10 μL of 2 mg/mL of neutral avidin with 10 mL of 1×PBS to 2 μg/mL.

Thereafter, the samples of the vehicle and IVIG groups were all diluted 1:10,000 using a dilution solution to prepare analysis samples. Except for the HL161ANS (IgG1-LALA) group, samples of 24, 48, and 72 hr were diluted 1;10,000, and samples of 96, 120, and 168 hr were diluted 1:1,000. In the case of the HL161ANS (IgG1-LALA) group, only the sample of 168 hr was diluted 1:1,000, and all samples at the other time points were diluted 1:10,000. The diluted samples were loaded in duplicate at 100 μL per well and incubated at room temperature for 2 hours.

Figure 17:
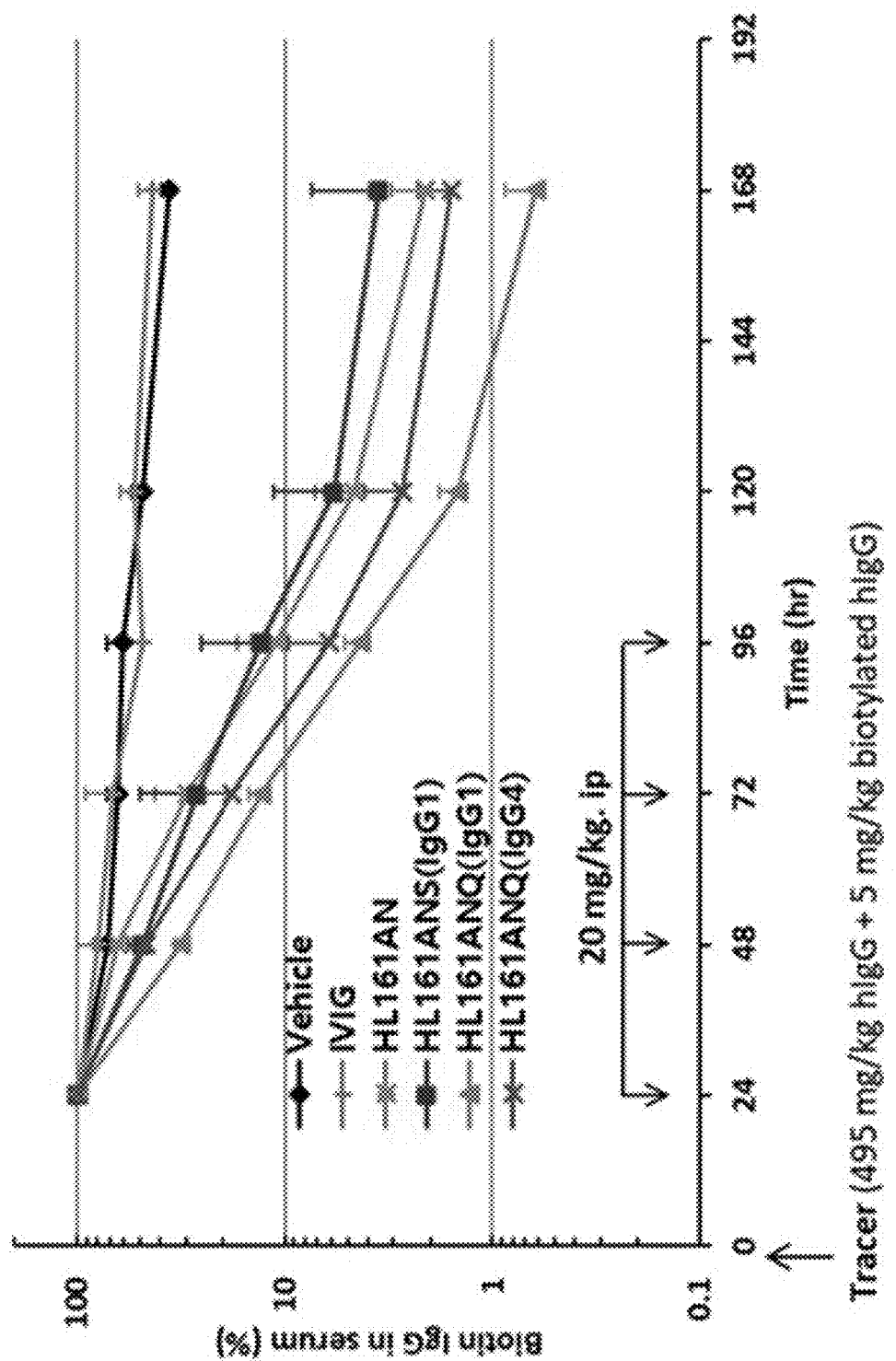
FIG. 17 is a drawing showing the results of biotin-hIgG catabolism of the HL161AN variants (20 mg/kg) in Tg mice. It shows the results obtained by collecting blood at 24, 48, 72, 96, 120, and 168 hours after tracer administration and measuring the concentration of biotin-hIgG by ELISA.

The concentration of biotin-hIgG in the blood administered at 0 hours was measured at 24, 48, 72, 96, 120, and 168 hours after administration of HL161ANS (IgG1-LALA), HL161ANQ (IgG1-LALA), HL161ANQ (IgG4S228P), HL161AN, and IVIG at 20 mg/kg by ELISA. As a result, the other test groups showed a significant decrease in biotin-hIgG over time compared to the vehicle and IVIG administration group. On the other hand, there was no significant difference between the three HL161AN variants and HL161AN. Among the three variants, HL161ANQ (LC: N25Q, HC:C32S)-IgG1-LALA showed a relatively high effect on biotin-hIgG catabolism. However, there was no statistical significance and thus it was determined to be a similar effect (Table 20, Table 21, and FIG. 17).

The concentrations of biotin-hIgG after administration of the HL161AN variants at 20 mg/kg are summarized and shown in Table 20 below.

TABLE 20

|  | 24 hr | 48 hr | 72 hr | 96 hr | 120 hr | 168 hr |
|---|---|---|---|---|---|---|
| Vehicle | 52.1 ± 2.5 | 37.3 ± 1.9 | 33.4 ± 3.8 | 31.2 ± 5.3 | 25.2 ± 2.3 | 19.0 ± 0.6 |
| HL161ANS (IgG1-LALA) | 46.5 ± 8.2 | 21.2 ± 9.8 | 11.0 ± 8.2 | 5.3 ± 4.4 | 2.3 ± 2.0 | 1.4 ± 1.4 |
| HL161ANQ (IgG1-LALA) | 60.3 ± 16.1 | 19.1 ± 4.2 | 7.7 ± 2.1 | 2.5 ± 0.5 | 0.9 ± 0.1 | 0.4 ± 0.1 |
| HL161ANQ (IgG4S228P) | 47.3 ± 15.3 | 21.2 ± 4.2 | 7.7 ± 2.2 | 2.6 ± 0.8 | 1.2 ± 0.3 | 0.7 ± 0.1 |
| HL161AN | 37.7 ± 8.0 | 23.3 ± 6.5 | 10.7 ± 4.4 | 3.9 ± 1.9 | 1.7 ± 0.8 | 0.8 ± 0.3 |
| IVIG | 51.2 ± 15.5 | 38.2 ± 4.6 | 32.0 ± 3.4 | 23.9 ± 4.3 | 26.5 ± 5.0 | 21.7 ± 4.7 |

The biotin-hIgG catabolism results (% of 24 hours after tracer administration) of the HL161AN variants in Tg32 mice are summarized and shown in Table 21 below.

TABLE 21

|  | 24 hr | 48 hr | 72 hr | 96 hr | 120 hr | 168 hr |
|---|---|---|---|---|---|---|
| Vehicle | 100.0 ± 0.0 | 71.8 ± 3.6 | 64.2 ± 7.7 | 60.2 ± 11.4 | 48.8 ± 6.2 | 36.6 ± 2.5 |
| HL161ANS (IgG1-LALA) | 100.0 ± 0.0 | 48.8 ± 29.8 | 26.4 ± 23.8 | 13.0 ± 12.2 | 5.7 ± 5.6 | 3.5 ± 3.9 |
| HL161ANQ (IgG1-LALA) | 100.0 ± 0.0 | 32.0 ± 1.7 | 12.9 ± 2.0 | 4.3 ± 0.8 | 1.5 ± 0.3 | 0.6 ± 0.2 |
| HL161ANQ (IgG4S228P) | 100.0 ± 0.0 | 46.8 ± 10.2 | 17.9 ± 9.5 | 6.2 ± 3.5 | 2.7 ± 1.4 | 1.6 ± 0.7 |
| HL161AN | 100.0 ± 0.0 | 63.8 ± 19.2 | 29.6 ± 12.8 | 10.9 ± 5.9 | 4.6 ± 2.5 | 2.1 ± 1.0 |
| IVIG | 100.0 ± 0.0 | 79.4 ± 20.6 | 68.0 ± 23.3 | 48.8 ± 10.2 | 53.6 ± 8.2 | 43.9 ± 7.4 |

Example 9. Calculation of Half-Life of Biotin-IgG Tracer Through Pharmacokinetic (PK) Analysis The biotin-hIgG ELISA quantitative analysis results were used to calculate the half-life of tracer after administration of each test substance with BAcalc (2007, Korea). Specifically, using the ELISA analysis results, the half-lives from 24 hours to 120 hours after tracer administration were calculated for the three HL161AN variants (Table 16), the comparative substance, and the control substance.

As a result, as shown in Table 22, the half-lives were 22.7±9.0 hours for HL161ANS (IgG1-LALA), 15.9±0.9 hours for HL161ANQ (IgG1-LALA), and 17.8±2.6 hours for HL161ANQ (IgG4S228P). The half-life of the comparative substance HL161AN was 20.6±3.6 hours, which was confirmed to be equivalent to those of the three HL161AN variants. In addition, the half-lives of vehicle and IVIG were 108.2±29.0 hours and 98.0±16.8 hours, respectively, which were confirmed to be similar. The results of the half-life analysis of biotin-hIgG after administration of the HL161AN variants in Tg mice are summarized and shown in Table 22 below.

TABLE 22

| Group name | $T_{1/2}$ (hr) |
|---|---|
| Vehicle | 108.3 ± 29.0 |
| HL161ANS (IgG1-LALA) | 22.7 ± 9.0 |
| HL161ANQ (IgG1-LALA) | 15.9 ± 0.9 |
| HL161ANQ (IgG4D228P) | 17.8 ± 2.6 |
| HL161AN | 20.6 ± 3.6 |
| IVIG | 98.0 ± 16.8 |

Example 10. hIgG Catabolism of HL161AN Antibody Variants in hFcRn Transgenic Mice The effect of hIgG catabolism was confirmed after administration to Tg32 mice at 20 mg/kg for the three HL161AN variants engineered to increase the stability of HL161AN. As a result, it was confirmed that HL161ANS (IgG1-LALA), HL161ANQ (IgG1-LALA), and HL161ANQ (IgG4S228P) had the effect of hIgG catabolism equivalent to that of the comparative substance HL161AN.

In conclusion, it was confirmed that HL161ANS (light chain: N32S, heavy chain: C32S) and HL161ANQ (light chain: N32Q, heavy chain: C32S), which are substances in which two amino acids are substituted in order to increase stability among the variable domains of HL161AN, had the in vivo IgG catabolism effect similar to that of the original molecule HL161AN. That is, it was confirmed that the three HL161AN variants engineered to increase stability did not affect the in vivo efficacy compared to the existing HL161AN.

Example 11. Conclusion of hIgG Catabolism by Administration of Anti-FcRn Antibody (HL161AN) Variants in hFcRn Transgenic Mice In order to evaluate the effect of HL161AN and HL161AN variants (HL161ANS and HL161ANQ) on the in vivo catabolism of biotin-hIgG, blood was collected by time after administration to Tg32 mice at 20 mg/kg, and the concentration of biotin-hIgG in the blood was confirmed.

As a result, in the case of biotin-hIgG, a similar biotin-hIgG catabolism effect was confirmed for all three administered substances. All test substances (HL161AN, HL161ANS, and HL161ANQ) reduced the concentration of biotin-hIgG by 90% or more within 120 hours after administration compared to the IVIG control group.

In conclusion, it was confirmed that the hIgG catabolism effect of HL161ANS and HL161ANQ was not significantly different from that of HL161AN through the hIgG catabolism test.

Example 12: Comparison of Antibodies
HL161ANS and Batoclimab

In this head-to-head study in monkeys, the HL161ANS variant (also referred to as IMVT-1402) was compared to another anti-FcRn antibody, Batoclimab (HL161BKN, see, e.g., International Patent Application Publication No. WO/2015/167293).

20 monkeys in four groups were dosed intravenously with 50 mg/kg batoclimab, 5 mg/kg HL161ANS, 50 mg/kg HL161ANS, or placebo. IgG, albumin and low-density lipoprotein (LDL) and cholesterol) were measured at the indicated time points. Cynomolgus monkeys are known to be reliable pharmacodynamic proxy for anti-FcRn mediated impacts on IgG (see, e.g., Lledo-Garcia, et al., UCB Pharma, 2022).

Figure 18:
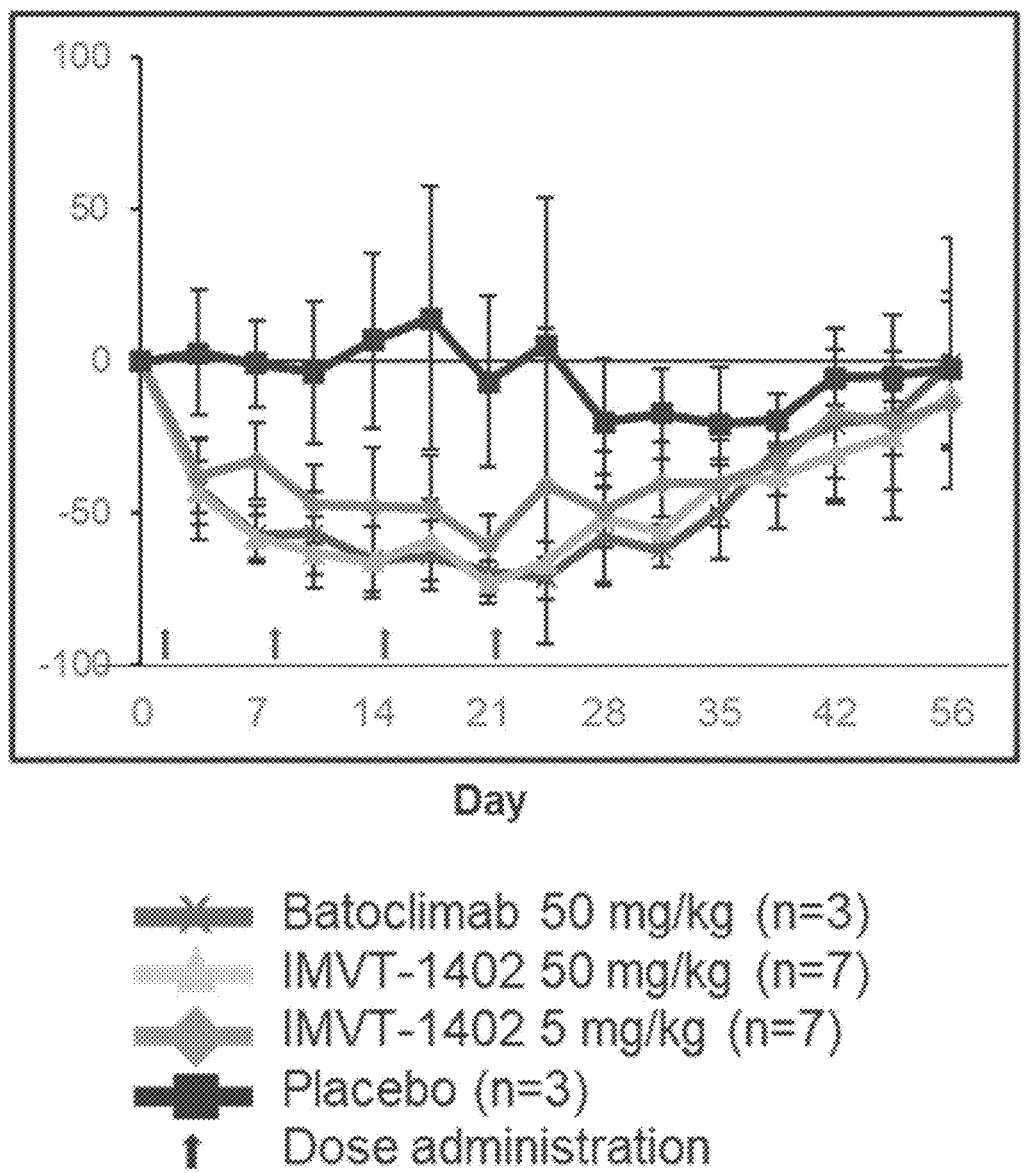
FIG. 18 is a drawing showing IgG reduction in monkeys after treatment with HL161ANS (IMVT-1402).
Figure 19A:
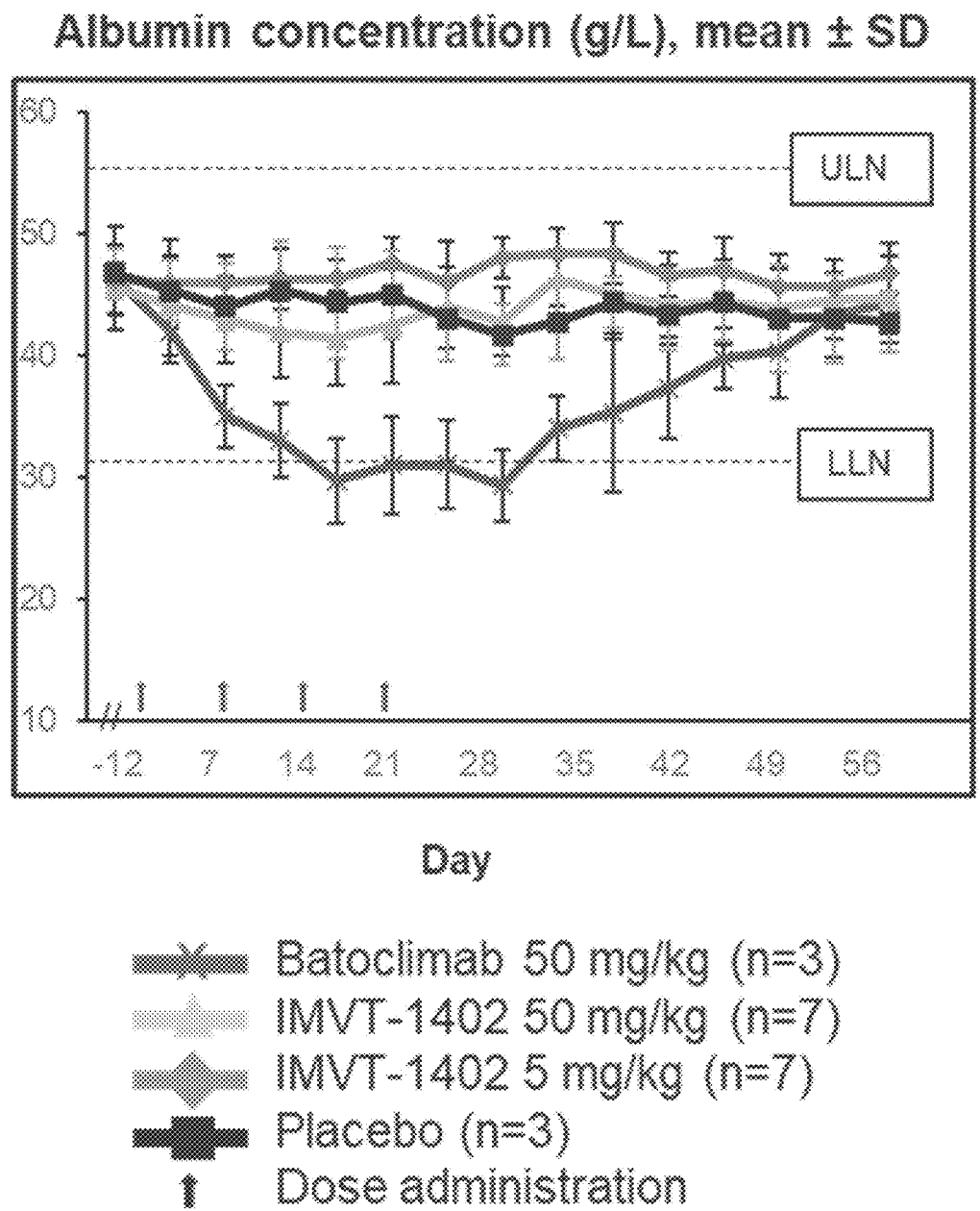
FIGS. 19A-19C are drawings showing albumin, LDL, and cholesterol levels, respectively, in monkeys after treatment with HL161ANS (IMVT-1402).
Figure 19B:
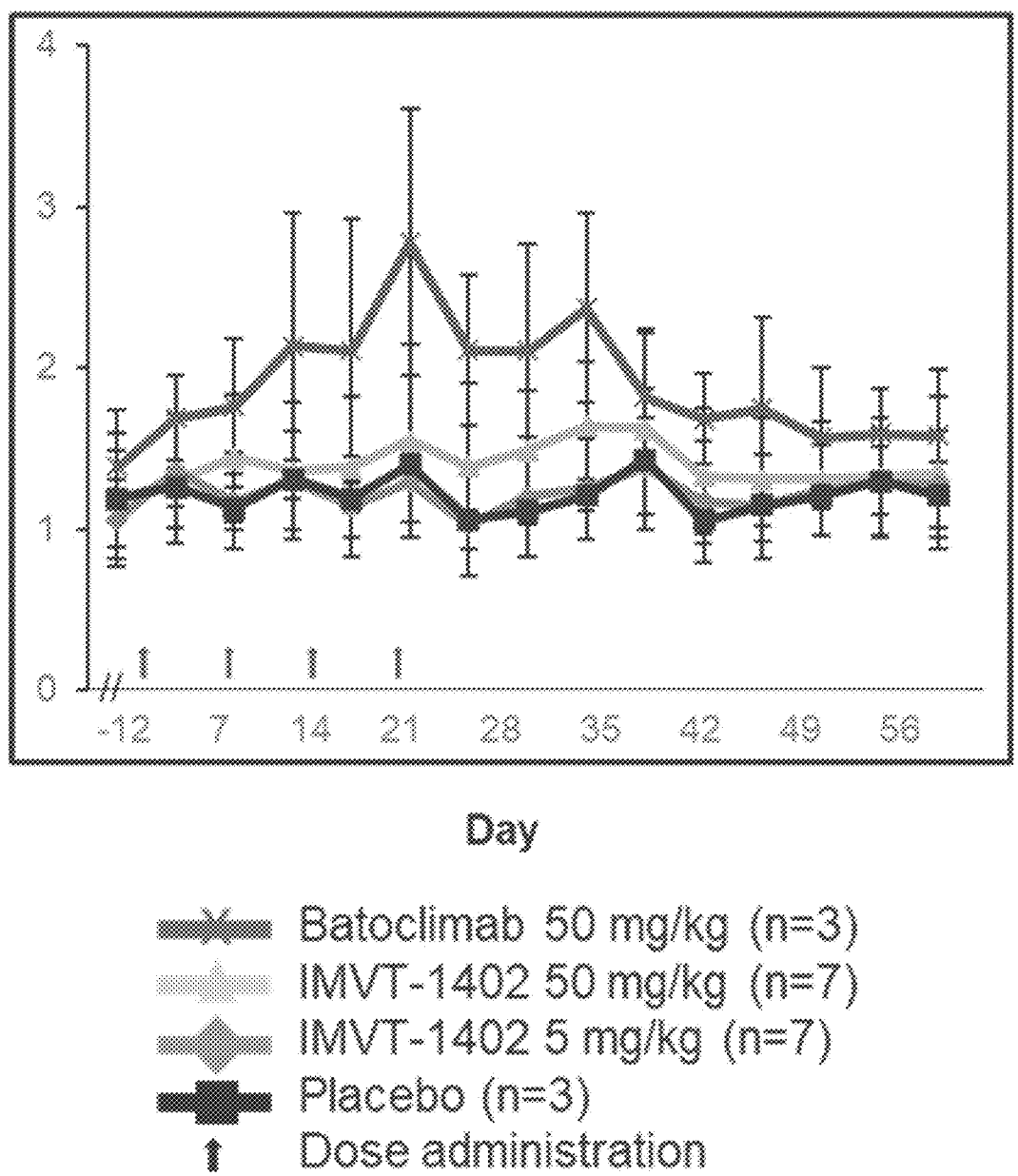
Figure 19C:
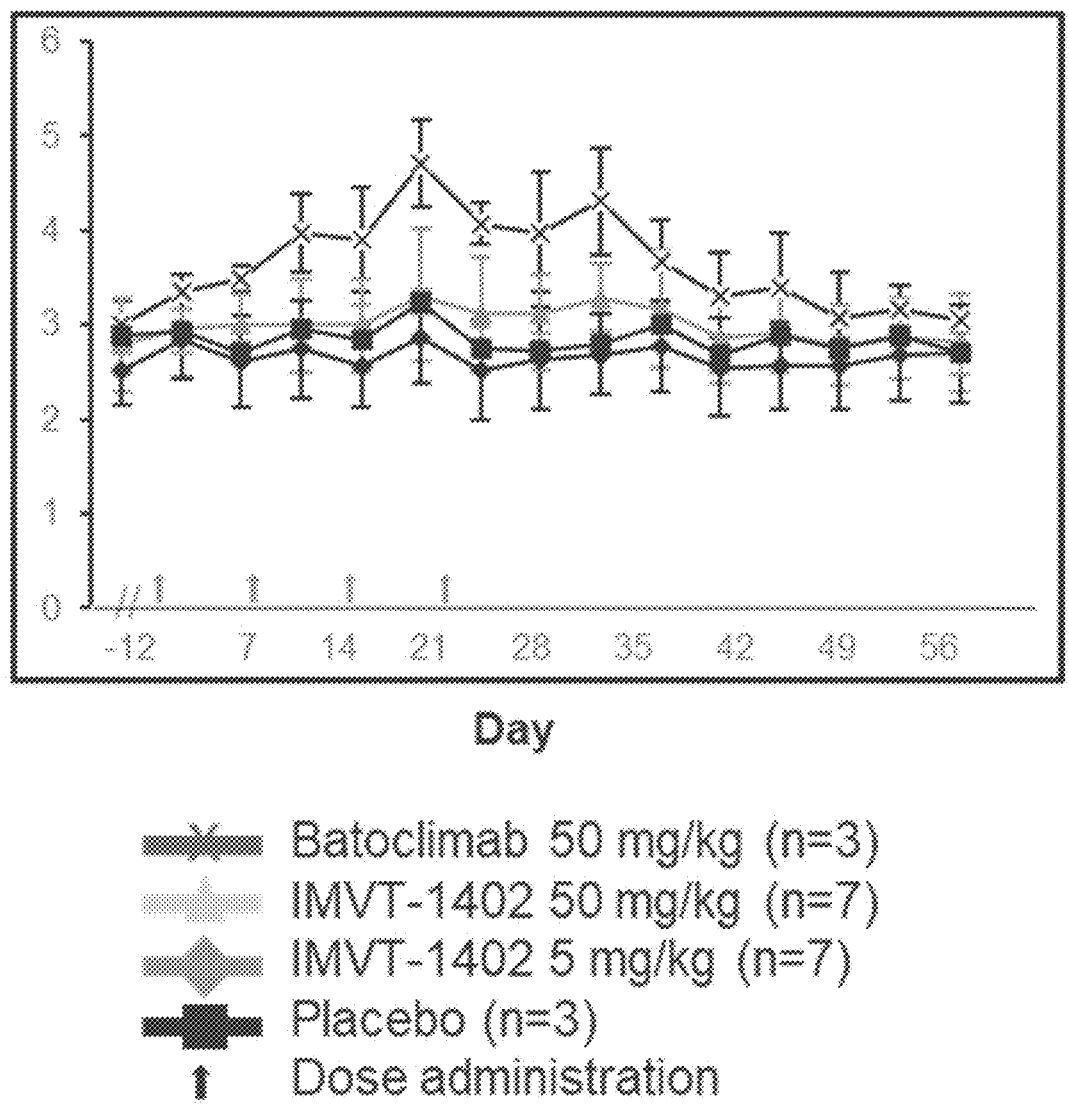
Figure 20:
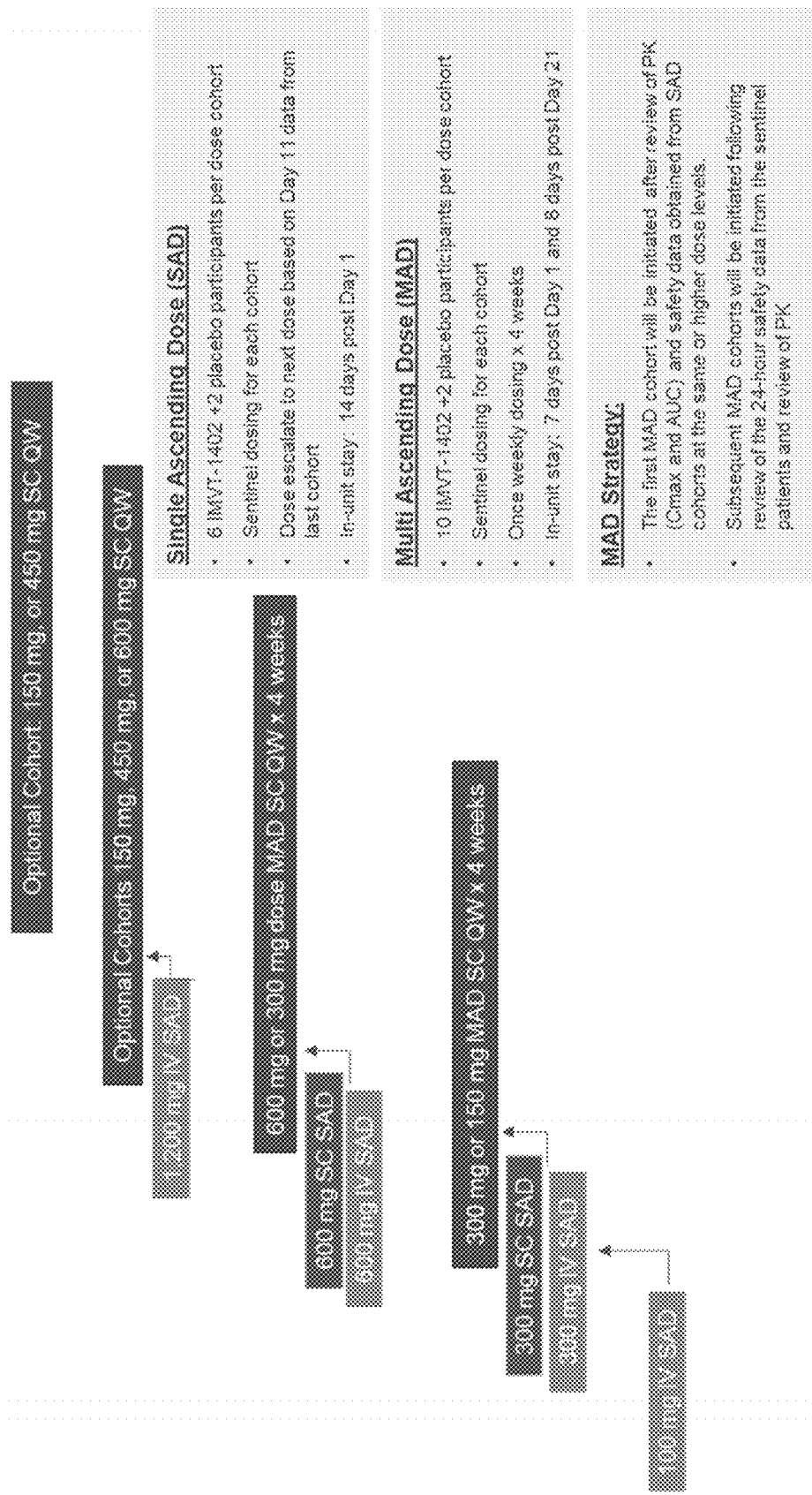
FIG. 20 is a schematic showing the design of the clinical study described in Example 13. Abbreviations: AUC=area under the concentration-time curve; $C_{max}$=maximum observed concentration; IV=intravenous; MAD=multiple ascending dose; PK=pharmacokinetics; QW=once weekly; SAD=single ascending dose; SC=subcutaneous.

At comparable doses, IgG lowering was nearly identical for batoclimab and HL161ANS (FIG. 18). The IgG lowering effect was dose-dependent. HL161ANS and placebo demonstrated similar impacts on albumin, LDL, and cholesterol (FIGS. 19A-19C, respectively). Thus, there was no substantial effect of HL161ANS on albumin, LDL or cholesterol levels.

Example 13: A 4-Week Intravenous Exploratory
Pharmacology Study Followed by a 4-Week
Recovery Period in Cynomolgus Monkeys The objective of the study was to determine the pharmacology, toxicity and toxicokinetic (TK) profile of the test item, HL161ANS, following the once weekly intravenous injection administration to the cynomolgus monkey for 4 weeks (on Days 1, 8, 15 and 22) and to assess the persistence, delayed onset or reversibility of any changes following a 4-Week recovery period.

The test, positive control and control/vehicle items were administered to groups of monkeys once weekly by intravenous injection administration (over approximately 60 seconds) on Days 1, 8, 15 and 22 as described in Table 23 below:

TABLE 23

| Group Numbers | Group Designation | Dose Level (mg/kg/day) | Dose Concentration (mg/mL) | Dose Volume (mL/kg) | Number of Animals Males | Females |
|---|---|---|---|---|---|---|
| 1 | Control/Vehicle [a] | 0 | 0 | 2 | 1 | 2 |
| 2 | Positive Control [b] | 50 | 25 | 2 | 2 | 1 |
| 3 | Low dose | 5 | 2.5 | 2 | 3 | 4 |
| 4 | High dose | 50 | 25 | 2 | 3 | 4 |

[a] Control/Vehicle animals were administered the control/vehicle item (20 mM Histidine, 200 mM Arginine, pH 6.0, 2% w/v PS-20).
[b] Group 2 animals were administered the positive control item only.

Following completion of the last weekly dosing cycle, all animals were observed for 4 weeks and then animals of Groups 1, 3 and 4 were euthanized and subjected to a necropsy examination on Day 57.

Parameters monitored during this study included mortality, clinical observations and body weights. In addition, clinical pathology parameters (hematology, coagulation, clinical chemistry and urinalysis) were evaluated. Blood sampling was performed for toxicokinetic, ApoB, IgG and ADA evaluation. A necropsy was performed and tissues were collected for possible histopathological examination.

No mortality or HL161ANS related clinical signs were noted.

No test item related effects were noted on body weights, hematology, coagulation, clinical chemistry and urinalysis.

Splenic mottling at 5 and 50 mg/kg of HL161ANS and a higher incidence of small thymus at 50 mg/kg was noted. As no microscopic examination was performed the toxicological significance of these findings could not be determined.

In conclusion, the once weekly intravenous administration for four weeks (Days 1, 8, 15 and 22) of HL161ANS to the cynomolgus monkey at 5 and 50 mg/kg was well tolerated.

Example 14: A 6-Week Subcutaneous and/or Intravenous Injection Toxicity and Toxicokinetic Study with HL161ANS in Cynomolgus Monkeys with a 9-Week Recovery Phase The purpose of this study was to evaluate the toxicity and determine the toxicokinetics of HL161ANS when administered twice weekly via subcutaneous and/or intravenous (slow bolus) injection to cynomolgus monkeys for at least 6 weeks (total of 13 dose intervals) and to assess the reversibility or persistence of any effects after a 9-week recovery phase.

Male and female cynomolgus monkeys were assigned to six groups, and doses were administered as indicated in Table 24. Animals were dosed via subcutaneous (SC) injection (Groups 1 through 4) and/or intravenous (IV)-(slow bolus) injection (Groups 1, 5, and 6) on Days 1, 4, 8, 11, 15, 18, 22, 25, 29, 32, 36, 39, and 43 of the dosing phase at a volume of 1.3 mL/kg/dose. The vehicle control article/diluent was HL161ANS Formulation Buffer. Additionally, KLH was administered to each animal once on Day 14 of the dosing phase and once on Day 28 of the recovery phase via subcutaneous injection at a volume of 1 mL/dose.

TABLE 24

| Group[a] | Dose Level[b] (mg/kg/dose) | Dose Concentration[b] (mg/mL) | Number of Animals[c] | |
|---|---|---|---|---|
| | | | Males | Females |
| 1 (Control - SC and IV) | 0 | 0 | 5 | 5 |
| 2 (Low - SC) | 50 | 38.5 | 3 | 3 |
| 3 (Mid - SC) | 100 | 76.9 | 3 | 3 |
| 4 (High - SC) | 198.4 | 152.6 | 5 | 5 |
| 5 (Low - IV) | 50 | 38.5 | 3 | 3 |
| 6 (High - IV) | 198.4 | 152.6 | 5 | 5 |

[a]Group 1 was administered vehicle control article only.
[b]Animals were dosed at a volume of 1.3 mL/kg/dose.
[c]Three animals/sex/group were designated as terminal animals, and 2 animals/sex/group in Groups 1, 4, and 6 were designated as recovery animals.

Assessment of toxicity was based on mortality, clinical observations, body weights, qualitative food consumption, ophthalmic observations, electrocardiographic (ECG) measurements, dermal observations, neurobehavioral observations, respiration rate assessment, and clinical and anatomic pathology. Blood samples were collected for toxicokinetic, ADA, and immunotoxicology evaluations.

Toxicokinetic parameters were generally similar in male and female monkeys (within 2-fold). With SC dosing, HL161ANS systemic exposures, as indicated by $C_{max}$ and $AUC_{0-72}$ values, increased with dose level. $AUC_{0-72}$ assessments are limited insofar as this parameter could not be determined on Day 43 in any but the recovery animals in the 198.4 mg/kg/dose group, as terminal sacrifice occurred on Day 44. The increases were generally greater than proportional between doses of 50.0 and 198.4 mg/kg/dose. After repeated twice-weekly SC dosing, there was no observed serum accumulation in the 50.0 mg/kg/dose group from Day 1 to Day 22 based on combined-sex mean ARs, reflecting values in two individual female animals in the group that were considerably less than 1.0. Accumulation did occur at higher doses, with the extent of accumulation increasing with dose. Accumulation ratios for $C_{max}$ and $AUC_{0-72}$ values were 1.65 to 1.86 in the 100.0 mg/kg/dose group (Day 1 to Day 22) and 1.83 to 2.88 in the 198.4 mg/kg/dose group (Day 1 to Day 22 and Day 43). With IV dosing, HL161ANS $C_{max}$ and $AUC_{0-72}$ values increased with dose level. The increases in $AUC_{0-72}$ values were greater than proportional between doses of 50.0 and 198.4 mg/kg/dose. Dose proportionality assessments for $C_{max}$ after IV bolus administration indicated an approximately proportional increase with dose on Day 1 but were difficult to interpret on Days 22 and 43 due to the contributing effects of accumulation. After repeated twice-weekly IV dosing, serum accumulation, based on $C_{max}$, was slight (50.0 mg/kg/dose) to modest (198.4 mg/kg/dose), with ARs of 1.11 to 1.23 and 1.40 to 1.63, respectively. For $AUC_{0-72}$, combined-sex mean exposures in the 50.0 mg/kg/dose group decreased by one-half from Day 1 to Day 22 and remained the same through Day 43, with ARs of approximately 0.460; this reflects very low ARs in five of the six animals in this group. Modest increases in $AUC_{0-72}$ were observed in the 198.4 mg/kg/dose IV group, with ARs of approximately 1.5. Positive anti-drug antibody (ADA) titers were observed in 35 of 38 (92.1%) HL161ANS-treated animals (1 animal at 100 mg/kg/dose SC and 2 animals at 198.4 mg/kg/dose IV were negative for ADA titers). HL161ANS induced ADA may have impacted accumulation ratios on Days 22 and 43 as ARs tended to decline with increased ADA titers; the 50 mg/kg/dose group was more impacted than other groups.

On Day 30 of the dosing phase, one female administered 100 mg/kg/dose SC was sacrificed due to a thin body condition (body weight loss of 0.3 kg), a low body condition score, sunken eyes, decreased skin turgor, liquid feces, and a low body temperature (36.4° C.). The animal was previously examined and treated for swelling and a laceration on the left foot on Day 23 of the dosing phase; however, the condition of this animal worsened. HL161ANS-related clinical pathology changes consisted of mildly to moderately decreased total protein and albumin concentrations. These changes were similar to those observed in animals that survived to the scheduled sacrifice and were likely exacerbated by the inflammatory response and clinical observations of liquid feces.

Macroscopic observations included abnormal shape and compression of the cerebrum, which correlated microscopically with minimal dilatation of the brain stem, which was considered incidental. Minimally increased cellularity of myeloid precursors in the sternal bone marrow might have correlated with the inflammatory response related to the laceration on the digit. The cause of the moribund condition was undetermined based on microscopic observations, but the continuous liquid feces and digit wound that led to the decreased mobility and food consumption would have contributed to the moribund condition of this animal. Based on the available clinical observations and clinical and anatomic pathology results, this mortality was not associated with HL161ANS. No HL161ANS-related clinical observations; ophthalmic observations; body weight or food consumption alterations; respiration rate effects; dermal observations; ECG effects; effects on coagulation, urinalysis, or IgM and IgA titers; effects on CH50 levels; effects on immunity and lymphocyte subsets; organ weight differences; or macroscopic findings were noted.

An increase in IgM titers was noted predose of Day 22 of the dosing phase, compared with predose of Day 1 of the dosing phase, in most controls and males and females administered ≥50 mg/kg/dose HL161ANS. A subsequent decline in IgM titers was noted at predose and 1344 hours postdose of Day 43 of the dosing phase in females administered ≥50 mg/kg/dose HL161ANS with values remaining comparable to controls. In HL161ANS-treated males, IgM titers predose on Day 43 of the dosing phase remained comparable to predose of Day 22 of the dosing phase, with a subsequent decline noted at 1344 hours postdose of Day 43 of the dosing phase. A decrease in IgG concentrations was noted predose of Day 4 of the dosing phase, compared with predose of Day 1 of the dosing phase, in all animals administered ≥50 mg/kg/dose HL161ANS. Percent change of mean IgG concentrations for groups administered ≥50 mg/kg/dose were approximately 48 to 76% below baseline values at Day 43 of the dosing phase, consistent with expected pharmacology. Mean IgG concentrations for each group increased starting on Day 15 of the recovery phase and returned to baseline levels by the end of the recovery phase. Increased IgG concentrations, compared with predose Day 1 of the dosing phase, were noted in two females administered 198.4 mg/kg/dose SC starting on Days 15 of the dosing phase following the decrease seen on Day 4 of the dosing phase. IgG concentrations remained high through Day 43 of the dosing phase for both animals followed by a decrease on Day 1 of the recovery phase. Increased IgG concentrations, compared with predose Day 1 of the dosing phase, was noted in one male administered 198.4 mg/kg/dose SC starting on Day 15 of the dosing phase following the decrease seen on Day 4 of the dosing phase. IgG concentrations remained high through Day 32 of the dosing phase followed by a decrease on Day 36 of the dosing phase. IgG concentrations decreased below baseline until Day 50 of the recovery phase. The increase in IgG concentration in one animal may be related to the vascular inflammation seen in various tissues at the microscopic examination. These variations from the group mean IgG concentrations are of unknown relationship with HL161ANS and/or ADA titers.

Marginally increased C3a levels were observed on Day 43 of the dosing phase in animals administered 198.4 mg/kg/dose SC or IV, compared with control and baseline values, and were considered potentially related to HL161ANS due to the consistency between sexes and the small magnitude of change. C3a is an effector in the complement system and has various stimulatory functions on the immune system. HL161ANS-related effects in clinical chemistry test results consisted of minimally to mildly decreased total protein concentration on Day 43 of the dosing phase in animals administered up to 198.4 mg/kg/dose SC or IV. Minimally to moderately decreased albumin concentration was observed on Days 16 and/or 43 of the dosing phase in animals administered >50 mg/kg/dose SC, males administered >50 mg/kg/dose IV, and females administered 198.4 mg/kg/dose IV. Minimally decreased globulin concentration was observed on Day 43 of the dosing phase in males administered 50 or 100 mg/kg/dose SC or >50 mg/kg/dose IV and females administered 50 mg/kg/dose SC or IV. Males administered 50 mg/kg/dose IV exhibited evidence of reversibility of the albumin effect by Day 43 of the dosing phase, and all other effects in clinical chemistry test results for animals administered 198.4 mg/kg/dose SC or IV exhibited evidence of reversibility by Day 22 or 50 of the recovery phase.

An HL161ANS-related effect in hematology test results was small in magnitude and consisted of minimally decreased absolute neutrophil count on Day 43 of the dosing phase in animals administered 198.4 mg/kg/dose IV. These effects exhibited evidence of reversibility by Day 22 or 50 of the recovery phase, except for in one male administered 198.4 mg/kg/dose IV. One female administered 198.4 mg/kg/dose SC was noted with minimally increased absolute monocyte count on Day 43 of the dosing phase, which correlated with microscopic findings of vascular inflammation and infiltrates of mononuclear cells. At the terminal sacrifice, the HL161ANS-related microscopic finding of vascular inflammation likely associated with immune complex-mediated damage was noted in the lung, liver, gall bladder, kidney, stomach, small and large intestines, tongue, heart, uterus, and Subcutaneous Injection Site E of one female administered 198.4 mg/kg/dose SC. The additional findings in this animal included minimal extramedullary hematopoiesis and slight hypertrophy of Kupffer cells of the liver and minimal hypertrophy of the tunica media in the lung vessels. No HL161ANS-related findings were noted at the recovery sacrifice.

In conclusion, male and female cynomolgus monkeys were administered vehicle control article/diluent or 50, 100, 198.4 mg/kg/dose HL161ANS via SC and/or IV injection twice weekly for 6 weeks. Increased C3A levels were observed on Day 43 of the dosing phase in animals administered 198.4 mg/kg/dose SC or IV. This finding was reversible during the recovery phase. Clinical pathology changes included mildly decreased total protein concentration in both sexes administered up to 198.4 mg/kg/dose SC or IV; minimally to moderately decreased albumin concentration both sexes administered up to 198.4 mg/kg/dose SC, males administered ≥50 mg/kg/dose IV, and females administered 198.4 mg/kg/dose IV; minimally decreased globulin concentration in males administered 50 or 100 mg/kg/dose SC or ≥50 mg/kg/dose IV and females administered 50 mg/kg/dose SC or IV; and minimally decreased absolute neutrophil count in both sexes administered 198.4 mg/kg/dose IV. These findings were reversible during the recovery phase.

HL161ANS-related microscopic findings included vascular inflammation in the lung, liver, gall bladder, kidney, stomach, small and large intestines, tongue, heart, uterus, and Subcutaneous Injection Site E of one female administered 198.4 mg/kg/dose SC. No HL161ANS-related findings were noted at the recovery sacrifice. Due to the systemic nature of the microscopic findings of animals administered 198.4 mg/kg/dose SC, effects for this dose were considered adverse. Due to the mild severity of the findings and the lack of an impact on the health and wellbeing of animals administered 100 mg/kg/dose SC or 198.4 mg/kg/dose IV, effects for these doses were considered nonadverse. Thus, the no observed adverse effect level (NOAEL) is 100 mg/kg/dose via SC injection and 198.4 mg/kg/dose via IV injection. The SC dose level corresponded to a mean maximum observed concentration ($C_{max}$) value of 964 mg/L on Day 43 of the dosing phase and area under the concentration-time curve over a dosing interval (AUCtau or AUC0-72) value of 2290 mg/L on Day 22 of the dosing phase (it should be noted that the AUC0-72 on Day 43 was note able to be calculated since the terminal sacrifice was one day following the Day 43 dose). The IV dose level corresponded to a mean maximum observed concentration ($C_{max}$) and area under the concentration-time curve over a dosing interval (AUCtau or $AUC_{0-72}$) values of 7100 mg/L and 10800 mg×day/L on Day 43 of the dosing phase.

Example 15: Subcutaneous and/or Intravenous Injection Dose Range Finding Toxicity, Toxicokinetic, and Pharmacodynamic Study with HL161ANS in Cynomolgus Monkeys The purpose of this study was to evaluate the toxicity and determine the toxicokinetics (TK) and pharmacodynamics (PD) of HL161ANS when administered twice weekly via subcutaneous (SC) injection or once weekly via intravenous (IV, slow bolus) injection to cynomolgus monkeys for at least 6 weeks.

Male and female cynomolgus monkeys were assigned to six groups, and doses were administered as indicated in the following table. Animals were dosed via intravenous and/or subcutaneous injection once or twice weekly at a volume of 1 mL/kg/dose. The vehicle control article/diluent was HL161ANS Formulation Buffer.

| Group | Dose Level[b] (mg/kg/dose) | Dose Concentration[b] (mg/mL) | Number of Animals | |
|---|---|---|---|---|
| | | | Males | Females |
| 1 (Control-IV and SC)[a] | 0 | 0 | 1 | 1 |
| 2 (Low - IV) | 3 | 3 | 2 | 2 |
| 3 (Mid-Low -IV) | 10 | 10 | 2 | 2 |
| 4 (Mid-High -IV) | 30 | 30 | 2 | 2 |
| 5 (High - IV) | 100 | 100 | 3 | 3 |
| 6 (High - SC) | 100 | 100 | 2 | 2 |

IV = Intravenous;
SC = Subcutaneous
[a]Group 1 was administered vehicle control article only. On Days 1, 8, 15, 22, 29, and 36, subcutaneous administration was followed by intravenous administration. On Days 4, 11, 18, 25, 32, and 39, subcutaneous administration only.
[b]Animals were dosed at a volume of 1 mL/kg/dose.

Assessment of toxicity was based on mortality, clinical observations, body weights, food consumption, dermal observations, immunotoxicology, and clinical and anatomic pathology. Blood samples were collected for toxicokinetic evaluation and anti-drug antibody analysis.

No HL161ANS-related deaths occurred and no HL161ANS-related clinical or dermal observations, alterations to body weight, body weight gain, or food consumption, organ weight differences, macroscopic observations, or microscopic findings were noted.

HL161ANS-related clinical chemistry effects noted for animals administered 100 mg/kg/dose IV or SC were limited to minimally to mildly decreased albumin concentration noted for individual animals. The decreased albumin was more consistently noted on Day 15 or 22 through 50 for animals administered 100 mg/kg/dose SC whereas it was mostly noted on Days 36 and 43 of the dosing phase for animals administered 100 mg/kg/dose IV. A mechanism was not known for decreased albumin.

In conclusion, male and female cynomolgus monkeys were administered HL161ANS formulation buffer (vehicle control) via subcutaneous injection twice weekly and intravenous injection once weekly or 3, 10, or 100 mg/kg/dose HL161ANS via once weekly intravenous injection or 100 mg/kg/dose HL161ANS via twice weekly subcutaneous injection. HL161ANS was well tolerated at all dose levels and all dose routes. No HL161ANS-related deaths occurred and no HL161ANS-related clinical observations, alterations to body weight, body weight gain, or food consumption, organ weight differences, macroscopic observations, or microscopic findings were noted. No HL161ANS-related clinical pathology effects were observed in animals administered up to 100 mg/kg/dose IV. HL161ANS-related clinical pathology effects noted for animals administered 100 mg/kg/dose SC were limited to minimally to mildly decreased albumin concentration on Days 15 or 22 through Day 50. Based on these findings, 100 mg/kg/dose HL161ANS, the highest dose level administered, via intravenous or subcutaneous injection is considered the maximum tolerated dose (MTD).

Example 16: A Phase 1 Study to Assess the Safety, Tolerability, Pharmacokinetics, and Pharmacodynamics of HL161ANS in Healthy Participants This Example describes a Phase 1, randomized, placebo-controlled, double-blind, sequential parallel-group study to investigate the safety, tolerability, pharmacokinetics (PK), and pharmacodynamics (PD) of single and multiple ascending doses of HL161ANS in healthy adult male participants and adult female participants of non-childbearing potential (NCBP). Participants participate in 1 dosing cohort.

There are 6 single ascending dose (SAD) cohorts (100, 300, 600, and 1,200 mg intravenous [IV]; and 300 and 600 mg subcutaneous [SC]). There are 2 multiple ascending dose (MAD) cohorts (300 and 600 mg SC once weekly [QW]) and 2 optional MAD cohorts (150 and 450 mg SC QW). Each MAD cohort is to receive 4 weekly administrations of HL161ANS or placebo. Each cohort is to dose 2 sentinel subjects (one active and one placebo).

The SAD cohorts each consist of 6 and 2 participants in HL161ANS and placebo, respectively, and the 4 MAD cohorts each consist of 10 and 2 participants in HL161ANS and placebo, respectively. Therefore, the study is to have a total of up to 96 participants (76 in HL161ANS and 20 in placebo).

Selected doses are not to exceed the fixed doses of 1,530 mg IV for SAD and 800 mg SC for MAD.

Participants are to be screened to assess eligibility for randomization into the study. For SAD cohorts, participants are to be randomized into 6 sequential dose cohorts, with 8 participants per cohort. For each SAD cohort, 2 participants are to be randomized 1:1 to receive HL161ANS or placebo for sentinel dosing, then the remaining 6 participants are to be randomized 5:1 to receive L161ANS or placebo, if HL161ANS is well tolerated in the respective sentinel participants.

For MAD cohorts, participants are to be randomized into up to 4 sequential cohorts (2 planned and 2 optional), with 12 participants per cohort. For each MAD cohort, 2 participants are to be randomized 1:1 to receive HL161ANS or placebo for sentinel dosing, then the remaining 10 participants are to be randomized 9:1 to receive HL161ANS or placebo, if HL161ANS is well tolerated in the respective sentinel participants.

Objectives and endpoints are shown in Table 25

TABLE 25

| OBJECTIVES | ENDPOINTS |
|---|---|
| Primary | |
| To evaluate the safety and tolerability of HL161ANS following single and multiple doses in healthy participants | AEs, SAEs, and AEs leading to treatment discontinuation |

TABLE 25-continued

| OBJECTIVES | ENDPOINTS |
|---|---|
| Secondary | |
| To evaluate the PK of HL161ANS following single and multiple doses in healthy participants | PK profile of HL161ANS, assessed via serum concentrations of HL161ANS over time |
| To evaluate the PD of HL161ANS following single and multiple doses in healthy participants | PD profile of HL161ANS, assessed via serum concentrations of total IgG and IgG subclasses over time |
| To assess the immunogenicity of HL161ANS following single and multiple doses in healthy participants | Number of participants with treatment--emergent positive ADAs and nAbs |
| Exploratory | |
| To evaluate the effect of HL161ANS on selected markers of inflammation and immune status in healthy participants | Change from baseline in markers of inflammation and immune status: Immune complexes IgA and IgM concentrations Complement C3 and C4 after multiple doses Titers of tetanus toxin-specific and diphtheria toxin-specific antibodies will be measured after multiple doses |

Abbreviations: ADA = anti-drug antibody; AE = adverse event; IgA = immunoglobulin A; IgG = immunoglobulin G; IgM = immunoglobulin M; nAb = neutralizing antibody; PD = pharmacodynamics; PK = pharmacokinetics; SAE = serious adverse event.

What is claimed is:

1. An anti-FcRn antibody or an antigen binding fragment thereof comprising:
   a light chain variable region comprising LCDR1 comprising the amino acid sequence of SEQ ID NO: 9, LCDR2 comprising the amino acid sequence of SEQ ID NO: 2, and LCDR3 comprising the amino acid sequence of SEQ ID NO: 3; and
   a heavy chain variable region comprising HCDR1 comprising the amino acid sequence of SEQ ID NO: 11, HCDR2 comprising the amino acid sequence of SEQ ID NO: 6, and HCDR3 comprising the amino acid sequence of SEQ ID NO: 7.

2. The anti-FcRn antibody or an antigen binding fragment thereof according to claim 1, comprising a light chain variable region comprising the amino acid sequence of SEQ ID NO: 4 and a heavy chain variable region comprising the amino acid sequence of SEQ ID NO: 8,
   wherein the amino acid of N25 in the amino acid sequence of SEQ ID NO: 4 is substituted with Ser (S), and the amino acid of C32 in the amino acid sequence of SEQ ID NO: 8 is substituted with Ser (S).

3. The anti-FcRn antibody according to claim 1, wherein the anti-FcRn antibody comprises an Fc region, wherein the Fc region is an IgG1 Fc region or an IgG4 Fc region.

4. The anti-FcRn antibody according to claim 3, wherein the Fc region is an IgG1 Fc region comprising Leu234Ala and Leu235Ala amino acid substitutions.

5. A polynucleotide encoding the anti-FcRn antibody or antigen binding fragment thereof according to claim 1.

6. A recombinant expression vector comprising the polynucleotide according to claim 5.

7. A host cell transformed with the recombinant expression vector according to claim 6.

8. A method for producing an anti-FcRn antibody or an antigen binding fragment thereof, comprising:
   culturing the host cell according to claim 7 to produce an antibody; and
   isolating and purifying the produced antibody to recover an antibody that specifically binds to FcRn.

9. A pharmaceutical composition comprising the anti-FcRn antibody or antigen binding fragment thereof according to claim 1, and a pharmaceutically acceptable carrier.

10. A method of treating an autoimmune disease in a subject in need thereof, comprising administering to the subject the anti-FcRn antibody or antigen-binding fragment thereof according to claim 1.

11. The method according to claim 10, wherein the autoimmune disease is selected from the group consisting of: autoimmune neutropenia, Guillain-Barré syndrome, epilepsy, autoimmune encephalitis, Isaacs' syndrome, nevus syndrome, pemphigus vulgaris, deciduous pemphigus, bullous pemphigoid, acquired epidermolysis bullosa, gestational pemphigoid, mucous membrane pemphigoid, antiphospholipid syndrome, autoimmune anemia, myasthenia gravis, autoimmune Graves' disease, thyroid eye disease (TED), Goodpasture syndrome, multiple sclerosis, rheumatoid arthritis, lupus, idiopathic thrombocytopenic purpura (ITP), warm autoimmune hemolytic anemia (WAIHA), chronic inflammatory demyelinating polyneuropathy (CIDP), lupus nephritis, and membranous nephropathy.

12. The method according to claim 10, wherein the administering is parenteral.

13. The method according to claim 12, wherein the administering is subcutaneous or intravenous.

14. The method according to claim 10, wherein the administering is at a dose from 300 mg to 2400 mg.

15. The method according to claim 10, wherein the administering is once weekly, once in two weeks, once in three weeks or once monthly.

16. The method according to claim 10, wherein the administering is subcutaneous once weekly at a dose from 300 mg to 900 mg.

17. The method according to claim 10, wherein the administering is subcutaneous once in two weeks at a dose from 300 mg to 1800 mg.

18. The method according to claim 10, wherein the administering does not result in more than 5% or more than 10% decrease in blood albumin levels in the subject compared to the blood albumin levels prior to the administration of the antiFcRn antibody or antigen-binding fragment.

19. The method according to claim 10, wherein the administering does not result in more than 5% or more than 10% increase in blood total cholesterol or low-density lipoprotein (LDL) levels in the subject compared to the blood total cholesterol or LDL levels prior to the administration of the anti-FcRn antibody or antigen-binding fragment.

20. The method according to claim 10, wherein the subject is human.

* * * * *